US008455717B2

(12) United States Patent
Shoseyov et al.

(10) Patent No.: US 8,455,717 B2
(45) Date of Patent: Jun. 4, 2013

(54) COLLAGEN PRODUCING PLANTS AND METHODS OF GENERATING AND USING SAME

(75) Inventors: Oded Shoseyov, Karmei Yosef (IL); Hanan Stein, Nes-Ziona (IL)

(73) Assignee: CollPlant Ltd., Nes Ziona (IL)

( * ) Notice: Subject to any disclaimer, the term of this patent is extended or adjusted under 35 U.S.C. 154(b) by 613 days.

(21) Appl. No.: 11/730,071

(22) Filed: Mar. 29, 2007

(65) Prior Publication Data

US 2007/0186312 A1 Aug. 9, 2007

Related U.S. Application Data

(63) Continuation-in-part of application No. PCT/IL2005/001045, filed on Sep. 28, 2005.

(60) Provisional application No. 60/613,719, filed on Sep. 29, 2004.

(51) Int. Cl.
*C12N 15/82* (2006.01)

(52) U.S. Cl.
USPC ............................ 800/287; 800/278; 435/468

(58) Field of Classification Search
None
See application file for complete search history.

(56) References Cited

U.S. PATENT DOCUMENTS

| | | | |
|---|---|---|---|
| 4,855,237 | A | 8/1989 | Morinaga et al. |
| 4,945,050 | A | 7/1990 | Sanford et al. |
| 5,316,931 | A | 5/1994 | Donson et al. |
| 5,593,859 | A | 1/1997 | Prockop et al. |
| 5,693,507 | A | 12/1997 | Daniell et al. |
| 6,617,431 | B1 | 9/2003 | Gruber et al. |
| 6,713,662 | B1 | 3/2004 | Karatzas et al. |
| 2002/0098578 | A1 | 7/2002 | Prockop et al. |
| 2002/0142391 | A1 | 10/2002 | Kivirikko et al. |
| 2004/0018592 | A1 | 1/2004 | Bell et al. |
| 2005/0059053 | A1 | 3/2005 | Fischer et al. |
| 2005/0172342 | A1 | 8/2005 | Karatzas et al. |
| 2012/0284817 | A1 | 11/2012 | Shoseyov et al. |

FOREIGN PATENT DOCUMENTS

| | | |
|---|---|---|
| EP | 951537 | 10/1999 |
| EP | 2357241 | 8/2011 |
| WO | WO 87/06261 | 10/1987 |
| WO | WO 97/04123 | 2/1997 |
| WO | WO 97/38710 | 10/1997 |
| WO | WO 00/20612 | 4/2000 |
| WO | WO 01/29242 | 4/2001 |
| WO | WO 01/34647 * | 5/2001 |
| WO | WO 02/099067 | 12/2002 |
| WO | WO 03/066847 | 8/2003 |
| WO | WO 2004/057001 | 7/2004 |
| WO | WO 2004/058956 | 7/2004 |
| WO | WO 2006/035442 | 4/2006 |

OTHER PUBLICATIONS

Horvath et al. The production of recombinant proteins in transgenic barley grains. (2000) PNAS; vol. 97, pp. 1914-1919.*
Marttila et al. A barley (Hordeum vulgare L.) LEA3 protein, HVA1, is abundant in protein storage vacuoles. (1996) Planta; vol. 199; pp. 602-611.*
Neuhaus et al. Sorting of proteins to vacuoles in plant cells. (1998) Plant Molecular Biology; vol. 38, pp. 127-144.*
Communication Pursuant to Article 94(3) EPC Dated Jun. 9, 2008 From the European Patent Office Re.: Application No. 05789469.3.
Communication Pursuant to Article 94(3) EPC Dated Dec. 19, 2008 From the European Patent Office Re.: Application No. 05789469.3.
Communication Pursuant to Article 94(3) EPC Dated Jan. 28, 2008 From the European Patent Office Re.: Application No. 05789469.3.
Communication Pursuant to Article 96(2) EPC Dated Aug. 21, 2007 From the European Patent Office Re.: Application No. 05789469.3.
Office Action Dated Aug. 3, 2009 From the Israeli Patent Office Re.: Application No. 182320 and Its Translation Into English.
Galili et al. "The 5' Leader Sequence of Tobacco Mosaic Virus RNA Enhances the Expression of Foreign Gene Transcripts in Vitro and in Viivo", Nucleic Acids Research, 15(8): 3257-3273, 1987.
Laemmli "Cleavage of Structural Proteins During the Assembly of the Head of Bacteriophage T4", Nature, 227: 680-685, Aug. 15, 1970.
Maijsterek et al "Prospects and Limitations of the Rational Engineering of Fibrillar Collagens", Protein Science, 12: 2063-2072, 2003.
Nokelainen "Recombinant Human Collagens. Characterization of Type II Collagen Expressed in Insect Cells and Production of Types I-III Collagen in the Yeast Pichia Pastoris", Collagen Research Unit, Biocenter Oulu and Department of Mediical Biochemistry, University of Oulu, Finland, 70 P., Aug. 10, 200.
Osorio "Development of Transgenic Barley Expressing Human Type I Collagen", Thesis for the Degree of Master of Science in Crop Science, Washington State University, 132 P., Dec. 2004.
Perret et al "Unhydroxylated Triple-Helical Collagen 1 Produced in Transgenic Plants Provides New Clues on the Role of Hydroxyproline in Collagen Folding and Fibril Formation", The Journal of Biological Chemistry, 276(47): 43693-43698, Nov. 23, 2001.
Ritala et al "Production of a Recombinant Industrial Protein Using Barley Cell Cultures", Protein Expression and Purification, 59: 274-281, 2008.
Bulleid et al. "Recombinant expression systems for the production of collagen", Biochem Soc Trans.,28(4), p. 350-353, 2000.
Hieta et al. "Cloning and Characterization of a Low Molecular Weight Prolyl 4-Hydroxylase From Arabidopsis Thaliana", The Journal of Biological Chemistry, 277(26): 23965-23971, 2002.
Hulmes "Building collagen molecules, fibrils, and suprafibrillar structures", Journal Struct Biol., vol. 137(1-2), p. 2-10, 2002.

(Continued)

*Primary Examiner* — Cathy Kingdon Worley

(57) ABSTRACT

A method of producing collagen in a plant and plants producing collagen are provided. The method is effected by expressing in the plant at least one type of a collagen alpha chain in a manner enabling accumulation of the collagen alpha chain in a subcellular compartment devoid of endogenous P4H activity, thereby producing the collagen in the plant.

15 Claims, 10 Drawing Sheets

OTHER PUBLICATIONS

Inkinen Connective Tissue Formation in Wound Healing an Experimental Study, Academic Dissertation, Sep. 2003. University of Helsinki, Faculty of Science, Department of Biosciences, Division of Biochemistry, 2003.
Merle et al. "Hydroxylated Human Homotrimeric Collagen I in Agrobacterium Tumefaciens-Mediated Transient Expression and in Transgenic Tobacco Plant", FEBS Letters, 515: 114-118, 2002.
Olsen et al. "Recombinant Collagen and Gelatin for Drug Delivery", Advanced Drug Delivery Reviews, 55(12): 1547-1567, 2003. p. 1553, 1-h Col.-p. 1554, r-h Col.
Ruggiero et al. "Triple Helix Assembly and Processing of Human Collagen Produced in Transgenic Tobacco Plants", FEBS Letters, 469(1): 132-136, 2000. p. 136, 1-h Col.
Tanaka et al. "Plant prolyl hydroxylase recognizes poly(L-proline) II helix", Journal Biol Chem., vol. 256(22), p. 11397-11400, 1981.
Turpeenniemi-Hujanen et al. "Concomitant Hydroxylation of Proline and Lysine Residues in Collagen Using Purified Enzymes in Vitro", Biochim Biophys Acta, vol. 800(1), p. 59-65, 1984.
Vuorela et al. "Assembly of Human Prolyl 4-Hydroxylase and Type III Collagen in the Yeast Pichia Pastoris: Formation of a Stable Enzyme Tetramer Requires Coexpression With Collagen and Assembly of a Stable Collagen Requires Coexpression With Prolyl 4-Hydroxylase", The EMBO Journal, 16(22): 6702-6712, 1997.
Wang et al. "The Third Activity for Lysyl Hydroxylase 3: Galactosylation of Hydroxylysyl Residues in Collagens in Vitro", Matrix Biology, 21(7): 559-566, 2002.
Fromm et al. "Stable Tranformation of Maize After Gene Transfer by Electroporation", Nature, 319: 791-793, 1986.
Wong Po Foo et al. "Genetic Engineering of Fibrous Proteins: Spider Dragline Silk and Collagen", Advanced Drug Delivery Reviews, 54(8): 1131-1143, Oct. 18, 2002. Abstract.
Dawson et al. "A Tobacco Mosaic Virus-Hybrid Expresses and Loses an Added Gene". Virology, 172: 285-292, 1989.
Gatenby "Regulation and Expression of Plant Genes in Microorganisms", Plant Biotechnology, Chap.5: 93-112, 1989.
Horsch et al. "Leaf Disc Transformation", Plant Molecular Biological Manual, A5: 1-9, 1988.
Klee et al. "Agrobacterium-Mediated Plants Transformation and Its Further Applications to Plant Biology", Annual Review of Plant Physiology, 38: 467-486, 1987.
Klein et al. "Factors Influencing Gene Delivery Into Zea Mays Cells by High-Velocity Microprojectiles", Bio/Technology, 6: 559-563, 1988.
McCabe et al. "Stable Transformation of Soybean (Glycine Max) by Particle Acceleration", Bio/Technology, 6: 923-926, 1988.
Neuhaus et al. "Plant Transformation by Microinjection Techniques", Physiologia Plantarum, 79: 213-217, 1990.
Neuhaus et al. "Transgenic Rapeseed Plants Pbtained by the Microinjection of DNA Into Microspore-Derived Embryoids", Theoretical and Applied Genetics, 75: 30-36, 1987.
Ohta "High-Efficiency Genetic Transformation of Maize by a Mixture of Pollen and Exogenous DNA", Proc. Natl. Acad. Sci. USA, 83: 715-719, Feb. 1986.
Sanford "Biolistic Plant Transformation", Physiologia Plantarum, 79: 206-209, 1990.
Shimamoto et al. "Fertile Transgenic Rice Plants Regenerated From Transformed Protoplasts", Nature, 338: 274-276, 1989.
Toriyama et al. "Transgenic Rice Plants After Direct Gene Transfer Into Protoplasts", Bio/Technology, 6: 1072-1074, 1988.
Zhang et al. "Transgenic Rice Plants Produced by Electroporation-Mediated Plasmid Uptake Into Protoplasts", Plant Cell Reports, 7: 379-384, 1988.
Communication Pursuant to Article 94(3) EPC Dated Jun. 9, 2008 From the European Patent Office Re.: Application No. 05789469.3.
Response Dated Dec. 1, 2009 to Official Action of Aug. 7, 2009 From the State Intellectual Property Office of the People's Republic of China Re.: Application No. 200580040821.7.
Translation of Office Action Dated Aug. 7, 2009 From the State Intellectual Property Office of the People's Republic of China Re.: Application No. 200580040821.7.
International Preliminary Report on Patentability Dated Apr. 12, 2007 From the International Bureau of WIPO Re.: Application No. PCT/IL2005/001045.
International Search Report Dated Mar. 20, 2006 From the International Searching Authority Re.: Application No. PCT/IL2005/001045.
Written Opinion Dated Mar. 20, 2006 From the International Searching Authority Re.: Application No. PCT/IL2005/001045.
Written Opinion Dated Apr. 23, 2008 From the Intellectual Property Office of Singapore Issued by Australian Government, IP Australia Re.: Application No. SG 200702377-3.
Partial European Search Report Dated Mar. 17, 2011 From the European Patent Office Re. Application No. 10181115.6.
Nokelainen et al. "High-Level Production of Human Type I Collagen in the Yeast Pichia Pastoris", Yeast, XP008068378, 18: 797-806, Jan. 1, 2011. Table I.
Olsen et al. "Production of Human Type I Collagen in Yeast Reveals Unexpected New Insights Into the Molecular Assembly of Collagen Trimers", The Journal of Biological Chemistry, XP002969135, 276(26): 24038-24043, Jun. 29, 2001. Figs.1, 4, Table 1.
Perret et al. "Prolyl Hydroxylation of Collagen Type I Is Required for Efficient Binding to Integrin $\alpha 1\beta 1$ and the Platelet Glycoprotein VI But Not to $\alpha 2\beta 1$", The Journal of Biological Chemistry, XP002626606, 278(32): 29873-29879, Aug. 8, 2003.
Stephan et al. "Expression and Supramolecular Assembly of Recombinant $\alpha 1$(VIII) and $\alpha 2$(VIII) Collagen Homotrimers", The Journal of Biological Chemistry, XP002626607, 279(20): 21469-21477, May 14, 2004.
Toman et al. "Production of Recombinant Human Type I Procollagen Homotrimer in the Mammary Gland of Transgenic Mice", Transgenic Research, XP002626608, 8(6): 415-427, Dec. 1999. p. 416, r-h Col., Figs.1, 5.
Communication Pursuant to Article 94(3) EPC Dated Mar. 19, 2012 From the European Patent Office Re. Application No. 10181115.6.
Translation of Notice of Reason for Rejection Dated May 10, 2011 From the Japanese Patent Office Re. Application No. 2007-534176.
Associate Report of Telephone Communication Dated May 25, 2012 From the Examiner of the Japanese Patent Office Re. 2007-534176.
Summons to Attend Oral Proceedings Pursuant to Rule 115(1) EPC Dated Jul. 30, 2012 From the European Patent Office Re. Application No. 05789469.3.
Office Action Dated Aug. 23, 2010 From the Israeli Patent Office Re.: Application No. 182320 and Its Translation Into English.
Examination Report Dated Aug. 4, 2010 From the Instituto Mexicano de la Propriedad Industrial Re. Application No. MX/a/2007/003767.
Examination Report Dated Nov. 5, 2010 From the Instituto Mexicano de la Propriedad Industrial Re. Application No. MX/a/2007/003767.
Response Dated Oct. 13, 2010 to Translation of Office Action of Aug. 13, 2010 From the State Intellectual Property Office of the People's Republic of China Re.: Application No. 200580040821.7.
Response Dated Oct. 14, 2010 to Examination Report of Aug. 4, 2010 From the Instituto Mexicano de la Propriedad Industrial Re. Application No. MX/a/2007/003767.
Response Dated Nov. 18, 2010 to Examiner's Report of Apr. 1, 2010 From the Australian Government, IP Australia Re.: Application No. 2007201384.
Translation of Office Action Dated Aug. 16, 2010 From the State Intellectual Property Office of the People's Republic of China Re.: Application No. 200580040821.7.
Nakamura et al. "Protein Targeting to the Vacuole in Plant Cells", Plant Physiology, 101(1): 1-5, Jan. 1993.
Examiner's Report Dated Jan. 4, 2011 From the Australian Government, IP Australia Re.: Application No. 2007201384.
Office Action Dated Feb. 1, 2012 From the Israeli Patent Office Re.: Application No. 182320 and Its Translation Into English.
Examination Report Dated Apr. 5, 2011 From the Government of India, Patent Office Re. Application No. 1819/CHENP/2007.
Communication of a Notice of Opposition Dated Jun. 28, 2011 From the European Patent Office Re.: Application No. 05789469.3.
Communication of Notices of Opposition (R. 79(1) EPC) Dated Jul. 8, 2011 From the European Patent Office Re.: Application No. 05789469.3.

European Search Report and the European Search Opinion Dated Jun. 24, 2011 From the European Patent Office Re. Application No. 10181115.6.

Jiang et al. "Membrane Anchors for Vacuolar Targeting: Application in Plant Bioreactors", Trends in Biotechnology, XP004335891, 20(3): 99-102, Mar. 1, 2002.

Marty "Plant Vacuoles", Plant Cell, XP002640272, 11(4): 587-599, Apr. 1999.

Matsuoka et al. "Cis-Elements of Protein Transport to the Plant Vacuoles", Journal of Experimental Botany, XP001188956, 50(331): 165-174, Feb. 1, 1999.

Yoshida et al. "The Plant Vesicular Transport Engineering for Production of Useful Recombinant Proteins", Journal of Molecular Catalysis B: Enzymatic, XP002640279, 28(4-6); 167-171, Jun. 1, 2004. Fig.1, Tables 1-3.

Examination Report Dated Aug. 27, 2010 From the Government of India, Patent Office Re. Application No. 1819/CHENP/2007.

Response Dated Feb. 22, 2011 to Examination Report of Aug. 27, 2010 From the Government of India, Patent Office Re. Application No. 1819/CHENP/2007.

Response Dated Jan. 13, 2011 to Examination Report of Nov. 5, 2010 From the Instituto Mexicano de la Propriedad Industrial Re. Application No. MX/a/2007/003767.

Communication Pursuant to Article 94(3) EPC Dated Mar. 19, 20120 From the European Patent Office Re. Application No. 10168971.9.

Response Dated Mar. 28, 2011 to Examiner's Report of Jan. 4, 2011 From the Australian Government, IP Australia Re.: Application No. 2007201384.

European Search Report and the European Search Opinion Dated Jul. 8, 2011 From the European Patent Office Re. Application No. 10168971.9.

Response Dated Jul. 12, 2011 to Notice of Reason for Rejection of May 10, 2011 From the Japanese Patent Office Re. Application No. 2007-534176.

Response Dated Jul. 14, 2011 to Examination Report of Apr. 5, 2011 From the Government of India, Patent Office Re. Application No. 1819/CHENP/2007.

Communication Pursuant to Rules 70(2) and 70a(2) EPC and Reference to Rule 39(1) EPC Dated Aug. 22, 2011 From the European Patent Office Re. Application No. 10168971.9.

Communication Pursuant to Rules 70(2) and 70a (2) EPC and Reference to Rule 39(1) EPC Dated Aug. 29, 2011 From the European Patent Office Re. Application No. 10181115.6.

Examiner's Report Dated Sep. 23, 2011 From the Australian Government, IP Australia Re. Application No. 2011211341.

Takamatsu et al. "Expression of Bacterial Chloramphenicol Acetyltransferase Gene in Tobacco Plants Mediated by TMV-RNA", The EMBO Journal, 6(2): 307-311, 1987.

Takamatsu et al. "Production of Enkephalin in Tobacco Protoplasts Using Tobacco Mosaic Virus RNA Vector", FEBS Letters, 269: 73-76, 1990. Abstract.

Requisition by the Examiner Dated Jun. 8, 2012 From the Canadian Intellectual Property Office Re. Application No. 2,582,051.

Communication Pursuant to Article 94(3) EPC Dated Aug. 21, 2012 From the European Patent Office Re. Application No. 10168971.9.

Restriction Official Action Dated Aug. 30, 2012 From the US Patent and Trademark Office Re. U.S. Appl. No. 13/541,880.

Translation of Notice of Reason for Rejection Dated Sep. 2, 2011 From the Japanese Patent Office Re. Application No. 2007-534176.

Brief Communication (Letter From the Opponent) Dated Nov. 29, 2012 From the European Patent Office Re.: Application No. 05789469.3.

Niemes et al. "Sorting of Plant Vacuolar Proteins Is Initiated in the ER", The Plant Journal, 62: 601-614, 2010.

Response Dated Nov. 17, 2011 to Notice of Reason for Rejection of Sep. 2, 2011 From the Japanese Patent Office Re. Application No. 2007-534176.

Response Dated Nov. 22, 2011 to Examiner's Report of Sep. 23, 2011 From the Australian Government, IP Australia Re. Application No. 2011211341.

Stein et al. "Production of Bioactive, Post-Translationally Modified, Heterotrimeric, Human Recombinant Type-I Collagen in Transgenic Tobacco", Biomacromolecules, 10(9): 2640-2645, Aug. 14, 2009.

Communication Pursuant to Article 94(3) EPC Dated Feb. 13, 2013 From the European Patent Office Re. Application No. 10181115.6.

Examiner's Report Dated Apr. 1, 2010 From the Australian Government, IP Australia Re.: Application No. 2007201384.

Bulleid et al. "Recombinant Expression Systems for the Production of Collagen", Biochemical Society Transactions, 28(4): 350-353, 2000.

French et al. "Bacterial Gene Inserted in an Engineered RNA Virus: Efficient Expression in Monocotyledonous Plant Cells", Science, 231: 1294-1297, 1986.

Hare et al. "Metabolic Implications of Stress-induced Proline Accumulation in Plants", Plant Growth Regulation, 21: 79-102, 1997.

Hulmes "Building Collagen Molecules, Fibrils, and Suprafibrillar Structures", Journal of Structurural Biology, 137(1-2): 2-10, 2002.

Inkinen "Connective Tissue Formation in Wound Healing. An Experimental Study", Academic Dissertation, University of Helsinki, Faculty of Science, Department of Biosciences, Division of Biochemistry, Sep. 2003.

Klee et al. "Agrobacterium Tranformation System", In: 'Cell Culture and Somatic Cell Genetics', Molecular Biology of Plant Nuclear Genes, 6: 2-23, 1989.

Merle et al. "Hydroxylated Human Homotrimeric Collagen I in Agrobacterium Tumefaciens-Mediated Transient Expression and in Transgenic Tobacco Plant", FEBS Letters, XP004347752, 515(1-3): 114-118, Mar. 27, 2002.

Ruggiero et al. "Triple Helix Assembly and Processing of Human Collagen Produced in Transgenic Tobacco Plants", FEBS Letters, XP004261062, 469(1): 132-136, Mar. 3, 2000. p. 136, 1-h Col.

Tanaka et al. "Plant Prolyl Hydroxylase Recognizes Poly(L-Proline) II Helix", Journal of Biological Chemistry, 256(22): 11397-11400, 1981.

Turpeenniemi-Hujanen et al. "Concomitant Hydroxylation of Proline and Lysine Residues in Collagen Using Purified Enzymes in Vitro", Biochimica et Biophysica Acta, 800(1): 59-65, 1984.

Vuorela et al. "Assembly of Human Prolyl 4-Hydroxylase and Type III Collagen in the Yeast Pichia Pastoris: Formation of a Stable Enzyme Tetramer Requires Coexpression With Collagen and Assembly of a Stable Collagen Requires Coexpression With Prolyl 4-Hydroxylase", The EMBO Journal, XP002153732, 16(22): 6702-6712, 1997.

Wang et al. "The Third Activity for Lysyl Hydroxylase 3: Galactosylation of Hydroxylysyl Residues in Collagens in Vitro", Matrix Biology, XP002368908, 21(7): 559-566, Nov. 2002.

Zhang et al "Purification and Characterization of a 44-kDa Recombinant Collagen I α 1 Fragment From corn Grain", Journal of Agricultural and Food Chemistry, 57: 880-887, 2009.

Response Dated Dec. 21, 2010 to Office Action of Aug. 23, 2010 From the Israeli Patent Office Re.: Application No. 182320.

Communication Pursuant to Rule 58 EPC or Rule 159 EPC Dated Nov. 24, 2010 From the European Patent Office Re. Application No. 10168971.9.

Response Dated Jan. 6, 2011 to Communication Pursuant to Rule 58 EPC or Rule 159 EPC of Nov. 24, 2010 From the European Patent Office Re. Application No. 10168971.9.

Hare et al. "Metabolic implications of stress-induced proline accumulation in plants", Plant Growth Regulation, vol. 21, p. 79-102, 1997.

* cited by examiner

Fig. 2

COLLAGEN PRODUCING PLANTS AND METHODS OF GENERATING AND USING SAME

RELATED APPLICATIONS

The present application is a continuation-in-part of PCT/IL2005/001045 filed on Sep. 28, 2005, which claims the benefit of U.S. Provisional Patent Application No. 60/613,719, filed on Sep. 29, 2004, the contents of which are incorporated herein by reference.

FIELD AND BACKGROUND OF THE INVENTION

The present invention relates to collagen producing plants and methods of generating and using same. More particularly, the present invention relates to a novel approach for generating plants capable of producing high levels of hydroxylated collagen chains which are capable of forming native triple helix type I collagen fibers.

Collagens are the main structural proteins responsible for the structural integrity of vertebrates and many other multicellular organisms. Type I collagen represents the prototypical fibrillar collagen and is the major collagen type in most tissues.

Type I collagen is the predominant collagen component of bone and tendon and is found in large amounts in skin, aorta, and lung. Type I collagen fibers provide great tensile strength and limited extensibility. The most abundant molecular form of type I collagen is a heterotrimer composed of two different alpha chains [alpha $1(I)]_2$ and alpha $2(I)$ (Inkinen, 2003). All fibrillar collagen molecules contain three polypeptide chains constructed from a repeating Gly-X-Y triplet, where X and Y can be any amino acid but are frequently the imino acids proline and hydroxyproline.

Fibril forming collagens are synthesized as precursor procollagens containing globular N- and C-terminal extension propeptides. The biosynthesis of procollagen is a complex process involving a number of different post-translational modifications including proline and lysine hydroxylation, N-linked and O-linked glycosylation and both intra- and inter-chain disulphide-bond formation. The enzymes carrying out these modifications act in a coordinated fashion to ensure the folding and assembly of a correctly aligned and thermally stable triple-helical molecule.

Each procollagen molecule assembles within the rough endoplasmic reticulum from the three constituent polypeptide chains. As the polypeptide chain is co-translationally translocated across the membrane of the endoplasmic reticulum, hydroxylation of proline and lysine residues occurs within the Gly-X-Y repeat region. Once the polypeptide chain is fully translocated into the lumen of the endoplasmic reticulum the C-propeptide folds. Three pro-alpha chains then associate via their C-propeptides to form a trimeric molecule allowing the Gly-X-Y repeat region to form a nucleation point at its C-terminal end, ensuring correct alignment of the chains. The Gly-X-Y region then folds in a C-to-N direction to form a triple helix.

The temporal relationship between polypeptide chain modification and triple-helix formation is crucial as hydroxylation of proline residues is required to ensure stability of the triple helix at body temperature, once formed, the triple helix no longer serves as a substrate for the hydroxylation enzyme. The C-propeptides (and to a lesser extent the N-propeptides) keep the procollagen soluble during its passage through the cell (Bulleid et al., 2000). Following or during secretion of procollagen molecules into the extracellular matrix, propeptides are removed by procollagen N- and C-proteinases, thereby triggering spontaneous self-assembly of collagen molecules into fibrils (Hulmes, 2002). Removal of the propeptides by procollagen N- and C-proteinases lowers the solubility of procollagen by >10000-fold and is necessary and sufficient to initiate the self-assembly of collagen into fibers. Crucial to this assembly process are short non triple-helical peptides called telopeptides at the ends of the triple-helical domain, which ensure correct registration of the collagen molecules within the fibril structure and lower the critical concentration for self-assembly (Bulleid et al., 2000). In nature, the stability of the triple-helical structure of collagen requires the hydroxylation of prolines by the enzyme prolyl-4-hydroxylase (P4H) to form residues of hydroxyproline within a collagen chain.

Plants expressing collagen chains are known in the art, see for example, U.S. Pat. No. 6,617,431 and (Merle et al., 2002, Ruggiero et al., 2000). Although plants are capable of synthesizing hydroxyproline-containing proteins the prolyl hydroxylase that is responsible for synthesis of hydroxyproline in plant cells exhibits relatively loose substrate sequence specificity as compared with mammalian P4H and thus, production of collagen containing hydroxyproline only in the Y position of Gly-X-Y triplets requires plant co-expression of collagen and P4H genes (Olsen et al, 2003).

An attempt to produce human collagens that rely on the hydroxylation machinery naturally present in plants resulted in collagen that is poor in proline hydroxylation (Merle et al., 2002). Such collagen melts or loses its triple helical structure at temperatures below 30° C. Co-expression of collagen and prolyl-hydroxylase results with stable hydroxylated collagen that is biologically relevant for applications at body temperatures (Merle et al., 2002).

Lysyl hydroxylase (LH, EC 1.14.11.4), galactosyltransferase (EC 2.4.1.50) and glucosyltransferase (EC 2.4.1.66) are enzymes involved in posttranslational modifications of collagens. They sequentially modify lysyl residues in specific positions to hydroxylysyl, galactosylhydroxylysyl and glucosylgalactosyl hydroxylysyl residues. These structures are unique to collagens and essential for their functional activity (Wang et al, 2002). A single human enzyme, Lysyl hydroxylase 3 (LH3) can catalyze all three consecutive steps in hydroxylysine linked carbohydrate formation (Wang et al, 2002).

Hydroxylysins of a human collagen expressed in tobacco form less than 2% of the hydroxylysins found in a bovine collagen (0.04% of residues/1.88% of residues). This suggests that plant endogenic Lysyl hydroxylase is unable to sufficiently hydroxylate lysines in collagen.

While reducing the present invention to practice, the present inventors uncovered that efficient hydroxylation of collagen chains relies upon sequestering of the collagen chain along with an enzyme capable of correctly modifying this polypeptide.

SUMMARY OF THE INVENTION

According to one aspect of the present invention there is provided a method of producing collagen in a plant or an isolated plant cell comprising expressing in the plant or the isolated plant cell at least one type of a collagen alpha chain and exogenous P4H in a manner enabling accumulation of the at least one type of the collagen alpha chain and the exogenous P4H in a subcellular compartment devoid of endogenous P4H activity, thereby producing the collagen in the plant.

According to an additional aspect of the present invention there is provided According to further features in preferred embodiments of the invention described below, the method further comprises expressing exogenous LH3 in the subcellular compartment devoid of endogenous P4H activity.

According to still further features in the described preferred embodiments the at least one type of the collagen alpha chain includes a signal peptide for targeting to an apoplast or a vacuole.

According to still further features in the described preferred embodiments the at least one type of the collagen alpha chain is devoid of an ER targeting or retention sequence.

According to still further features in the described preferred embodiments the at least one type of the collagen alpha chain is expressed in a DNA-containing organelle of the plant.

According to still further features in the described preferred embodiments the exogenous P4H includes a signal peptide for targeting to an apoplast or a vacuole.

According to still further features in the described preferred embodiments the exogenous P4H is devoid of an ER targeting or retention sequence.

According to still further features in the described preferred embodiments the exogenous P4H is expressed in a DNA-containing organelle of the plant.

According to still further features in the described preferred embodiments the at least one type of the collagen alpha chain is alpha 1 chain.

According to still further features in the described preferred embodiments the at least one type of the collagen alpha chain is alpha 2 chain.

According to still further features in the described preferred embodiments the at least one type of the collagen alpha chain includes a C-terminus and/or an N-terminus propeptide.

According to still further features in the described preferred embodiments the plant is selected from the group consisting of Tobacco, Maize, Alfalfa, Rice, Potato, Soybean, Tomato, Wheat, Barley, Canola and Cotton.

According to still further features in the described preferred embodiments the at least one type of the collagen alpha chain or the exogenous P4H are expressed in only a portion of the plant.

According to still further features in the described preferred embodiments the portion of the plant is leaves, seeds, roots, tubers or stems.

According to still further features in the described preferred embodiments the exogenous P4H is capable of specifically hydroxylating the Y position of Gly-X-Y triplets of the at least one type of the collagen alpha chain.

According to still further features in the described preferred embodiments the exogenous P4H is human P4H.

According to still further features in the described preferred embodiments the plant is subjected to a stress condition.

According to still further features in the described preferred embodiments the stress condition is selected from the group consisting of drought, salinity, injury, cold and spraying with stress inducing compounds.

According to another aspect of the present invention there is provided a genetically modified plant or isolated plant cell capable of accumulating a collagen alpha chain having a hydroxylation pattern identical to that produced when the collagen alpha chain is expressed in human cells.

According to yet another aspect of the present invention there is provided a genetically modified plant or isolated plant cell capable of accumulating a collagen alpha chain in a subcellular compartment devoid of endogenous P4H activity.

According to still further features in the described preferred embodiments the genetically modified plant further comprises an exogenous P4H.

According to still further features in the described preferred embodiments the at least one type of the collagen alpha chain includes a signal peptide for targeting to an apoplast or a vacuole.

According to still further features in the described preferred embodiments the at least one type of the collagen alpha chain is devoid of an ER targeting or retention sequence.

According to still further features in the described preferred embodiments the at least one type of the collagen alpha chain is expressed in a DNA-containing organelle of the plant.

According to still further features in the described preferred embodiments the exogenous P4H includes a signal peptide for targeting to an apoplast or a vacuole.

According to still further features in the described preferred embodiments the exogenous P4H is devoid of an ER targeting or retention sequence.

According to still further features in the described preferred embodiments the exogenous P4H is expressed in a DNA-containing organelle of the plant.

According to still further features in the described preferred embodiments the collagen alpha chain is alpha 1 chain.

According to still further features in the described preferred embodiments the collagen alpha chain is alpha 2 chain.

According to still further features in the described preferred embodiments the collagen alpha chain includes a C-terminus and/or an N-terminus propeptide.

According to still another aspect of the present invention there is provided a plant system comprising a first genetically modified plant capable of accumulating a collagen alpha 1 chain and a second genetically modified plant capable of accumulating a collagen alpha 2 chain.

According to yet another aspect of the present invention there is provided a plant system comprising a first genetically modified plant capable of accumulating a collagen alpha 1 chain and a collagen alpha 2 chain and a second genetically modified plant capable of accumulating P4H.

According to still further features in the described preferred embodiments at least one of the first genetically modified plant and the second genetically modified plant further comprises exogenous P4H.

According to yet another aspect of the present invention there is provided a method of producing fibrillar collagen comprising: (a) expressing in a first plant a collagen alpha 1 chain; (b) expressing in a second plant a collagen alpha 2 chain, wherein expression in the first plant and the second plant the is configured such that the collagen alpha 1 chain and the collagen alpha 2 chain are each capable of accumulating in a subcellular compartment devoid of endogenous P4H activity; and (c) crossing the first plant and the second plant and selecting progeny expressing the collagen alpha 1 chain and the collagen alpha 2 chain thereby producing fibrillar collagen.

According to still further features in the described preferred embodiments the method further comprises expressing an exogenous P4H in each of the first plant and the second plant.

According to still further features in the described preferred embodiments each of the collagen alpha 1 chain and the collagen alpha 2 chain includes a signal peptide for targeting to an apoplast or a vacuole.

According to still further features in the described preferred embodiments each of the collagen alpha 1 chain and the collagen alpha 2 chain is devoid of an ER targeting or retention sequence.

According to still further features in the described preferred embodiments steps (a) and (b) are effected via expression in a DNA-containing organelle of the plant.

According to still further features in the described preferred embodiments the exogenous P4H includes a signal peptide for targeting to an apoplast or a vacuole.

According to still further features in the described preferred embodiments the exogenous P4H is devoid of an ER targeting or retention sequence.

According to still further features in the described preferred embodiments the exogenous P4H is expressed in a DNA-containing organelle of the plant.

According to still further features in the described preferred embodiments each of the collagen alpha 1 chain and the collagen alpha 2 chain includes a C-terminus and/or an N-terminus propeptide.

According to still further features in the described preferred embodiments the exogenous P4H is capable of specifically hydroxylating the Y position of Gly-X-Y triplets of the at least one type of the collagen alpha chain.

According to still further features in the described preferred embodiments the exogenous P4H is human P4H.

According to still further features in the described preferred embodiments the first plant and the second plant are subjected to a stress condition.

According to still further features in the described preferred embodiments the stress condition is selected from the group consisting of drought, salinity, injury, heavy metal toxicity and cold stress.

According to yet another aspect of the present invention there is provided a method of producing fibrillar collagen comprising: (a) expressing in a first plant a collagen alpha 1 chain and a collagen alpha 2 chain, wherein expression in the first plant is configured such that the collagen alpha 1 chain and the collagen alpha 2 chain are each capable of accumulating in a subcellular compartment devoid of endogenous P4H activity; (b) expressing in a second plant an exogenous P4H capable of accumulating in the subcellular compartment devoid of endogenous P4H activity; and (c) crossing the first plant and the second plant and selecting progeny expressing the collagen alpha 1 chain, the collagen alpha 2 chain and the P4H thereby producing fibrillar collagen.

According to yet another aspect of the present invention there is provided a nucleic acid construct comprising a polynucleotide encoding a human P4H positioned under the transcriptional control of a promoter functional in plant cells.

According to still further features in the described preferred embodiments the promoter is selected from the group consisting of the CaMV 35S promoter, the Ubiquitin promoter, the rbcS promoter and the SVBV promoter.

According to yet another aspect of the present invention there is provided a genetically modified plant or isolated plant cell being capable of expressing collagen alpha 1 chain, collagen alpha 2 chain, P4H, LH3 and protease C and/or protease N.

According to still further features in the described preferred embodiments the collagen alpha 1 chain and the collagen alpha 2 chain are each capable of accumulating in a subcellular compartment devoid of endogenous plant P4H activity.

According to yet another aspect of the present invention there is provided a genetically modified plant or isolated plant cell being capable of accumulating collagen having a temperature stability characteristic identical to that of mammalian collagen.

According to still further features in the described preferred embodiments the collagen is type I collagen.

According to still further features in the described preferred embodiments the mammalian collagen is human collagen.

According to yet another aspect of the present invention there is provided a collagen-encoding sequence optimized for expression in a plant.

According to still further features in the described preferred embodiments the collagen encoding sequence is as set forth by SEQ ID NO:1.

The present invention successfully addresses the shortcomings of the presently known configurations by providing a plant capable of expressing correctly hydroxylated collagen chains which are capable of assembling into collagen having properties similar to that of human collagen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a shows a cloning scheme of type I collagen alpha I chain or type II collagen alpha 2 chain into a plant expression vector in accordance with some embodiments of the present invention; FIG. 1b shows a cloning scheme of the enzyme prolyl-4-hydroxylase (P4H) into a plant expression vector in accordance with some embodiments of the present invention; FIG. 1c shows a cloning scheme proteinase C or proteinase N into a plant expression vector in accordance with some embodiments of the present invention; FIG. 1d shows a cloning scheme of Lysyl hydroxylase 3 (LH3) into a plant expression vector in accordance with some embodiments of the present invention. A multiple cloning site set forth in SEQ ID NO: 29 is shown at the bottom of each panel.

FIG. 2 illustrates various co-transformations approaches. Each expression cassette is represented by the short name of the coding sequence. The coding sequences are specified in table 1. Each co-transformation was performed by two pBIN-PLUS binary vectors. Each rectangle represents a single pBINPLUS vector carrying one, two or three expression cassettes. Promoter and terminators are specified in Example 1.

In FIG. 6a—total soluble protein from tobacco 2-9 (expressing only col alpha1 and no P4H) and 3-5 (expressing both col alpha 1+2 and human P4H alpha and beta subunits) were subjected to heat treatment (15 minutes in 38° C. or 43° C.) followed by Trypsin digestion (20 minutes in R.T.) and tested with anti-Collagen I antibody in a Western blot procedure. Positive controls were samples of 500 ng human collagen I+total soluble proteins of w.t. tobacco. In FIG. 6b—total soluble proteins were extracted from transgenic tobacco 13-6 (expressing collagen I alpha 1 and alpha 2 chains—pointed by arrows, human P4H alpha and beta subunits and human LH3) and subjected to heat treatment (20 minutes in 33° C., 38° C. or 42° C.), immediately cooled on ice to prevent reassembly of triple helix and incubated with pepsin for 30 minutes in room temperature (about 22° C.) followed by testing with anti-Collagen I antibody ((#AB745 from Chemicon Inc.) in a standard Western blot procedure. Positive control was sample of 50 ng human collagen I (#CC050 from Chemicon Inc., extracted from human placenta by pepsin digestion) which was added to total soluble proteins extracted from w.t. tobacco.

DESCRIPTION OF THE PREFERRED EMBODIMENTS

Figure 1A:
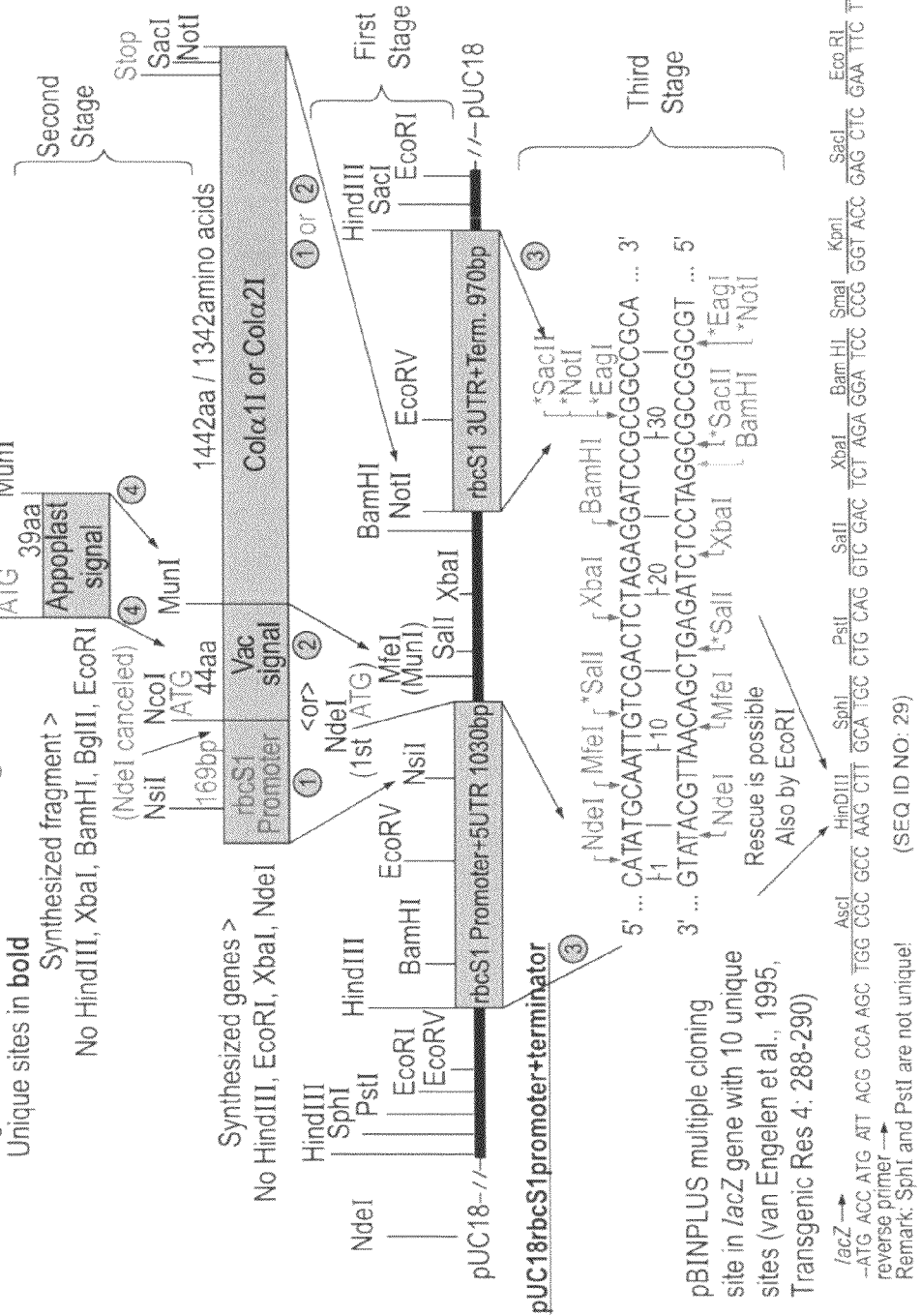
FIGS. 1a-d illustrate construction of various expression cassettes and vectors used to transform test plants. All of the coding sequences synthesized as a part of the present study were optimized for expression in tobacco.

The present invention is of plants expressing and accumulating collagen which can be used to produce collagen and collagen fibers which display characteristics of mammalian collagen.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Collagen producing plants are known in the art. Although such plants can be used to produce collagen chains as well as collagen, such chains are incorrectly hydroxylated and thus self-assembly thereof, whether in planta or not, leads to collagen which is inherently unstable.

While reducing the present invention to practice, the present inventors have devised a plant expression approach which ensures correct hydroxylation of collagen chains and thus enables in-planta production of collagen which closely mimics the characteristics (e.g. temperature stability) of human type I collagen.

Thus, according to one aspect of the present invention there is provided a genetically modified plant which is capable of expressing at least one type of a collagen alpha chain and accumulating it in a subcellular compartment which is devoid of endogenous P4H activity.

As used herein, the phrase "genetically modified plant" refers to any lower (e.g. moss) or higher (vascular) plant or a tissue or an isolated cell thereof (e.g., of a cell suspension) which is stably or transiently transformed with an exogenous polynucleotide sequence. Examples of plants include Tobacco, Maize, Alfalfa, Rice, Potato, Soybean, Tomato, Wheat, Barley, Canola, Cotton, Carrot as well as lower plants such as moss.

As used herein, the phrase "collagen chain" refers to a collagen subunit such as the alpha 1 or 2 chains of collagen fibers, preferably type I fibers. As used herein, the phrase "collagen" refers to an assembled collagen trimer, which in the case of type I collagen includes two alpha 1 chains and one alpha 2 chain. A collagen fiber is collagen which is devoid of terminal propeptides C and N.

As is used herein, the phrase "subcellular compartment devoid of endogenous P4H activity" refers to any compartmentalized region of the cell which does not include plant P4H or an enzyme having plant-like P4H activity. Examples of such subcellular compartments include the vacuole, apoplast and cytoplasm as well as organelles such as the chloroplast, mitochondria and the like.

Any type of collagen chain can be expressed by the genetically modified plant of the present invention. Examples include Fibril-forming collagens (types I, II, III, V, and XI), networks forming collagens (types IV, VIII, and X), collagens associated with fibril surfaces (types IX, XII, and XIV), collagens which occur as transmembrane proteins (types XIII and XVII), or form 11-nm periodic beaded filaments (type VI). For further description please see Hulmes, 2002.

Preferably, the collagen chain expressed is an alpha 1 and/or 2 chain of type I collagen. The expressed collagen alpha chain can be encoded by any polynucleotide sequences derived from any mammal. Preferably, the sequences encoding collagen alpha chains are human and are set forth by SEQ ID NOs: 1 and 4.

Typically, alpha collagen chains expressed in plants may or may not include their terminal propeptides (i.e. propeptide C and propeptide N).

Ruggiero et al. (2000) note that processing of procollagen by plant proteolytic activity is different then normal processing in human and that propeptide C is removed by plant proteolytic activity although the cleavage site is unknown. Cleavage of the C propeptide may take place on a procollagen peptide before the assembly of trimmer (association of three C-Propeptides is essential for initiating the assembly of trimmers).

N-propeptide cleavage by plant proteolytic activity takes place in mature plants but not in plantlets. Such cleavage removes 2 amino acids from the N telopeptide (2 out of 17).

The C-propeptides (and to a lesser extent the N-propeptides) maintain the procollagen soluble during its passage through the animal cell (Bulleid et al., 2000) and are expected to have a similar effect in the plant cell. Following or during secretion of procollagen molecules into the extracellular matrix, propeptides are removed by procollagen N- and C-proteinases, thereby triggering spontaneous self-assembly of collagen molecules into fibrils (Hulmes, 2002). Removal of the propeptides by procollagen N- and C-proteinases lowers the solubility of procollagen by >10000-fold and is necessary and sufficient to initiate the self-assembly of collagen into fibers. Crucial to this assembly process are short non triple-helical peptides called telopeptides at the ends of the triple-helical domain, which ensure correct registration of the collagen molecules within the fibril structure and lower the critical concentration for self-assembly (Bulleid et al., 2000). Prior art describe the use of pepsin to cleave the propeptides during production of collagen (Bulleid et al 2000). However pepsin damages the telopeptides and as a result, pepsin-extracted collagen is unable to form ordered fibrillar structures (Bulleid et al 2000).

Protein disulfide isomerase (PDI) that form the beta subunit of human P4H was shown to bind to the C-propeptide prior to trimmer assembly thereby also acting as a molecular chaperone during chain assembly (Ruggiero et al, 2000).

The use of human Procollagen I N-proteinase and Procollagen C-proteinase expressed in a different plants may generate collagen that is more similar to the native human collagen and can form ordered fibrillar structures.

In a case where N or C propeptides or both are included in the expressed collagen chain, the genetically modified plant of the present invention can also express the respective protease (i.e. C or N or both). Polynucleotide sequences encoding such proteases are exemplified by SEQ ID NOs: 18 (protease C) and 20 (Protease N). Such proteases can be expressed such that they are accumulated in the same subcellular compartment as the collagen chain.

Accumulation of the expressed collagen chain in a subcellular compartment devoid of endogenous P4H activity can be effected via any one of several approaches.

For example, the expressed collagen chain can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the Mitochondrion transit peptide (included in Swiss-Prot entry P46643, amino acids 1-28). The Examples section which follows provides additional examples of suitable signal sequences as well as guidelines for employing such signal sequences in expression of collagen chains in plant cells.

Alternatively, the sequence of the collagen chain can be modified in a way which alters the cellular localization of collagen when expressed in plants.

As is mentioned hereinabove, the ER of plants includes a P4H which is incapable of correctly hydroxylating collagen chains. Collagen alpha chains natively include an ER targeting sequence which directs expressed collagen into the ER where it is post-translationally modified (including incorrect hydroxylation). Thus, removal of the ER targeting sequence will lead to cytoplasmic accumulation of collagen chains which are devoid of post translational modification including any hydroxylations.

Example 1 of the Examples section which follows describes generation of collagen sequences which are devoid of ER sequences.

Still alternatively, collagen chains can be expressed and accumulated in a DNA containing organelle such as the chloroplast or mitochondria. Further description of chloroplast expression is provided hereinbelow.

As is mentioned hereinabove, hydroxylation of alpha chains is required for assembly of a stable type I collagen. Since alpha chains expressed by the genetically modified plant of the present invention accumulate in a compartment devoid of endogenous P4H activity, such chains must be isolated from the plant, plant tissue or cell and in-vitro hydroxylated. Such hydroxylation can be achieved by the method described by Turpeenniemi-Hujanen and Myllyla (Concomitant hydroxylation of proline and lysine residues in collagen using purified enzymes in vitro. Biochim Biophys Acta. 1984 Jul. 16; 800(1):59-65).

Although such in-vitro hydroxylation can lead to correctly hydroxylated collagen chains, it can be difficult and costly to achieve.

To overcome the limitations of in-vitro hydroxylation, the genetically modified plant of the present invention preferably also co-expresses P4H which is capable of correctly hydroxylating the collagen alpha chain(s) [i.e. hydroxylating only the proline (Y) position of the Gly-X-Y triplets]. P4H is an enzyme composed of two subunits, alpha and beta. Both are needed to form an active enzyme while the Beta subunit also posses a chaperon function.

The P4H expressed by the genetically modified plant of the present invention is preferably a human P4H which is encoded by, for example, SEQ ID's NO:12 and 14. In addition, P4H mutants which exhibit enhanced substrate specificity, or P4H homologues can also be used.

A suitable P4H homologue is exemplified by an *Arabidopsis* oxidoreductase identified by NCBI accession NP_179363. Pairwise alignment of this protein sequence and a human P4H alpha subunit conducted by the present inventors revealed the highest homology between functional domains of any known P4H homologs of plants.

Since P4H needs to co-accumulate with the expressed collagen chain, the coding sequence thereof is preferably modified accordingly (addition of signal sequences, deletions which may prevent ER targeting etc).

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues. A single human enzyme, Lysyl hydroxylase 3 (LH3) can catalyze all three consecutive steps in hydroxylysine linked carbohydrate formation.

Thus, the genetically modified plant of the present invention preferably also expresses mammalian LH3. An LH3 encoding sequence such as that set forth by SEQ ID NO: 22 can be used for such purposes.

The collagen chain(s) and modifying enzymes described above can be expressed from a stably integrated or a transiently expressed nucleic acid construct which includes polynucleotide sequences encoding the alpha chains and/or modifying enzymes (e.g. P4H and LH3) positioned under the transcriptional control of plant functional promoters. Such a nucleic acid construct (which is also termed herein as an expression construct) can be configured for expression throughout the whole plant, defined plant tissues or defined plant cells, or at define developmental stages of the plant. Such a construct may also include selection markers (e.g. antibiotic resistance), enhancer elements and an origin of replication for bacterial replication.

It will be appreciated that constructs including two expressible inserts (e.g. two alpha chain types, or an alpha chain and P4H) preferably include an individual promoter for each insert, or alternatively such constructs can express a single transcript chimera including both insert sequences from a single promoter. In such a case, the chimeric transcript includes an IRES sequence between the two insert sequences such that the downstream insert can be translated therefrom.

Numerous plant functional expression promoters and enhancers which can be either tissue specific, developmentally specific, constitutive or inducible can be utilized by the constructs of the present invention, some examples are provided hereinunder.

As used herein in the specification and in the claims section that follows the phrase "plant promoter" or "promoter" includes a promoter which can direct gene expression in plant cells (including DNA containing organelles). Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric, i.e., formed of portions of at least two different promoters.

Thus, the plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQI promoter, barley leaf thionin BTH6 promoter, and rice actin promoter.

Examples of tissue specific promoters include, without being limited to, bean phaseolin storage protein promoter, DLEC promoter, PHS promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

Preferably the promoter utilized by the present invention is a strong constitutive promoter such that over expression of the construct inserts is effected following plant transformation.

It will be appreciated that any of the construct types used in the present invention can be co-transformed into the same plant using same or different selection markers in each construct type. Alternatively the first construct type can be introduced into a first plant while the second construct type can be introduced into a second isogenic plant, following which the transgenic plants resultant therefrom can be crossed and the progeny selected for double transformants. Further self-crosses of such progeny can be employed to generate lines homozygous for both constructs.

There are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by a progeny of the plant.

In addition, several method exist in which a nucleic acid construct can be directly introduced into the DNA of a DNA containing organelle such as a chloroplast.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not limited to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

The above described transformation approaches can be used to produce collagen chains and/or modifying enzymes as well as assembled collagen (with or without propeptides) in any species of plant, or plant tissue or isolated plants cell derived therefrom.

Preferred plants are those which are capable of accumulating large amounts of collagen chains, collagen and/or the processing enzymes described herein. Such plants may also be selected according to their resistance to stress conditions and the ease at which expressed components or assembled collagen can be extracted. Examples of preferred plants include Tobacco, Maize, Alfalfa, Rice, Potato, Soybean, Tomato, Wheat, Barley, Canola and Cotton.

Collagen fibers are extensively used in the food and cosmetics industry. Thus, although collagen fiber components (alpha chains) and modifying enzymes expressed by plants find utility in industrial synthesis of collagen, complete collagen production in plants is preferred for its simplicity and cost effectiveness.

Several approaches can be used to generate type I collagen in plants. For example, collagen alpha 1 chain can be isolated from a plant expressing collagen alpha 1 and P4H (and optionally LH3) and mixed with a collagen alpha 2 chain which is isolated from a plant expressing collagen alpha 2 and P4H (and optionally LH3 and protease C and/or N). Since collagen alpha 1 chain self assembles into a triple helix by itself, it may be necessary to denature such a homo-trimer prior to mixing and renaturation with the collagen alpha 2 chain.

Preferably, a first plant expressing collagen alpha 1 and P4H (and optionally LH3 and protease C and/or N) can be crossed with a second (and preferably isogenic) plant which expresses collagen alpha 2 or alternatively, a first plant expressing both alpha chains can be crossed with a second plant expressing P4H and optionally LH3 and protease C and/or N.

It should be noted that although the above described plant breeding approaches utilize two individually transformed plants, approaches which utilize three or more individually transformed plants, each expressing one or two components can also be utilized.

One of ordinary skill in the art would be well aware of various plant breeding techniques and as s such no further description of such techniques is provided herein.

Although plant breeding approaches are preferred, it should be noted that a single plant expressing collagen alpha 1 and 2, P4H and LH3 (and optionally protease C and/or N) can be generated via several transformation events each designed for introducing one more expressible components into the cell. In such cases, stability of each transformation event can be verified using specific selection markers.

In any case, transformation and plant breeding approaches can be used to generate any plant, expressing any number of components. Presently preferred are plants which express collagen alpha 1 and 2 chains, P4H, LH3 and at least one protease (e.g. protease C and/or N). As is further described in the Examples section which follows, such plants accumulate collagen which exhibits stability at temperatures of up to 42° C.

Progeny resulting from breeding or alternatively multiple-transformed plants can be selected, by verifying presence of exogenous mRNA and/or polypeptides by using nucleic acid or protein probes (e.g. antibodies). The latter approach is preferred since it enables localization of the expressed polypeptide components (by for example, probing fractionated plants extracts) and thus also verifies a potential for correct processing and assembly. Examples of suitable probes are provided in the Examples section which follows Once collagen-expressing progeny is identified, such plants are further cultivated under conditions which maximize expression of the collagen chains as well as the modifying enzymes.

Since free proline accumulation may facilitate over production of different proline-rich proteins including the collagen chains expressed by the genetically modified plants of the present invention, preferred cultivating conditions are those which increase free proline accumulation in the cultivated plant.

Free proline accumulates in a variety of plants in response to a wide range of environmental stresses including water deprivation, salinization, low temperature, high temperature, pathogen infection, heavy metal toxicity, anaerobiosis, nutrient deficiency, atmospheric pollution and UV-irradiation (Hare and Cress, 1997).

Free proline may also accumulate in response to treatment of the plant or soil with compounds such as ABA or stress inducing compounds such as copper salt, paraquate, salicylic acid and the like.

Thus, collagen-expressing progeny can be grown under different stress conditions (e.g. different concentrations of NaCl ranging from 50 mM up to 250 mM). In order to further enhance collagen production, the effect of various stress conditions on collagen expression will examined and optimized with respect to plant viability, biomass and collagen accumulation.

Plant tissues/cells are preferably harvested at maturity, and the collagen fibers are isolated using well know prior art extraction approaches, one such approach is detailed below.

Leaves of transgenic plants are ground to a powder under liquid nitrogen and the homogenate is extracted in 0.5 M acetic acid containing 0.2 M NaCl for 60 h at 4° C. Insoluble material is removed by centrifugation. The supernatant containing the recombinant collagen is salt-fractionated at 0.4 M and 0.7 M NaCl. The 0.7 M NaCl precipitate, containing the recombinant heterotrimeric collagen, is dissolved in and dialyzed against 0.1 M acetic acid and stored at −20° C. (following Ruggiero et al., 2000).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Constructs and Transformation Schemes

Figure 1B:
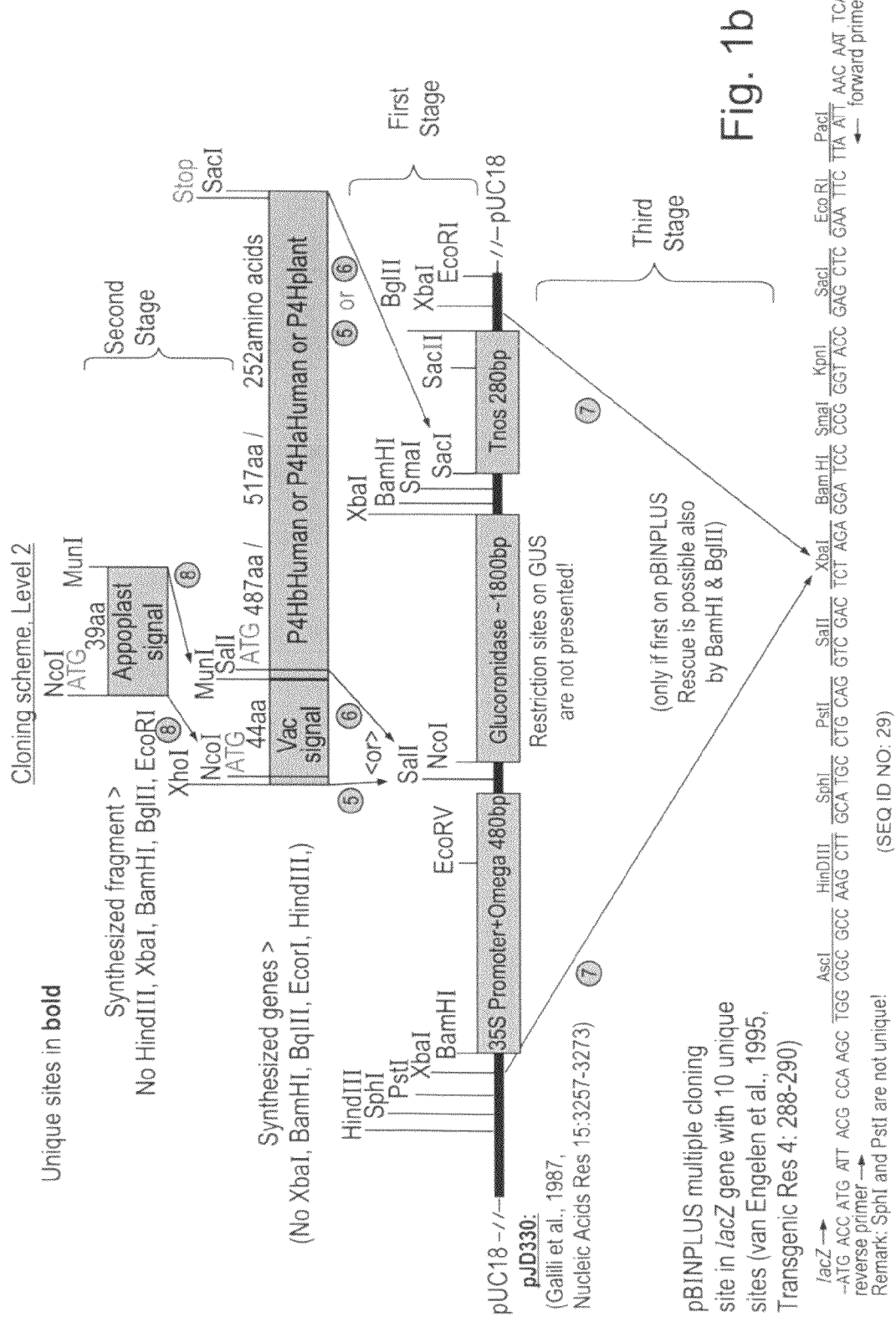
Figure 1C:
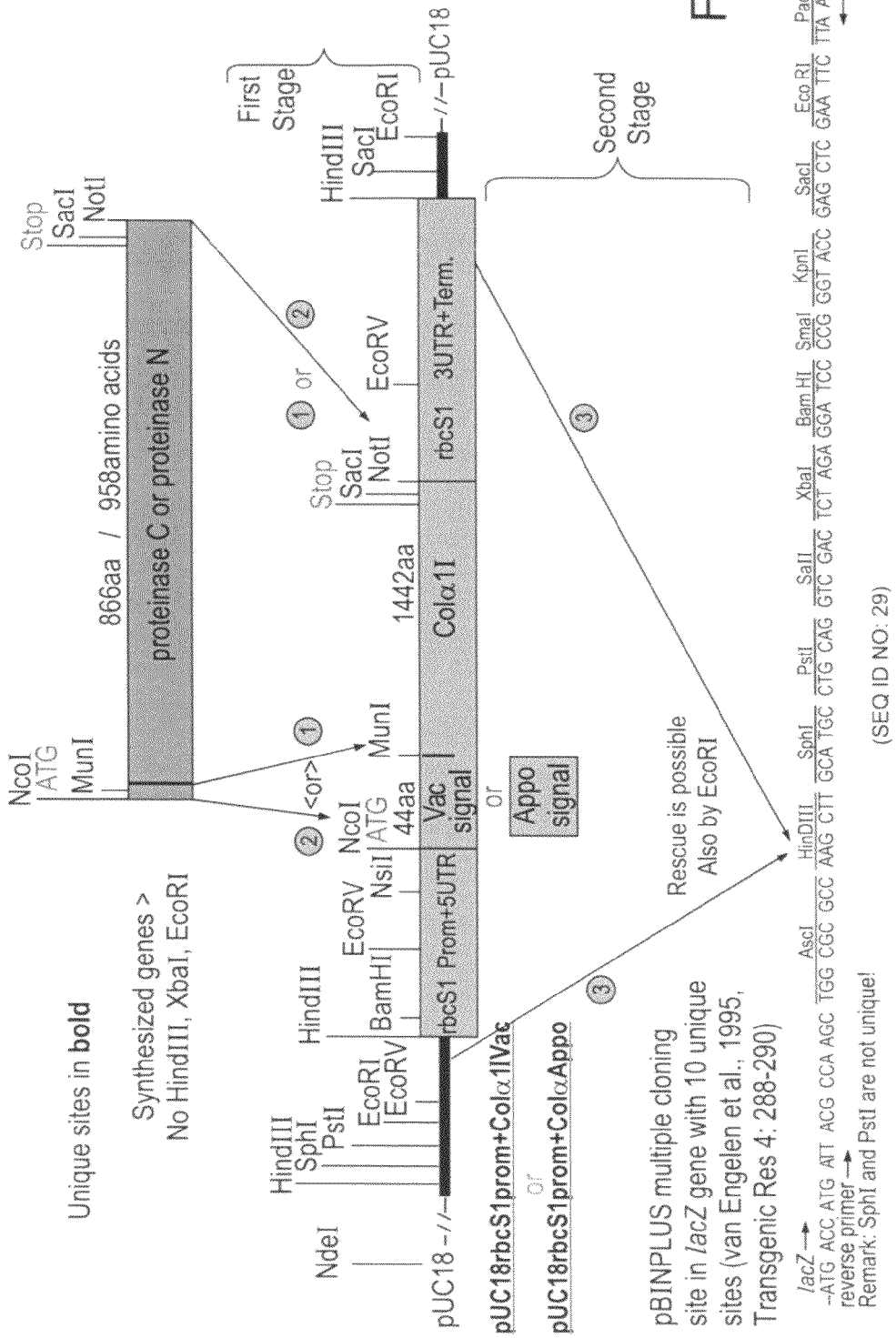
Figure 1D:
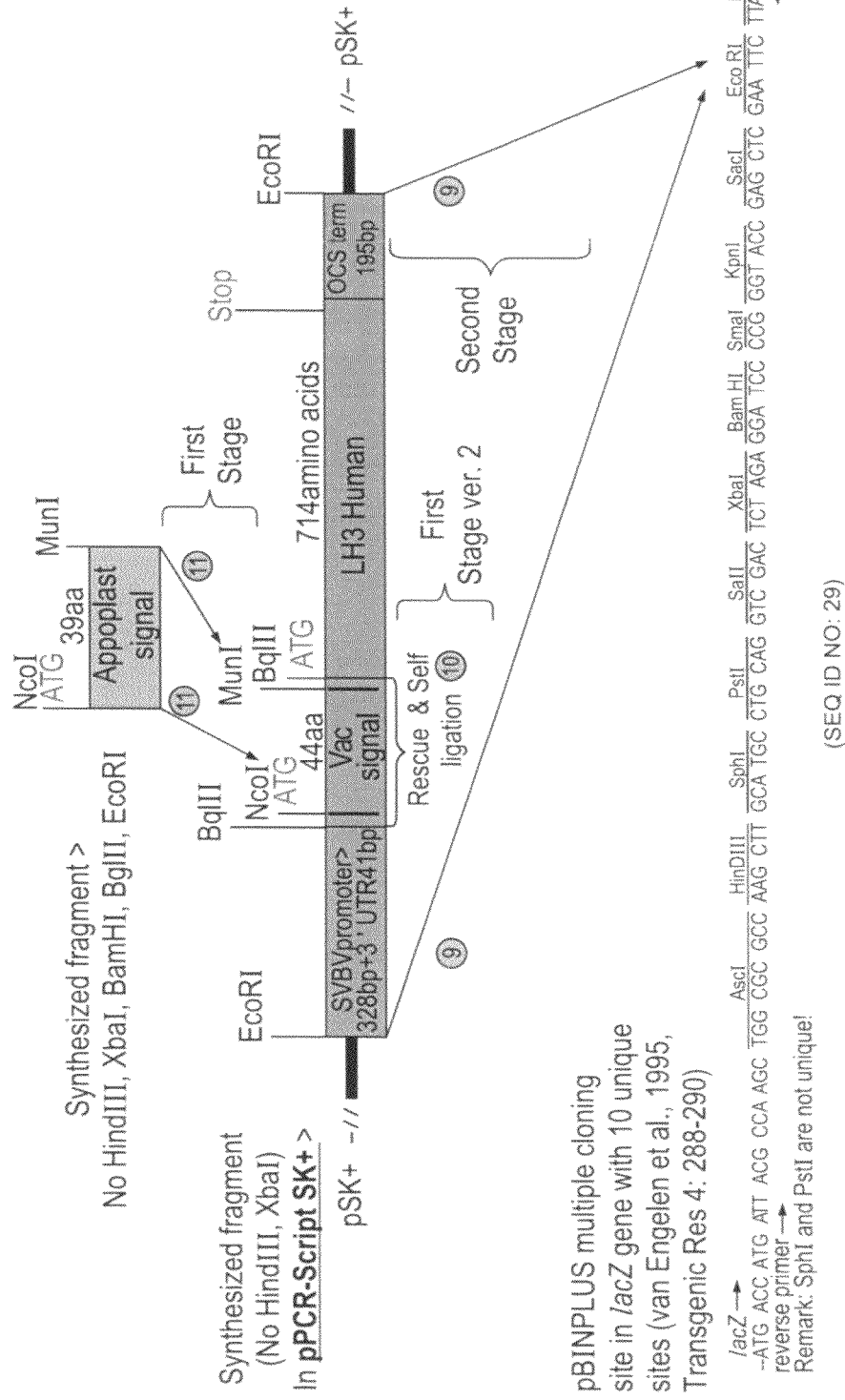

Constructions of expression cassettes and vectors used in this work are illustrated in FIG. 1a-d. All of the coding sequences in this work were optimized for expression in tobacco and chemically synthesized with desired flanking regions (SEQ ID NOs: 1, 4, 7, 12, 14, 16, 18, 20, 22). FIG. 1a—the synthetic genes coding for Col1 and Col2 (SEQ ID's 1, 4) fused either to the vacuolar signal or to the apoplast signal (encoded by SEQ ID NO: 7) or without signals were cloned in expression cassettes composed of a Chrysanthemum rbcS1 promoter and 5' UTR (SEQ ID NO: 10) and a Chrysanthemum rbcS1 3'UTR and terminator (SEQ ID NO: 11). The complete expression cassettes were cloned in the multiple cloning site of the pBINPLUS plant transformation vector (van Engelen et al., 1995, Transgenic Res 4: 288-290). FIG. 1b—The synthetic genes coding for P4H beta-human, P4H alpha-human and P4H-plant (SEQ ID NOs: 12, 14 and 16) fused either to the vacuolar signal or to the apoplast signal (encoded by SEQ ID NO: 7) or without signals were cloned in expression cassettes composed of the CaMV 35S promoter and TMV omega sequence and *Agrobacterium* Nopaline synthetase (NOS) terminator carried by the vector pJD330 (Galili et al., 1987, Nucleic Acids Res 15: 3257-3273). The complete expression cassettes were cloned in the multiple cloning site of the pBINPLUS vectors carrying the expression cassettes of Col1 or Col2. FIG. 1c—The synthetic genes coding for Proteinase C and Proteinase N (SEQ ID NOs: 18, 20) fused either to the vacuolar signal or to the apoplast signal (encoded by SEQ ID NO: 7) were cloned in expression cassettes composed of a Chrysanthemum rbcS1 promoter and 5' UTR (SEQ ID NO: 10) and a Chrysanthemum rbcS1 3'UTR and terminator (SEQ ID NO: 11). The complete expression cassettes were cloned in the multiple cloning site of the pBINPLUS plant transformation vector. FIG. 1d—The synthetic gene coding for LH3 (SEQ ID NO: 22) with flanking Strawberry vein banding virus (SVBV) promoter (NCBI accession AF331666 REGION: 623.950 version AF331666.1 GI:13345788) and terminated by *Agrobacterium* octopin synthase (OCS) terminator (NCBI accession Z37515 REGION: 1344.1538 version Z37515.1 GI:886843) fused either to the vacuolar signal or to the apoplast signal (encoded by SEQ ID NO: 7) or without signals was cloned in the multiple cloning site of the pBINPLUS vector carrying the expression cassettes of Col1 and P4H beta.

Figure 2:
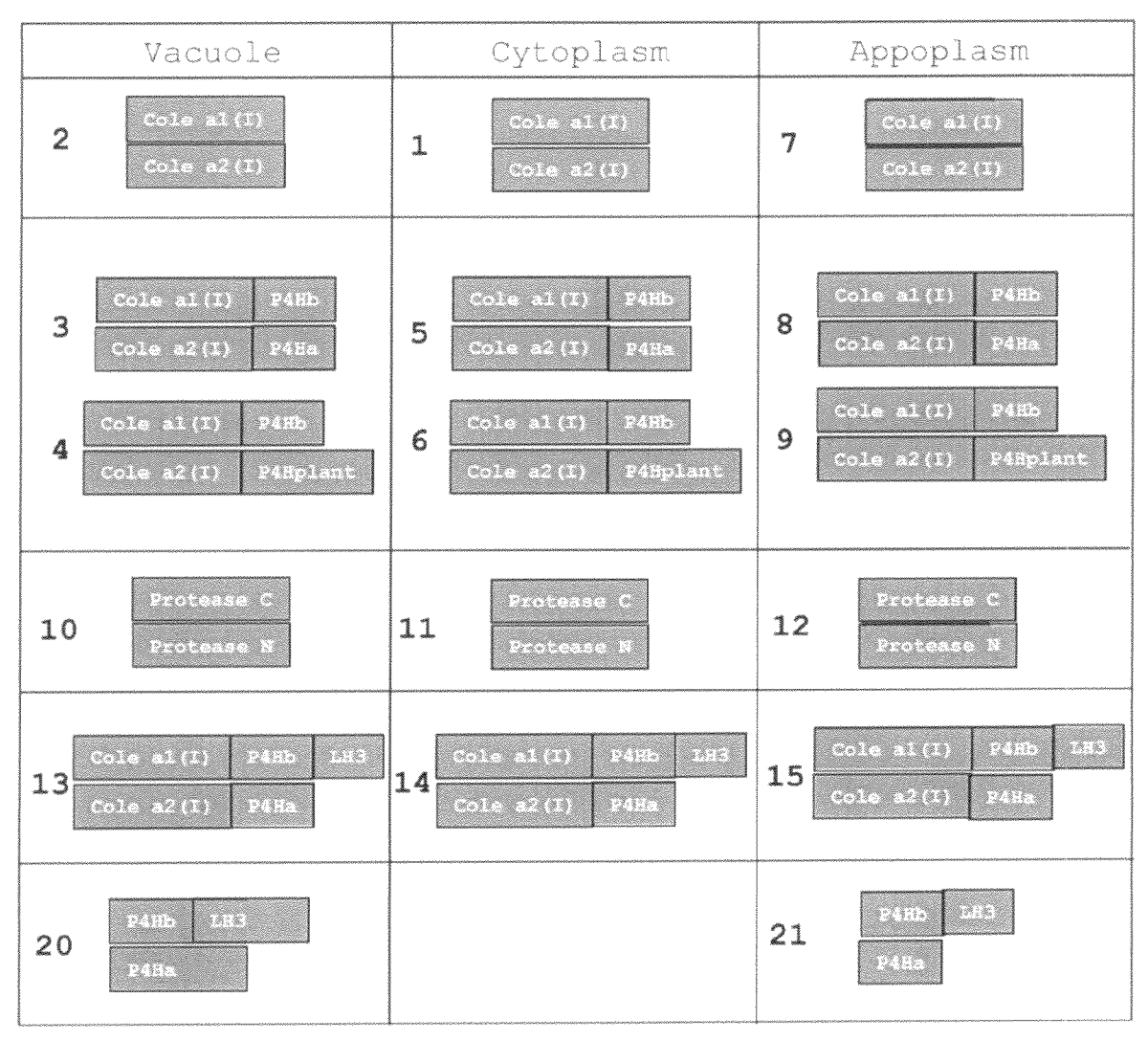

Co-transformations schemes utilizing the expression cassettes described in FIG. 1 into a host plant are illustrated in FIG. 2. Each expression cassette insert is represented by a short name of the coding sequence. The coding sequences and related SEQ ID NOs. are described in Table 1. Each co-transformation is preformed by two pBINPLUS binary vectors. Each rectangle represents a single pBINPLUS vector carrying one, two or three expression cassettes. Promoters and terminators are specified in FIG. 1.

Example 2

Plant Collagen Expression

Synthetic polynucleotide sequences encoding the proteins listed in Table 1 below were designed and optimized for expression in tobacco plants.

TABLE 1

List of expressed proteins

| Name: | SwissProt accession | Amino acids | Splicing isoform | Deletions | name | Included in SEQ ID NO. | Encoded by SEQ ID NO. |
|---|---|---|---|---|---|---|---|
| Collagen alpha 1(I) chain [Precursor] | p02452 | 1442 | One version | ER signal | Col1 | 3 | 1 |
| Collagen alpha 2(I) chain [Precursor] | p08123 Two changes done in p08123: D549A and N249I | 1342 | One version | ER signal | Col2 | 6 | 4 |
| Prolyl 4-hydroxylase beta subunit | p07237 | 487 | One version | ER signal, KDEL | P4H betaHuman | 13 | 12 |
| Prolyl 4-hydroxylase alpha-1 subunit | p13674 | 517 | P13674-1 | ER signal | P4H alphaHuman | 15 | 14 |
| Prolyl 4-hydroxylase Plant | No entry in Swissprot. NCBI accession: gi: 15227885 | 252 | One version | Mitochondrial signal predicted as: aa1-39 | P4Hplant | 17 | 16 |
| Procollagen C-proteinase | p13497 | 866 | P13497-1 BMP1-3 | ER signal, propeptide | Proteinase C | 19 | 18 |
| Procollagen I N-proteinase | o95450 | 958 | O95450-1 LpNPI | ER signal, propeptide | Proteinase N | 21 | 20 |
| Lysyl hydroxylase 3 | o60568 | 714 | One version | ER signal | LH3 | 23 | 22 |

Signal Peptides (i) Vacuole signal sequence of barley gene for Thiol protease aleurain precursor (NCBI accession P05167 GI:113603) MAHARVLLLALAVLATAAVAVASSSS-FADSNPIRPVTDRAASTLA (SEQ ID NO: 24).

(ii) Apoplast signal of *Arabidopsis thaliana* endo-1,4-beta-glucanase (Cell, NCBI accession CAA67156.1 GI:2440033); SEQ ID NO. 9, encoded by SEQ ID NO. 7.

Construction of Plasmids

Plant expression vectors were constructed as taught in Example 1, the composition of each constructed expression vector was confirmed via restriction analysis and sequencing.

Expression vectors including the following expression cassettes were constructed:
1. Collagen alpha 1
2. Collagen alpha 1+human P4H beta subunit
3. Collagen alpha 1+human P4H beta subunit+human LH3
4. Collagen alpha 2
5. Collagen alpha 2+with human P4H alpha subunit
6. Collagen alpha 2+with *Arabidopsis* P4H
7. Human P4H beta subunit+human LH3
8. Human P4H alpha subunit Each of the above described coding sequences was either translationally fused to a vacuole transit peptide or to an apoplasm transit peptide or was devoid of any transit peptide sequences, in which case cytoplasmic accumulation is expected.

Plant Transformation and PCR Screening

Tobacco plants (*Nicotiana tabacum*, Samsun NN) were transformed with the above described expression vectors according to the transformation scheme taught in FIG. 2.

Figure 3:
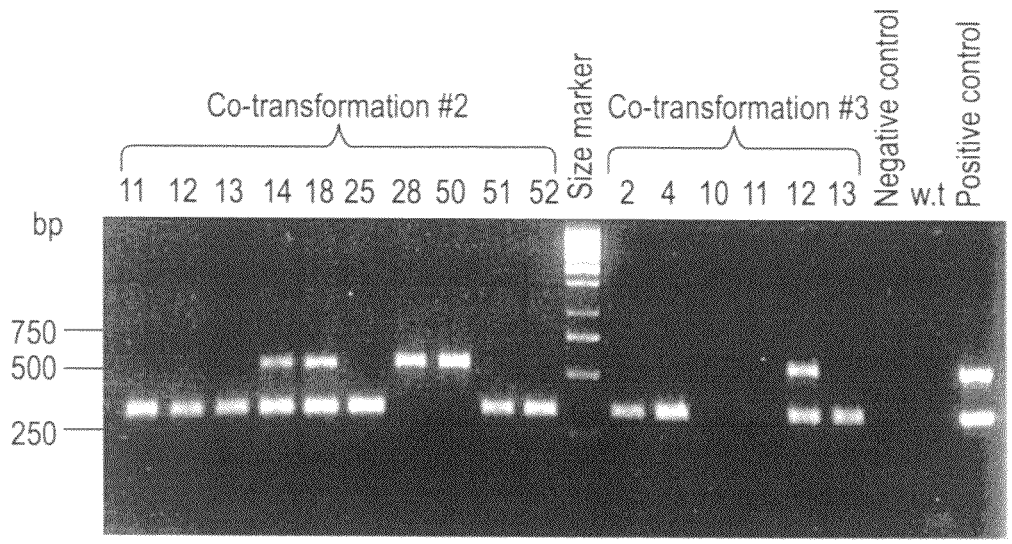
FIG. 3 is a multiplex PCR screening of transformants showing plants that are positive for Collagen alpha 1 (324 bp fragment) or Collagen alpha 2 (537 bp fragment) or both.

Resultant transgenic plants were screened via multiplex PCR using four primers which were designed capable of amplifying a 324 bp fragment of Collagen alpha 1 and a 537 bp fragment of Collagen alpha 2 (Table 2). FIG. 3 illustrates the results of one multiplex PCR screen.

TABLE 2

List of primers for multiplex PCR for amplification of a 324 bp fragment of Collagen alpha 1 and a 537 bp fragment of Collagen alpha 2

| Col1 forward primer (24-mer): | 5' ATCACCAGGAGAACAGGGACCATC 3' | SEQ ID 25 |
|---|---|---|
| Col1 reverse primer (29-mer): | 5' TCCACTTCCAAATCTCTATCCCTAACAA C 3' | SEQ ID 26 |
| Col2 forward primer (23-mer): | 5' AGGCATTAGAGGCGATAAGGGAG 3' | SEQ ID 27 |
| Col2 reverse primer (27-mer): | 5' TCAATCCAATAATAGCCACTTGACCAC 3' | SEQ ID 28 |

Example 3

Detection of Human Collagen in Transgenic Tobacco Plants

Figure 4:
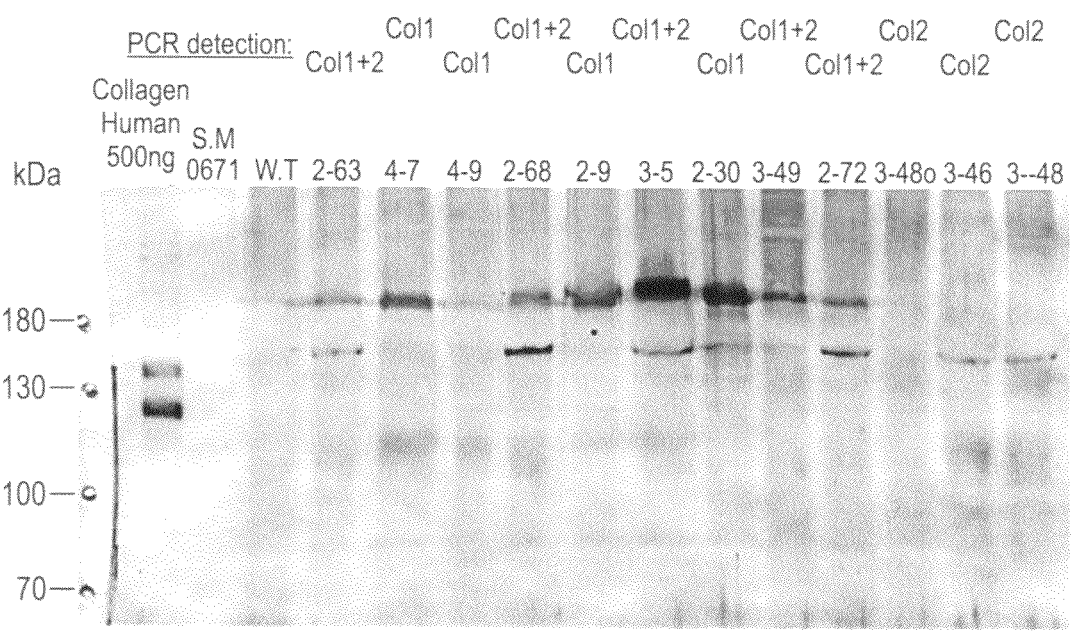
FIG. 4 is western blot analysis of transgenic plants generated by co-transformations 2, 3 and 4. Total soluble proteins were extracted from tobacco co-transformants #2, #3 and #4 and tested with anti-Collagen I antibody (#AB745 from Chemicon Inc.). Size markers were #SM0671 from Fermentas Inc. W.T. is a wild type tobacco. Positive collagen bands are visible in plants that are PCR positive for collagen typeI alpha 1 or alpha 2 or both. Positive control band of 500 ng collagen type I from human placenta (#CC050 from Chemicon Inc., extracted from human placenta by pepsin digestion) represents about 0.3% of the total soluble proteins (about 150 µg) in the samples from the transgenic plants. The larger band at about 140 kDa in the human collagen sample is a procollagen with it's C-propeptide as detected by anti carboxyterminal pro-peptide of collagen type I antibody (#MAB1913 from Chemicon Inc.). The smaller band at about 120 kDa in the human collagen sample is a collagen without propeptides. Due to their unusual composition proline rich proteins (including collagen)s consistently migrate on polyacrylamid gels as bands with molecular mass higher than expected. Therefore the collagen chains without propeptides with a molecular weight of about 95 kDa migrate as a band of about 120 kDa.

Total soluble proteins were extracted from tobacco transformants 2, 3 and 4 by grinding 500 mg of leaves in 0.5 ml 50 mM Tris-HCl pH=7.5 with a "Complete" protease inhibitor cocktail (product #1836145 from Roche Diagnostics GmbH, 1 tablet per 50 ml buffer). The crude extract was mixed with 250 µl 4× Sample application buffer containing 10% beta-mercapto-ethanol and 8% SDS, the samples were boiled for 7 minutes and centrifuged for 8 minutes in 13000 rpm. 20 µl of the supernatant were loaded in a 10% polyacrylamide gel and tested with anti-Collagen I (denatured) antibody ((#AB745 from Chemicon Inc.) in a standard Western blot procedure (FIG. 4). W.T. is a wild type tobacco. Positive collagen bands are visible in plants that are PCR positive for collagen typeI alpha 1 or alpha 2 or both. Positive control band of 500 ng collagen type I from human placenta (#CC050 from Chemicon Inc.) represents about 0.3% of the total soluble proteins (about 150 µg) in the samples from the transgenic plants.

Figure 5:
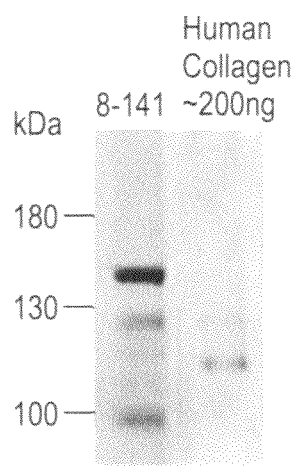
FIG. 5 is a western blot analysis of transgenic plant generated by co-transformation #8 (carrying apoplast signals translationally fused to the collagen chains). Total soluble proteins were extracted from transgenic tobacco leaves and tested with anti-Collagen I antibody (#AB745 from Chemicon Inc.) Positive collagen alpha 2 band is visible in plant 8-141. Collagen type I from human placenta (#CC050 from Chemicon Inc.) served as control.

Plants expressing collagen at the expected molecular weight up to ~1% of the total soluble proteins were detected when collagen was targeted to the vacuole (FIG. 4). Subcellular targeting of full length collagen to the apoplast was successfully achieved (FIG. 5). Plants expressing collagen in the cytoplasm (i.e. no targeting peptide) did not accumulate collagen to detectable levels showing that subcellular targeting of collagen in plants is critical for success.

In addition in contrast to the studies of Ruggiero et al. 2000 and Merle et al. 2002 which showed that collagen lacking the N-propeptide was subjected to significant proteolysis, using the present approach full length collagen proteins with C-propeptide and N-propeptide accumulated in subcellular compartments at high levels.

The present data also clearly shows that crossing two plants each expressing a different collagen chain type is advantageous in that it enables selection of plants expressing optimal levels of each chain type and subsequent plant crossing to achieve the desired collagen producing plant.

Collagen produced by the plants of the present invention includes the native propeptides and therefore is expected to form a larger protein then the human control that was purified by proteolysis. The calculated molecular weight of Collagen alpha 1 and alpha 2 chains without hydroxylations or glycosylations are the following: Col1 with propeptides—136 kDa, Col1 without propeptides—95 kDa, Col2 with propeptides—127 kDa, Col2 without propeptides—92 kDa.

As can be seen in FIG. 4, the Col1 bands in transformants 3-5 and 3-49 appears larger then Col1 bands in other plants. This indicates prolines hydroxylation in collagen chains by human proline-4-hydroxylase holoenzyme composed of alpha and beta subunits that were coexpressed in these plants and targeted to the same subcellular compartment as the human collagen chains (e.g. vacuole).

Example 4

Collagen Triple Helix Assembly and Thermal Stability in Transgenic Plants

Figure 6A:
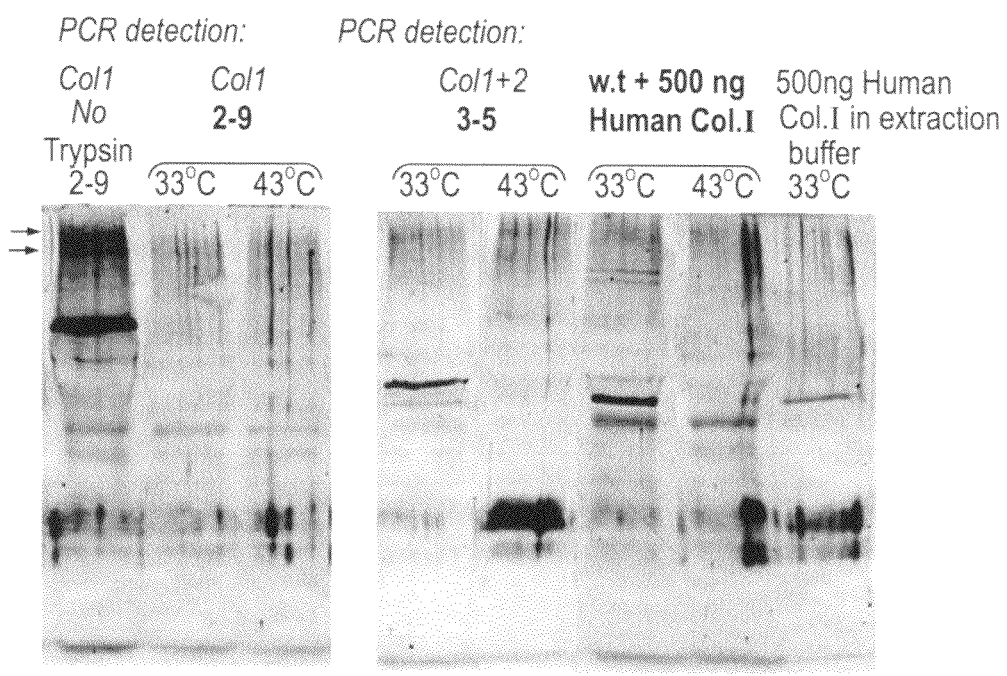
FIGS. 6a-b illustrate collagen triple helix assembly and thermal stability as qualified by heat treatment and Trypsin or Pepsin digestion.
Figure 6B:
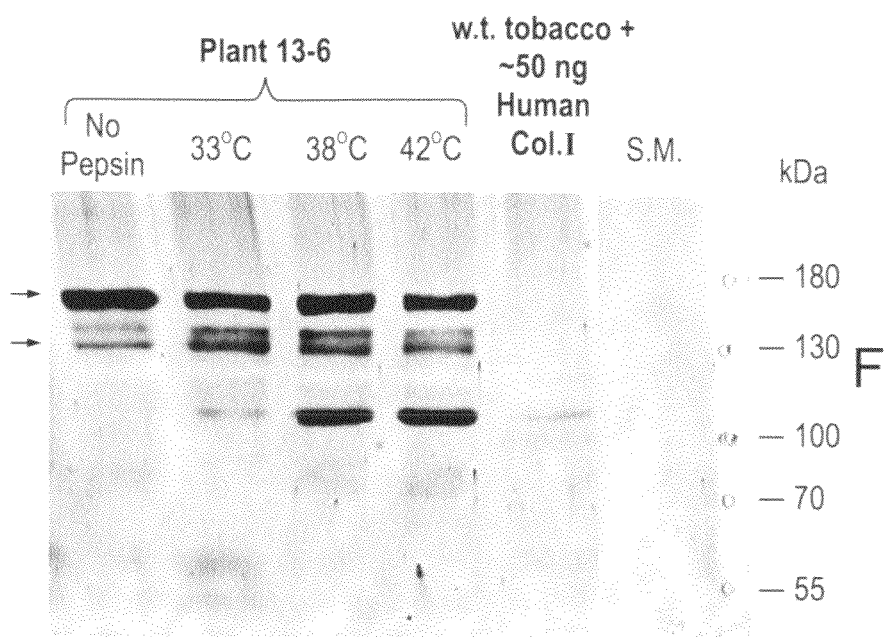

Assembly of collagen triple helix and the helix thermal stability in transgenic plants were tested by thermal denaturation followed by trypsin or pepsin digestion of the total crude protein extract of transgenic plants (FIGS. 6a-b).

In a first experiment, total soluble proteins from tobacco 2-9 (expressing only col alfa1 and no P4H) and 3-5 (expressing both col alfa1+2 and P4H) were extracted by grinding 500 mg leaves in 0.5 ml of 50 mM Tris-HCl pH=7.5, centrifuging for 10 minutes in 13000 rpm and collecting the supernatant. 0 µl of the supernatant were subjected to heat treatment (15 minutes in 33° C. or 43° C.) and then immediately placed on ice. Trypsin digestion was initiated by adding to each sample 6 µl of 1 mg/ml Trypsin in 50 mM Tris-HCl pH=7.5. The samples were incubated for 20 minutes at room temperature (about 22° C.). The digestion was terminated by addition of 20 µl 4× sample application buffer containing 10% betamercaptoethanol and 8% SDS, the samples were boiled for 7 minutes and centrifuged for 7 minutes at 13000 rpm. 50 µl of the supernatant were loaded onto a 10% polyacrylamide gel and tested with anti-Collagen I antibody ((#AB745 from Chemicon Inc.) using a standard Western blot procedure. Positive controls were samples of 500 ng human collagen I (#CC050 from Chemicon Inc., extracted from human placenta by pepsin digestion) which was added to 50 µl total soluble proteins extracted from w.t. tobacco.

As shown in FIG. 6a, collagen triple helix that formed in plants #3-5 as well as control human collagen was resistant to denaturation at 33° C. In contrast, collagen formed by plants #2-9 denatured at 33° C. This difference in thermal stability indicates a successful triple helix assembly and post translational proline hydroxylation in transformants #3-5 which express both collagen alpha 1 and collagen alpha 2 as well as P4H beta and alpha subunits.

Two bands in transformants #2-9 may represent dimers or trimers, which are stable following 7 minutes of boiling with SDS and mercaptoethanol. Similar bands are visible in human collagen (upper panel) and in transformants #3-5. A possible explanation is a covalent bond between two peptides in different triple helixes (cross link), formed following oxidative deamination of two lysines by Lysine oxidase.

In a second experiment, total soluble proteins from transgenic tobacco 13-6 (expressing collagen I alpha 1 and alpha 2 chains—pointed by arrows, human P4H alpha and beta subunits and human LH3) were extracted by grinding 500 mg of leaves in 0.5 ml of 100 mM Tris-HCl pH=7.5 and 300 mM NaCl, centrifuging for 7 minutes at 10000 rpm and collecting the supernatant. 50 µl of the supernatant was subjected to heat treatment (20 minutes in 33° C., 38° C. or 42° C.) and then immediately placed on ice. Pepsin digestion was initiated by adding to each sample 4.5 µl of 0.1M HCl and 4 µl of 2.5 mg/ml Pepsin in 10 mM acetic acid. The samples were incubated for 30 minutes at room temperature (about 22° C.). The digestion was terminated by adding 5 µl of unbuffered 1 M Tris. Each sample was mixed with 22 µl 4× Sample application buffer containing 10% beta-mercapto-ethanol and 8% SDS, boiled for 7 minutes and centrifuged for 7 minutes in 13000 rpm. 40 µl of the supernatant were loaded in a 10% polyacrylamide gel and tested with anti-Collagen I antibody ((#AB745 from Chemicon Inc.) in a standard Western blot procedure. Positive control was sample of ~50 ng human collagen I (#CC050 from Chemicon Inc., extracted from human placenta by pepsin digestion) added to total soluble proteins from w.t. tobacco.

As is illustrated in FIG. 6b, collagen triple helix that formed in plant #13-6 was resistant to denaturation at 42° C. Cleavage of the propetides is first visible at 33° C. and gradually increases in efficiency when the temperature is raised to 38° C. and again to 42° C. The cleaved collagen triple helix domain shows a similar migration on the gel to the migration of the pepsin treated human collagen. The human collagen that was used in this experiment was extracted from human placenta by pepsin proteolysis and therefore lacks the propeptides and some of the telopeptides.

Example 5

Plant P4H Expression

Induction of Native Plant P4H

Figure 7:
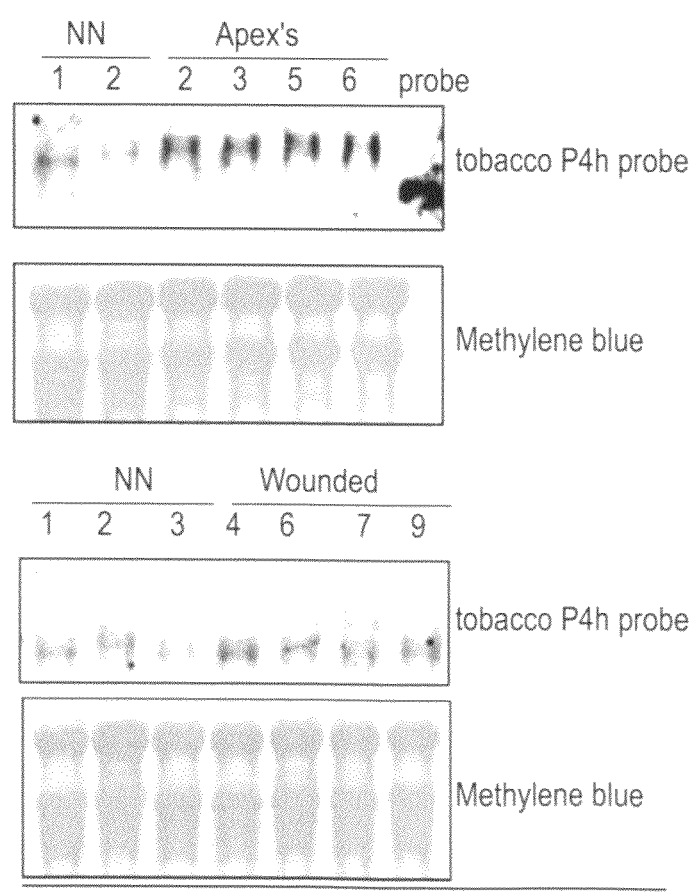
FIG. 7 illustrates Northern blot analysis conducted on wild type tobacco. Blots were probed with tobacco P4H cDNA.

Tobacco P4H cDNA was cloned and used as a probe to determine conditions and treatments that would induce endogenous P4H expression. Northern blot analysis (FIG. 7) clearly shows that P4H is expressed at relatively high levels in the shoot apex and at low levels in leaves. P4H level was induced significantly in leaves 4 hours following abrasion treatment ("wounded" in the lower panel). Similar results were achieved using other stress conditions (not shown).

Figure 8:
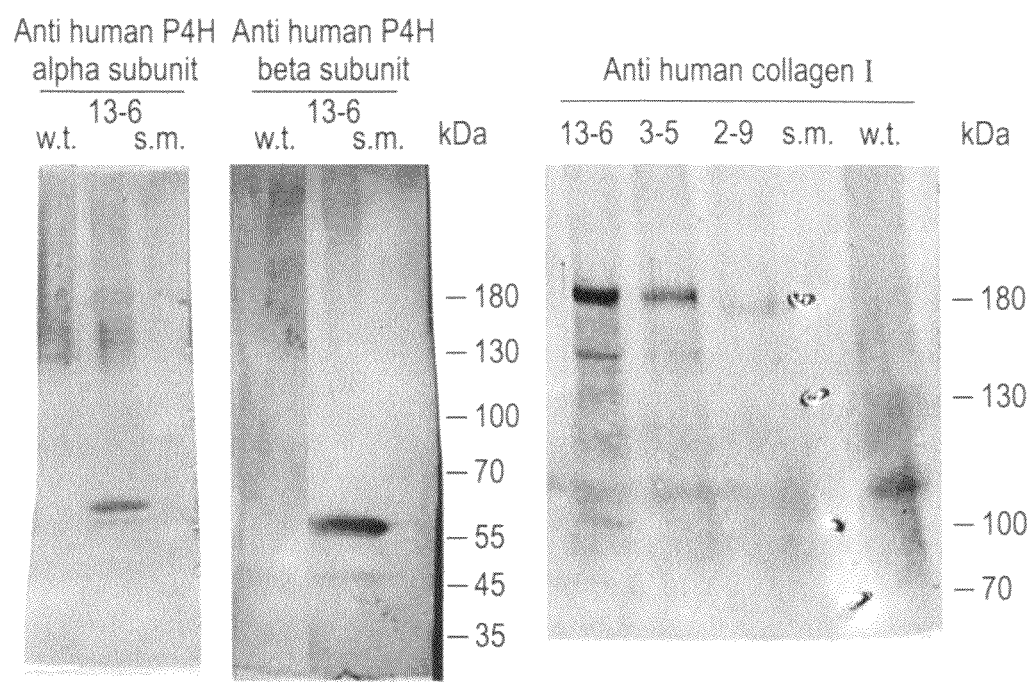
FIG. 8 is a western blot analysis of transgenic plants generated by co-transformations 2, 3 and 13. Total soluble protein was extracted from tobacco co-transformants and tested with anti human P4H alpha and beta and anti-Collagen I antibodies.

Detection of Human P4H Alpha and Beta Subunits and Collagen Alpha 1 and Alpha 2 Chains in Transgenic Tobacco Plants Detection of human P4H alpha and beta subunits and collagen type I alpha 1 and alpha 2 chains in transgenic tobacco plants was effected using anti-human P4H alpha subunit antibody (#63-163 from ICN Biomedicals Inc.), anti-human P4H beta subunit antibody (#NMAB2701 from Chemicon Inc.) and anti-Collagen I antibody (#AB745 from Chemicon Inc.). The results of a western blot probed with these antibodies are shown in FIG. 8.

Expression of P4H alpha, P4H beta and collagen 1 alpha 1 and alpha 2 bands was confirmed in plant 13-6 (also transformed also with human LH3). The calculated molecular weights of P4H alpha and beta including the vacuolar signal peptide are 65.5 kDa and 53.4 kDa respectively. The calculated molecular weights of Collagen alpha 1 and alpha 2 chains with propeptides, without hydroxylations or glycosylations are 136 kDa and 127 kDa respectively.

Example 6

Vacuolar Targeted Collagen is Stably Expressed in Dark-Grown Plants

Collagen Expressing Plants—

The 20-279 parental tobacco plant line was generated by co-transformation with an expression vector expressing P4Hbeta+LH3 and another expression vector expressing P4Halpha. Each gene is preceded by a vacuolar targeting determinant of aleurain, a plant vacuolar thiol protease, The 2-300 parental tobacco plant line was generated by co-transformation with an expression vector expressing col1 and another expression vector expressing col2. Each gene is preceded by a vacuolar targeting determinant of aleurain, a plant vacuolar thiol protease.

The 13-652 plant was generated by co-transformation of tobacco plant with an expression vector encoding Col1, P4Hbeta and LH3 and a second expression vector encoding Col2 and P4H alpha. Each gene is preceded by a vacuolar targeting determinant of aleurain, a plant vacuolar thiol protease, Cassete sequences included in the vectors are described in Example 1 above.

Light and Darkness Trial—

Analysis of six 13-6/52 homozygote plants. Samples from leaf #4+5/6 were taken daily at the same time (12:30) for 8 days, from 3 plants that were grown at regular conditions (16 hours under light conditions and 8 hours in the dark) and from 3 plants that were grown only in the dark.

Total Protein Extraction and Western Blot Analysis—

Ninety mg of tobacco leaves were homogenized by mixer mill Type MM301 (Retsch) in an extraction buffer (100 mM Tris HCl pH=7.5, protease inhibitor cocktail available from Roche Catalog Number, 04-693-116-001) at 4° C. Following 30 min of centrifugation (20,000×g at 4° C.), the supernatant was collected. Protein samples were fractionated on 8% SDS-PAGE (Laemmli 1970) and transferred to a nitrocellulose membrane using BIO-RAD™ Protein TRANS-BLOT™ apparatus. The membrane was blocked for 30 min at room temperature in 3% (g/v) skim milk (Difco), and then reacted with either commercial rabbit anti-human collagen type I polyclonal antibodies (Chemicon), for over night (o.n.) at room temperature. The membrane was rinsed with water 3-5 times and then washed for 30 min in TBS. Following incubation with a secondary antibody [goat anti rabbit-IgG antibody conjugated to alkaline phosphatase (chemicon)] for 2 hours at room temperature, the membrane was rinsed with water for 3-5 times and washed for 30 min in TBS. Immunodetection was effected with nitrotetrazolium blue chloride (NBT, Sigma) and 5-bromo-4-chloro-3-indolyl phosphate p-toluidine salt (BCIP, Sigma), at room temperature for 2 hour-o.n.

Results

Figure 9:
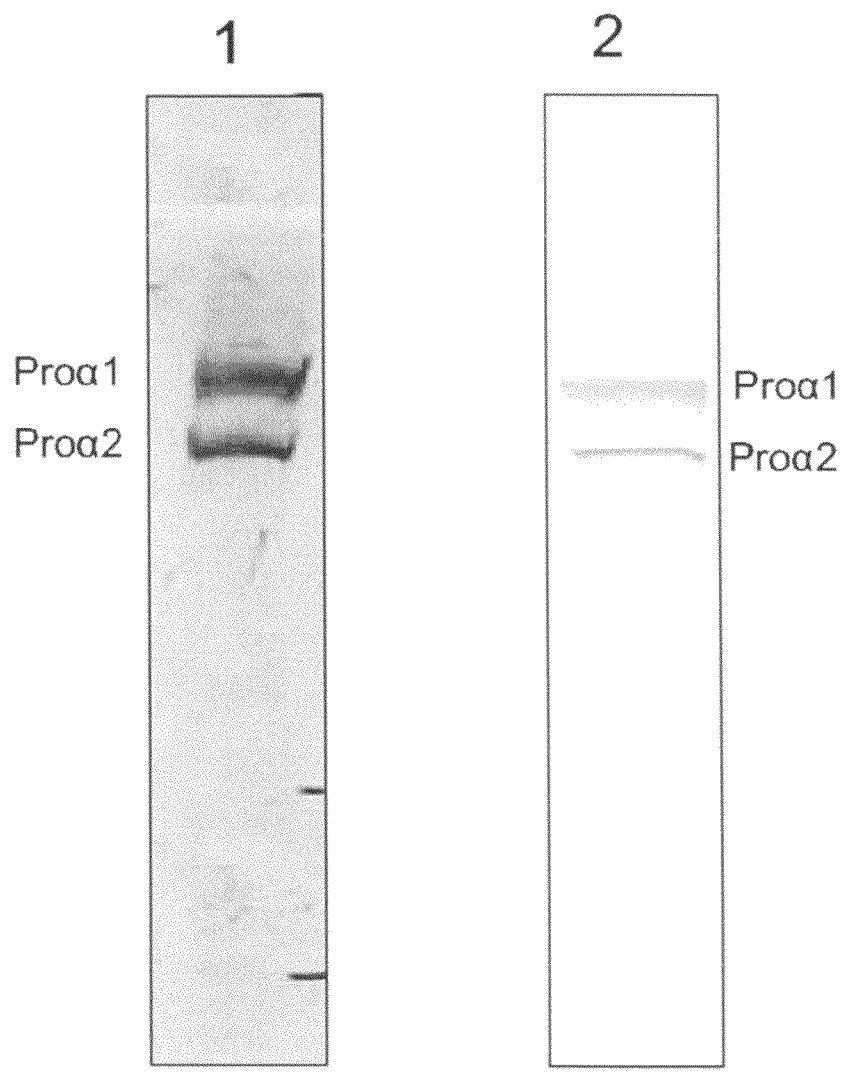
FIG. 9 is a western blot analysis of (lane 1) cross breeding vacuolar targeted plants A(2-300♀+20-279♂) grown under normal light regimen; and 13-652 vacuolar targeted plants grown for 8 days in the dark. All plants express exogenous col1, col2, P4H α and β as well as LH3 (PCR validated).

As shown in FIG. 9, tobacco plants transgenic for vacuolar targeted collagen express Proα1 and Proα2 (lane 1). Collagen from dark grown vacuolar targeted plants exhibited similar stability (lane 2), substantiating the exceptional stability of collagen generated according to the teachings of the present invention It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Other References are Cited in the Document

1. Bulleid N J, John D C, Kadler K E. Recombinant expression systems for the production of collagen. Biochem Soc Trans. 2000; 28(4):350-3. Review. PMID: 10961917 [PubMed—indexed for MEDLINE]
2. Hare P D, Cress W A. Metabolic implications of stress-induced proline accumulation in plants. Plant Growth Regulation 1997; 21: 79-102.
3. Hieta R, Myllyharju J. Cloning and characterization of a low molecular weight prolyl 4-hydroxylase from *Arabidopsis thaliana*. Effective hydroxylation of proline-rich, collagen-like, and hypoxia-inducible transcription factor alpha-like peptides. J Biol. Chem. 2002 Jun. 28; 277(26): 23965-71. Epub 2002 Apr. 25. PMID: 11976332 [PubMed—indexed for MEDLINE]

4. Hulmes D J. Building collagen molecules, fibrils, and suprafibrillar structures. J Struct Biol. 2002 January-February; 137(1-2):2-10. Review. PMID: 12064927 [PubMed—indexed for MEDLINE]
5. Inkinen K. Connective tissue formation in wound healing. An experimental study. Academic Dissertation, September 2003. University of Helsinki, Faculty of Science, Department of Biosciences, Division of Biochemistry (ISBN 952-10-1313-3) http://ethesis.helsinki.fi/iulkaisut/mat/bioti/vk/inkinen/
6. Merle C, Perret S, Lacour T, Jonval V, Hudaverdian S, Garrone R, Ruggiero F, Theisen M. Hydroxylated human homotrimeric collagen I in *Agrobacterium tumefaciens*-mediated transient expression and in transgenic tobacco plant. FEBS Lett. 2002 Mar. 27; 515(1-3):114-8. PMID: 11943205 [PubMed—indexed for MEDLINE]
7. Olsen D, Yang C, Bodo M, Chang R, Leigh S, Baez J, Carmichael D, Perala M, Hamalainen E R, Jarvinen M, Polarek J. Recombinant collagen and gelatin for drug delivery. Adv Drug Deliv Rev. 2003 Nov. 28; 55(12):1547-67. PMID: 14623401 [PubMed—in process]
8. Ruggiero F, Exposito J Y, Bournat P, Gruber V, Perret S, Comte J, Olagnier B, Garrone R, Theisen M. Triple helix assembly and processing of human collagen produced in transgenic tobacco plants. FEBS Lett. 2000 Mar. 3; 469(1): 132-6. PMID: 10708770 [PubMed—indexed for MEDLINE]
9. Tanaka M, Sato K, Uchida T. Plant prolyl hydroxylase recognizes poly(L-proline) II helix. J Biol. Chem. 1981 Nov. 25; 256(22):11397-400. PMID: 6271746 [PubMed—indexed for MEDLINE]
10. Wang C, Luosujarvi H, Heikkinen J, Risteli M, Uitto L, Myllyla R. The third activity for lysyl hydroxylase 3: galactosylation of hydroxylysyl residues in collagens in vitro. Matrix Biol. 2002 November; 21(7):559-66. PMID: 12475640 [PubMed—indexed for MEDLINE]

What is claimed is:

1. A method of producing collagen in a plant or an isolated plant cell comprising targeting to a vacuole of the plant or the isolated plant cell the collagen alpha 1 chain as set forth in SEQ ID NO: 3 and an exogenous prolyl-4-hydroxylase (P4H) so as to allow hydroxylation of the collagen alpha 1 chain by said exogenous P4H, thereby producing the collagen in the plant.

2. The method of claim 1, further comprising expressing an exogenous polypeptide selected from the group consisting of Lysyl hydroxylase (LH), protease N and protease C—.

3. The method of claim 1, wherein said exogenous P4H comprises a mammalian P4H.

4. The method of claim 1, wherein the plant is selected from the group consisting of Tobacco, Maize, Alfalfa, Rice, Potato, Soybean, Tomato, Wheat, Barley, Canola, Carrot and Cotton.

5. The method of claim 1, wherein said exogenous P4H is capable of specifically hydroxylating the Y position of Gly-X-Y triplets of said at least one type of said collagen chain.

6. The method of claim 3, wherein said mammalian P4H comprises a human P4H.

7. The method of claim 1, wherein the plant is subjected to a stress condition.

8. The method of claim 7, wherein said stress condition is selected from the group consisting of drought, salinity, injury, cold and spraying with stress inducing compounds.

9. A method of producing collagen, said method comprising:
    (a) providing a plant system comprising:
        a first genetically modified plant comprising in a vacuole thereof.
            (i) the collagen alpha 1 chain as set forth in SEQ ID NO: 3; and
            (ii) an exogenous P4H; and
        a second genetically modified plant comprising in a vacuole thereof:
            (i) the collagen alpha 2 chain as set forth in SEQ ID NO: 6; and
            (ii) an exogenous P4H;
    (b) crossing said first plant and said second plant; and
    (c) selecting progeny expressing said collagen alpha 1 chain and said collagen alpha 2 chain thereby producing collagen.

10. The method of claim 9, wherein said exogenous P4H is capable of specifically hydroxylating the Y position of Gly-X-Y triplets of said collagen alpha 1 chain or collagen alpha 2 chain.

11. The method of claim 9, wherein said exogenous P4H is human P4H.

12. A method of producing collagen comprising:
    (a) providing the plant system comprising:
        a first genetically modified plant comprising in a vacuole thereof:
            (i) the collagen alpha 1 chain as set forth in SEQ ID NO: 3; and
            (ii) the collagen alpha 2 chain as set forth in SEQ ID NO: 6; and
        a second genetically modified plant comprising in a vacuole thereof an exogenous P4H; and
    (b) crossing said first plant and said second plant and selecting progeny expressing the collagen alpha 1 chain, the collagen alpha 2 chain and said P4H thereby producing collagen.

13. The method of claim 1, wherein the collagen alpha 1 chain is encoded by a sequence as set forth in SEQ ID NO: 1.

14. The method of claim 1, further comprising targeting to a vacuole of the plant or the isolated plant cell the collagen alpha 2 chain as set forth in SEQ ID NO: 6 so as to allow hydroxylation of the collagen alpha 2 chain by said exogenous P4H.

15. The method of claim 1, further comprising isolating the collagen following the producing.

* * * * *

SEQUENCE LISTING

```
<160> NUMBER OF SEQ ID NOS: 29

<210> SEQ ID NO 1
<211> LENGTH: 4662
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Collagen alpha 1(I)
      chain and flanking regions

<400> SEQUENCE: 1
gcgatgcatg taatgtcatg agccacatga tccaatggcc acaggaacgt aagaatgtag      60
atagatttga ttttgtccgt tagatagcaa acaacattat aaaaggtgtg tatcaatacg     120
aactaattca ctcattggat tcatagaagt ccattcctcc taagtatcta aaccatggct     180
cacgctcgtg ttctcctcct cgctctcgct gttttggcaa cagctgctgt ggctgtggct     240
tctagttctt cttttgctga ttcaaaccct attagacctg ttactgatag agcagcttcc     300
actttggctc aattgcaaga ggagggccag gttgagggcc aagatgagga tatccctcca     360
attacatgcg tgcaaaatgg cttgcgttac cacgataggg atgtgtggaa acctgaacct     420
tgtcgtatct gtgtgtgtga taacggcaag gtgctctgcg atgatgttat ctgcgatgag     480
acaaaaaatt gccctggcgc tgaagttcct gagggcgagt gttgccctgt gtgccctgat     540
ggttccgagt ccccaactga tcaggaaact actggcgtgg agggcccaaa aggagatact     600
ggtccacgtg gtcctagggg tccagcaggt cctccaggta gagatggtat tccaggccag     660
cctggattgc caggaccacc aggcccacct ggcccaccag gacctcctgg tcttggtgga     720
aatttcgctc cacaactctc ttatggctat gatgagaagt caacaggtgg tatttccgtt     780
ccaggtccta tgggaccatc cggaccaaga ggtctcccag gtcctccagg tgctcctgga     840
cctcaaggct ttcaaggacc tccaggcgaa ccaggagaac caggcgcttc tggaccaatg     900
ggcccaaggg gaccacctgg cccaccagga aaaaatggcg atgatggcga agctggaaag     960
cctggtcgtc ctggagagag aggtcctcct ggcccacagg gtgcaagagg cttgccagga    1020
actgctggct gcctggaat gaagggacat aggggcttct ccggcctcga tggcgctaag    1080
ggtgatgctg gcctgctgg accaaggggc gagccaggtt ccctggaga aaacggtgct    1140 cctggacaaa tgggtcctcg tggacttcca ggagaaaggg gtcgtccagg cgctccagga    1200
```

```
ccagcaggtg ctaggggaaa cgatggtgca acaggcgctg ctggccctcc tggcccaact   1260
ggtcctgctg gccctccagg attcccaggc gcagttggag ctaaaggaga agcaggacca   1320
cagggcccta ggggttctga aggacctcag ggtgttagag gtgaaccagg tcctccaggc   1380
ccagctggag cagctggtcc agcaggaaat ccaggtgctg atggtcaacc tggagctaag   1440
ggcgctaatg gcgcaccagg tatcgcaggc gcaccaggtt ttcctggcgc tagaggccca   1500
agtggtcctc aaggaccagg tggaccacca ggtccaaaag gcaattctgg cgaacctggc   1560
gctccaggtt ctaaaggaga tactggtgct aaaggcgaac caggacctgt tggtgttcag   1620
ggtcctcctg gtcctgctgg agaagaagga aaaagaggtg ctcgtggaga accaggacca   1680
actggacttc ctggacctcc tggtgaacgt ggcggacctg gctcaagggg tttccctgga   1740
gctgatggag tggcaggtcc aaaaggcccc tgctggagaga gaggttcacc aggtccagct   1800
ggtcctaagg gctcccctgg tgaagcaggt agaccaggcg aagcaggatt gccaggcgca   1860
aagggattga caggctctcc tggtagtcct ggcccagatg gaaaaacagg cccaccaggt   1920
ccagcaggac aagatggacg tccaggccca ccaggtcctc ctggagcaag gggacaagct   1980
ggcgttatgg gttttccagg acctaaaggt gctgctggag agccaggaaa ggcaggtgaa   2040
agaggagttc ctggtccacc aggagcagtg ggtcctgctg gcaaagatgg tgaagctgga   2100
gcacagggcc ctccaggccc tgctggccca gctggcgaac gtggagaaca aggcccagct   2160
ggtagtccag gatttcaagg attgcctggc cctgctggcc ctccaggaga agcaggaaaa   2220
cctggagaac aaggagttcc tggtgatttg ggagcacctg gaccttcagg agcacgtggt   2280
gaaagaggct cccctggcga gagggtgttt caaggtccac caggtccagc aggacctaga   2340
ggtgctaatg gcgctcctgg caacgatgga gcaaaaggtg atgctggtgc tcctggcgca   2400
cctggaagtc agggtgctcc tggattgcaa ggaatgcctg agagaggggg tgctgctggc   2460
ttgccaggcc caagggcga tagggtgat gctggaccaa aggtgctga tggatcccca   2520
ggaaaagatg gagttcgtgg tcttactggc ccaatcggac ctccaggccc tgctggcgct   2580
ccaggtgata agggcgaaag tggcccaagt ggacctgctg gacctactgg tgctagaggt   2640
gcacctggtg atagggtgga acctggacca cctggtccag ctggttttgc tggtcctcct   2700
ggagctgatg gacaacctgg cgcaaagggt gaaccaggtg atgctggcgc aaagggagat   2760
gctggtccac ctgggacctgc tggtccagca ggcccccctg gccaatcgg taatgttgga   2820
gcaccaggtg ctaagggagc tagggggttcc gctggtccac ctggagcaac aggatttcca   2880
ggcgctgctg gtagagttgg cccaccaggc ccatccggaa acgcaggccc tcctggtcct   2940
ccaggtcctg ctggcaagga gggtggcaaa ggaccaaggg gcgaaactgg ccctgctggt   3000
agacctggcg aagttggccc tcctggacca ccagtccag caggagaaaa aggttcccca   3060
ggagctgatg gcccagctgg tgctccagga actccaggcc ctcaaggtat gctggacag   3120
agaggcgttg tgggactccc tggtcaaagg ggagagagag gatttccagg cttgccagga   3180
cctagtggag aacctggaaa acaaggccca tcaggcgcta gtggagagcg tggacctcct   3240
ggccctatgg gacctcctgg attgctggc ccacctggcg aatcaggtcg tgaaggcgca   3300
ccaggcgcag aaggatcacc tggaagagat ggatccctg gtgctaaagg cgatcgtgga   3360
gaaactggtc cagcaggccc accagccgca ccaggtgcac ctggcgctcc aggacctgtg   3420
ggaccagctg gaaaatccgg agataggggc gagacaggcc cagcaggacc agctggacct   3480
gttggccctg ctgcgctcg tggaccagca ggacctcaag gaccagggg agataaggga   3540
gaaacaggcg aacaaggcga tagggcatt aagggtcata ggggttttag tggcctccag   3600
```

```
ggtcctcctg gcccacctgg atcaccagga gaacagggac catctggtgc ttccggccca    3660
gctggtccaa gaggacctcc aggatcagct ggtgcacctg gaaaagatgg tcttaacggt    3720
ctcccaggac caatcggccc tccaggacct agaggaagaa caggagatgc tggccctgtt    3780
ggccctccag gacctcctgg tccaccaggt ccacctggtc ctccatcagc tggattcgat    3840
ttttcatttc ttccacagcc accacaagag aaagctcacg atggcggcag atattaccgt    3900
gctgatgatg ctaacgttgt tagggataga gatttggaag tggatacaac tttgaaatcc    3960
ctctcccagc aaattgaaaa cattagatct ccagaaggtt cacgtaaaaa cccagctaga    4020
acatgtcgtg atttgaaaat gtgtcactcc gattggaaaa gtggtgaata ctggattgat    4080
ccaaatcagg gctgtaatct cgatgctatc aaagttttct gtaacatgga aacaggcgaa    4140
acatgcgttt atcctactca accttccgtg gctcagaaaa attggtacat ctcaaaaaat    4200
cctaaagata agaggcacgt ttggttcggt gaaagtatga ctgatggatt tcaatttgag    4260
tacgccggtc aaggtagtga tccagctgat gtggctattc aactcacatt tttgcgtctt    4320
atgtccacag aggcatcaca aaacatcact taccactgca aaaacagtgt ggcttatatg    4380
gatcaacaaa caggaaacct taagaaggct cttcttttga agggctcaaa cgagattgag    4440
attagagcag agggcaactc aaggtttact tattcagtta ctgttgatgg ctgcacttca    4500
catactggcg cttggggtaa aacagttatc gagtataaga ctacaaaaac atcaagactc    4560
ccaatcattg atgttgctcc tctcgatgtt ggcgctcctg atcaagagtt cggttttgat    4620
gtgggcccag tttgtttcct ctaatgagct cgcggccgca tc                       4662

<210> SEQ ID NO 2
<211> LENGTH: 4662
<212> TYPE: DNA
<213> ORGANISM: Artificial sequence
<220> FEATURE:
<223> OTHER INFORMATION: Synthetic sequence of the vacuolar signal
      sequence of barley gene for Thiol protease aleurain precursor
      fused to the human Collagen alpha 1(I) chain and flanking regions
<220> FEATURE:
<221> NAME/KEY: CDS
<222> LOCATION: (175)..(4644)

<400> SEQUENCE: 2
gcgatgcatg taatgtcatg agccacatga tccaatggcc acaggaacgt aagaatgtag    60
atagatttga ttttgtccgt tagatagcaa acaacattat aaaaggtgtg tatcaatacg    120
aactaattca ctcattggat tcatagaagt ccattcctcc taagtatcta aacc atg     177
                                                             Met
                                                             1 gct cac gct cgt gtt ctc ctc ctc gct ctc gct gtt ttg gca aca gct    225
Ala His Ala Arg Val Leu Leu Leu Ala Leu Ala Val Leu Ala Thr Ala
           5                  10                  15 gct gtg gct gtg gct tct agt tct tct ttt gct gat tca aac cct att    273
Ala Val Ala Val Ala Ser Ser Ser Ser Phe Ala Asp Ser Asn Pro Ile
       20                  25                  30 aga cct gtt act gat aga gca gct tcc act ttg gct caa ttg caa gag    321
Arg Pro Val Thr Asp Arg Ala Ala Ser Thr Leu Ala Gln Leu Gln Glu
   35                  40                  45 gag ggc cag gtt gag ggc caa gat gag gat atc cct cca att aca tgc    369
Glu Gly Gln Val Glu Gly Gln Asp Glu Asp Ile Pro Pro Ile Thr Cys
50                  55                  60                  65 gtg caa aat ggc ttg cgt tac cac gat agg gat gtg tgg aaa cct gaa    417
Val Gln Asn Gly Leu Arg Tyr His Asp Arg Asp Val Trp Lys Pro Glu
               70                  75                  80 cct tgt cgt atc tgt gtg tgt gat aac ggc aag gtg ctc tgc gat gat    465
```

```
                Pro Cys Arg Ile Cys Val Cys Asp Asn Gly Lys Val Leu Cys Asp Asp
                            85                  90                  95 gtt atc tgc gat gag aca aaa aat tgc cct ggc gct gaa gtt cct gag        513
Val Ile Cys Asp Glu Thr Lys Asn Cys Pro Gly Ala Glu Val Pro Glu
            100                 105                 110 ggc gag tgt tgc cct gtg tgc cct gat ggt tcc gag tcc cca act gat        561
Gly Glu Cys Cys Pro Val Cys Pro Asp Gly Ser Glu Ser Pro Thr Asp
        115                 120                 125 cag gaa act act ggc gtg gag ggc cca aaa gga gat act ggt cca cgt        609
Gln Glu Thr Thr Gly Val Glu Gly Pro Lys Gly Asp Thr Gly Pro Arg
130                 135                 140                 145 ggt cct agg ggt cca gca ggt cct cca ggt aga gat ggt att cca ggc        657
Gly Pro Arg Gly Pro Ala Gly Pro Pro Gly Arg Asp Gly Ile Pro Gly
                150                 155                 160 cag cct gga ttg cca gga cca cca ggc cca cct ggc cca cca gga cct        705
Gln Pro Gly Leu Pro Gly Pro Pro Gly Pro Pro Gly Pro Pro Gly Pro
            165                 170                 175 cct ggt ctt ggt gga aat ttc gct cca caa ctc tct tat ggc tat gat        753
Pro Gly Leu Gly Gly Asn Phe Ala Pro Gln Leu Ser Tyr Gly Tyr Asp
        180                 185                 190 gag aag tca aca ggt ggt att tcc gtt cca ggt cct atg gga cca tcc        801
Glu Lys Ser Thr Gly Gly Ile Ser Val Pro Gly Pro Met Gly Pro Ser
    195                 200                 205 gga cca aga ggt ctc cca ggt cct cca ggt gct cct gga cct caa ggc        849
Gly Pro Arg Gly Leu Pro Gly Pro Pro Gly Ala Pro Gly Pro Gln Gly
210                 215                 220                 225 ttt caa gga cct cca ggc gaa cca gga gaa cca ggc gct tct gga cca        897
Phe Gln Gly Pro Pro Gly Glu Pro Gly Glu Pro Gly Ala Ser Gly Pro
                230                 235                 240 atg ggc cca agg gga cca cct ggc cca cca gga aaa aat ggc gat gat        945
Met Gly Pro Arg Gly Pro Pro Gly Pro Pro Gly Lys Asn Gly Asp Asp
            245                 250                 255 ggc gaa gct gga aag cct ggt cgt cct gga gag aga ggt cct cct ggc        993
Gly Glu Ala Gly Lys Pro Gly Arg Pro Gly Glu Arg Gly Pro Pro Gly
        260                 265                 270 cca cag ggt gca aga ggc ttg cca gga act gct ggc ttg cct gga atg       1041
Pro Gln Gly Ala Arg Gly Leu Pro Gly Thr Ala Gly Leu Pro Gly Met
275                 280                 285 aag gga cat agg ggc ttc tcc ggc ctc gat ggc gct aag ggt gat gct       1089
Lys Gly His Arg Gly Phe Ser Gly Leu Asp Gly Ala Lys Gly Asp Ala
290                 295                 300                 305 ggc cct gct gga cca aag ggc gag cca ggt tcc cct gga gaa aac ggt       1137
Gly Pro Ala Gly Pro Lys Gly Glu Pro Gly Ser Pro Gly Glu Asn Gly
                310                 315                 320 gct cct gga caa atg ggt cct cgt gga ctt cca gga gaa agg ggt cgt       1185
Ala Pro Gly Gln Met Gly Pro Arg Gly Leu Pro Gly Glu Arg Gly Arg
            325                 330                 335 cca ggc gct cca gga cca gca ggt gct agg gga aac gat ggt gca aca       1233
Pro Gly Ala Pro Gly Pro Ala Gly Ala Arg Gly Asn Asp Gly Ala Thr
        340                 345                 350 ggc gct gct ggc cct cct ggc cca act ggt cct gct ggc cct cca gga       1281
Gly Ala Ala Gly Pro Pro Gly Pro Thr Gly Pro Ala Gly Pro Pro Gly
355                 360                 365 ttc cca ggc gca gtt gga gct aaa gga gaa gca gga cca cag ggc cct       1329
Phe Pro Gly Ala Val Gly Ala Lys Gly Glu Ala Gly Pro Gln Gly Pro
370                 375                 380                 385 agg ggt tct gaa gga cct cag ggt gtt aga ggt gaa cca ggt cct cca       1377
Arg Gly Ser Glu Gly Pro Gln Gly Val Arg Gly Glu Pro Gly Pro Pro
                390                 395                 400 ggc cca gct gga gca gct ggt cca gca gga aat cca ggt gct gat ggt       1425
Gly Pro Ala Gly Ala Ala Gly Pro Ala Gly Asn Pro Gly Ala Asp Gly
```

-continued

```
            Gly Pro Ala Gly Ala Ala Gly Pro Ala Gly Asn Pro Gly Ala Asp Gly
                            405                 410                 415 caa cct gga gct aag ggc gct aat ggc gca cca ggt atc gca ggc gca           1473
Gln Pro Gly Ala Lys Gly Ala Asn Gly Ala Pro Gly Ile Ala Gly Ala
420                 425                 430 cca ggt ttt cct ggc gct aga ggc cca agt ggt cct caa gga cca ggt           1521
Pro Gly Phe Pro Gly Ala Arg Gly Pro Ser Gly Pro Gln Gly Pro Gly
            435                 440                 445 gga cca cca ggt cca aaa ggc aat tct ggc gaa cct ggc gct cca ggt           1569
Gly Pro Pro Gly Pro Lys Gly Asn Ser Gly Glu Pro Gly Ala Pro Gly
450                 455                 460                 465 tct aaa gga gat act ggt gct aaa ggc gaa cca gga cct gtt ggt gtt           1617
Ser Lys Gly Asp Thr Gly Ala Lys Gly Glu Pro Gly Pro Val Gly Val
                470                 475                 480 cag ggt cct cct ggt cct gct gga gaa gaa gga aaa aga ggt gct cgt           1665
Gln Gly Pro Pro Gly Pro Ala Gly Glu Glu Gly Lys Arg Gly Ala Arg
            485                 490                 495 gga gaa cca gga cca act gga ctt cct gga cct cct ggt gaa cgt ggc           1713
Gly Glu Pro Gly Pro Thr Gly Leu Pro Gly Pro Pro Gly Glu Arg Gly
        500                 505                 510 gga cct ggc tca agg ggt ttc cct gga gct gat gga gtg gca ggt cca           1761
Gly Pro Gly Ser Arg Gly Phe Pro Gly Ala Asp Gly Val Ala Gly Pro
515                 520                 525 aaa ggc cct gct gga gag aga ggt tca cca ggt cca gct ggt cct aag           1809
Lys Gly Pro Ala Gly Glu Arg Gly Ser Pro Gly Pro Ala Gly Pro Lys
530                 535                 540                 545 ggc tcc cct ggt gaa gca ggt aga cca ggc gaa gca gga ttg cca ggc           1857
Gly Ser Pro Gly Glu Ala Gly Arg Pro Gly Glu Ala Gly Leu Pro Gly
                550                 555                 560 gca aag gga ttg aca ggc tct cct ggt agt cct ggc cca gat gga aaa           1905
Ala Lys Gly Leu Thr Gly Ser Pro Gly Ser Pro Gly Pro Asp Gly Lys
            565                 570                 575 aca ggc cca cca ggt cca gca gga caa gat gga cgt cca ggc cca cca           1953
Thr Gly Pro Pro Gly Pro Ala Gly Gln Asp Gly Arg Pro Gly Pro Pro
        580                 585                 590 ggt cct cct gga gca agg gga caa gct ggc gtt atg ggt ttt cca gga           2001
Gly Pro Pro Gly Ala Arg Gly Gln Ala Gly Val Met Gly Phe Pro Gly
595                 600                 605 cct aaa ggt gct gct gga gag cca gga aag gca ggt gaa aga gga gtt           2049
Pro Lys Gly Ala Ala Gly Glu Pro Gly Lys Ala Gly Glu Arg Gly Val
610                 615                 620                 625 cct ggt cca cca gga gca gtg ggt cct gct ggc aaa gat ggt gaa gct           2097
Pro Gly Pro Pro Gly Ala Val Gly Pro Ala Gly Lys Asp Gly Glu Ala
                630                 635                 640 gga gca cag ggc cct cca ggc cct gct ggc cca gct ggc gaa cgt gga           2145
Gly Ala Gln Gly Pro Pro Gly Pro Ala Gly Pro Ala Gly Glu Arg Gly
            645                 650                 655 gaa caa ggc cca gct ggt agt cca gga ttt caa gga ttg cct ggc cct           2193
Glu Gln Gly Pro Ala Gly Ser Pro Gly Phe Gln Gly Leu Pro Gly Pro
        660                 665                 670 gct ggc cct cca gga gaa gca gga aaa cct gga gaa caa gga gtt cct           2241
Ala Gly Pro Pro Gly Glu Ala Gly Lys Pro Gly Glu Gln Gly Val Pro
675                 680                 685 ggt gat ttg gga gca cct gga cct tca gga gca cgt ggt gaa aga ggc           2289
Gly Asp Leu Gly Ala Pro Gly Pro Ser Gly Ala Arg Gly Glu Arg Gly
690                 695                 700                 705 ttc cct ggc gag agg ggt gtt caa ggt cca cca ggt cca gca gga cct           2337
Phe Pro Gly Glu Arg Gly Val Gln Gly Pro Pro Gly Pro Ala Gly Pro
                710                 715                 720 aga ggt gct aat ggc gct cct ggc aac gat gga gca aaa ggt gat gct           2385
```

```
                       Arg Gly Ala Asn Gly Ala Pro Gly Asn Asp Gly Ala Lys Gly Asp Ala
                                       725                 730                 735 ggt gct cct ggc gca cct gga agt cag ggt gct cct gga ttg caa gga          2433
Gly Ala Pro Gly Ala Pro Gly Ser Gln Gly Ala Pro Gly Leu Gln Gly
            740                 745                 750 atg cct gga gag agg ggt gct gct ggc ttg cca ggc cca aag ggc gat          2481
Met Pro Gly Glu Arg Gly Ala Ala Gly Leu Pro Gly Pro Lys Gly Asp
    755                 760                 765 agg ggt gat gct gga cca aaa ggt gct gat gga tcc cca gga aaa gat          2529
Arg Gly Asp Ala Gly Pro Lys Gly Ala Asp Gly Ser Pro Gly Lys Asp
770                 775                 780                 785 gga gtt cgt ggt ctt act ggc cca atc gga cct cca ggc cct gct ggc          2577
Gly Val Arg Gly Leu Thr Gly Pro Ile Gly Pro Pro Gly Pro Ala Gly
                790                 795                 800 gct cca ggt gat aag ggc gaa agt ggc cca agt gga cct gct gga cct          2625
Ala Pro Gly Asp Lys Gly Glu Ser Gly Pro Ser Gly Pro Ala Gly Pro
                805                 810                 815 act ggt gct aga ggt gca cct ggt gat agg ggt gaa cct gga cca cct          2673
Thr Gly Ala Arg Gly Ala Pro Gly Asp Arg Gly Glu Pro Gly Pro Pro
            820                 825                 830 ggt cca gct ggt ttt gct ggt cct cct gga gct gat gga caa cct ggc          2721
Gly Pro Ala Gly Phe Ala Gly Pro Pro Gly Ala Asp Gly Gln Pro Gly
        835                 840                 845 gca aag ggt gaa cca ggt gat gct ggc gca aag gga gat gct ggt cca          2769
Ala Lys Gly Glu Pro Gly Asp Ala Gly Ala Lys Gly Asp Ala Gly Pro
850                 855                 860                 865 cct gga cct gct ggt cca gca ggc ccc cct ggg cca atc ggt aat gtt          2817
Pro Gly Pro Ala Gly Pro Ala Gly Pro Pro Gly Pro Ile Gly Asn Val
                870                 875                 880 gga gca cca ggt gct aag gga gct agg ggt tcc gct ggt cca cct gga          2865
Gly Ala Pro Gly Ala Lys Gly Ala Arg Gly Ser Ala Gly Pro Pro Gly
                885                 890                 895 gca aca gga ttt cca ggc gct gct ggt aga gtt ggc cca cca ggc cca          2913
Ala Thr Gly Phe Pro Gly Ala Ala Gly Arg Val Gly Pro Pro Gly Pro
            900                 905                 910 tcc gga aac gca ggc cct cct ggt cct cca ggt cct gct ggc aag gag          2961
Ser Gly Asn Ala Gly Pro Pro Gly Pro Pro Gly Pro Ala Gly Lys Glu
        915                 920                 925 ggt ggc aaa gga cca agg ggc gaa act ggc cct gct ggt aga cct ggc          3009
Gly Gly Lys Gly Pro Arg Gly Glu Thr Gly Pro Ala Gly Arg Pro Gly
930                 935                 940                 945 gaa gtt ggc cct cct gga cca cca ggt cca gca gga gaa aaa ggt tcc          3057
Glu Val Gly Pro Pro Gly Pro Pro Gly Pro Ala Gly Glu Lys Gly Ser
                950                 955                 960 cca gga gct gat ggc cca gct ggt gct cca gga act cca ggc cct caa          3105
Pro Gly Ala Asp Gly Pro Ala Gly Ala Pro Gly Thr Pro Gly Pro Gln
                965                 970                 975 ggt att gct gga cag aga ggc gtt gtg gga ctc cct ggt caa agg gga          3153
Gly Ile Ala Gly Gln Arg Gly Val Val Gly Leu Pro Gly Gln Arg Gly
            980                 985                 990 gag aga gga ttt cca ggc ttg  cca gga cct agt gga  gaa cct gga aaa        3201
Glu Arg Gly Phe Pro Gly Leu  Pro Gly Pro Ser Gly  Glu Pro Gly Lys
        995                 1000                1005 caa ggc cca tca ggc gct  agt gga gag cgt gga  cct cct ggc cct            3246
Gln Gly Pro Ser Gly Ala  Ser Gly Glu Arg Gly  Pro Pro Gly Pro
1010                1015                1020 atg gga cct cct gga ttg  gct ggc cca cct ggc  gaa tca ggt cgt            3291
Met Gly Pro Pro Gly Leu  Ala Gly Pro Pro Gly  Glu Ser Gly Arg
1025                1030                1035 gaa  ggc gca cca ggc gca  gaa gga tca cct gga  aga gat gga tcc           3336
```

|     |     |     |     |     |     |     |     |     |     |     |     |      |
| --- | --- | --- | --- | --- | --- | --- | --- | --- | --- | --- | --- | ---  |
| Glu | Gly | Ala | Pro | Gly | Ala | Glu | Gly | Ser | Pro | Gly | Arg | Asp | Gly | Ser |
| 1040 |     |     |     | 1045 |     |     |     | 1050 |     |     |     |     |     |     |

```
cct ggt gct aaa ggc gat cgt gga gaa act ggt cca gca ggc cca      3381
Pro Gly Ala Lys Gly Asp Arg Gly Glu Thr Gly Pro Ala Gly Pro
1055             1060                 1065 cca ggc gca cca ggt gca cct ggc gct cca gga cct gtg gga cca      3426
Pro Gly Ala Pro Gly Ala Pro Gly Ala Pro Gly Pro Val Gly Pro
1070             1075                 1080 gct gga aaa tcc gga gat agg ggc gag aca ggc cca gca gga cca      3471
Ala Gly Lys Ser Gly Asp Arg Gly Glu Thr Gly Pro Ala Gly Pro
1085             1090                 1095 gct gga cct gtt ggc cct gct ggc gct cgt gga cca gca gga cct      3516
Ala Gly Pro Val Gly Pro Ala Gly Ala Arg Gly Pro Ala Gly Pro
1100             1105                 1110 caa gga cca agg gga gat aag gga gaa aca ggc gaa caa ggc gat      3561
Gln Gly Pro Arg Gly Asp Lys Gly Glu Thr Gly Glu Gln Gly Asp
1115             1120                 1125 agg ggc att aag ggt cat agg ggt ttt agt ggc ctc cag ggt cct      3606
Arg Gly Ile Lys Gly His Arg Gly Phe Ser Gly Leu Gln Gly Pro
1130             1135                 1140 cct ggc cca cct gga tca cca gga gaa cag gga cca tct ggt gct      3651
Pro Gly Pro Pro Gly Ser Pro Gly Glu Gln Gly Pro Ser Gly Ala
1145             1150                 1155 tcc ggc cca gct ggt cca aga gga cct cca gga tca gct ggt gca      3696
Ser Gly Pro Ala Gly Pro Arg Gly Pro Pro Gly Ser Ala Gly Ala
1160             1165                 1170 cct gga aaa gat ggt ctt aac ggt ctc cca gga cca atc ggc cct      3741
Pro Gly Lys Asp Gly Leu Asn Gly Leu Pro Gly Pro Ile Gly Pro
1175             1180                 1185 cca gga cct aga gga aga aca gga gat gct ggc cct gtt ggc cct      3786
Pro Gly Pro Arg Gly Arg Thr Gly Asp Ala Gly Pro Val Gly Pro
1190             1195                 1200 cca gga cct cct ggt cca cca ggt cca cct ggt cct cca tca gct      3831
Pro Gly Pro Pro Gly Pro Pro Gly Pro Pro Gly Pro Pro Ser Ala
1205             1210                 1215 gga ttc gat ttt tca ttt ctt cca cag cca cca caa gag aaa gct      3876
Gly Phe Asp Phe Ser Phe Leu Pro Gln Pro Pro Gln Glu Lys Ala
1220             1225                 1230 cac gat ggc ggc aga tat tac cgt gct gat gat gct aac gtt gtt      3921
His Asp Gly Gly Arg Tyr Tyr Arg Ala Asp Asp Ala Asn Val Val
1235             1240                 1245 agg gat aga gat ttg gaa gtg gat aca act ttg aaa tcc ctc tcc      3966
Arg Asp Arg Asp Leu Glu Val Asp Thr Thr Leu Lys Ser Leu Ser
1250             1255                 1260 cag caa att gaa aac att aga tct cca gaa ggt tca cgt aaa aac      4011
Gln Gln Ile Glu Asn Ile Arg Ser Pro Glu Gly Ser Arg Lys Asn
1265             1270                 1275 cca gct aga aca tgt cgt gat ttg aaa atg tgt cac tcc gat tgg      4056
Pro Ala Arg Thr Cys Arg Asp Leu Lys Met Cys His Ser Asp Trp
1280             1285                 1290 aaa agt ggt gaa tac tgg att gat cca aat cag ggc tgt aat ctc      4101
Lys Ser Gly Glu Tyr Trp Ile Asp Pro Asn Gln Gly Cys Asn Leu
1295             1300                 1305 gat gct atc aaa gtt ttc tgt aac atg gaa aca ggc gaa aca tgc      4146
Asp Ala Ile Lys Val Phe Cys Asn Met Glu Thr Gly Glu Thr Cys
1310             1315                 1320 gtt tat cct act caa cct tcc gtg gct cag aaa aat tgg tac atc      4191
Val Tyr Pro Thr Gln Pro Ser Val Ala Gln Lys Asn Trp Tyr Ile
1325             1330                 1335 tca aaa aat cct aaa gat aag agg cac gtt tgg ttc ggt gaa agt      4236
```

```
Ser  Lys  Asn  Pro  Lys  Asp  Lys  Arg  His  Val  Trp  Phe  Gly  Glu  Ser
1340                1345                1350 atg  act  gat  gga  ttt  caa  ttt  gag  tac  ggc  ggt  caa  ggt  agt  gat         4281
Met  Thr  Asp  Gly  Phe  Gln  Phe  Glu  Tyr  Gly  Gly  Gln  Gly  Ser  Asp
1355                1360                1365 cca  gct  gat  gtg  gct  att  caa  ctc  aca  ttt  ttg  cgt  ctt  atg  tcc         4326
Pro  Ala  Asp  Val  Ala  Ile  Gln  Leu  Thr  Phe  Leu  Arg  Leu  Met  Ser
1370                1375                1380 aca  gag  gca  tca  caa  aac  atc  act  tac  cac  tgc  aaa  aac  agt  gtg         4371
Thr  Glu  Ala  Ser  Gln  Asn  Ile  Thr  Tyr  His  Cys  Lys  Asn  Ser  Val
1385                1390                1395 gct  tat  atg  gat  caa  caa  aca  gga  aac  ctt  aag  aag  gct  ctt  ctt         4416
Ala  Tyr  Met  Asp  Gln  Gln  Thr  Gly  Asn  Leu  Lys  Lys  Ala  Leu  Leu
1400                1405                1410 ttg  aag  ggc  tca  aac  gag  att  gag  att  aga  gca  gag  ggc  aac  tca         4461
Leu  Lys  Gly  Ser  Asn  Glu  Ile  Glu  Ile  Arg  Ala  Glu  Gly  Asn  Ser
1415                1420                1425 agg  ttt  act  tat  tca  gtt  act  gtt  gat  ggc  tgc  act  tca  cat  act         4506
Arg  Phe  Thr  Tyr  Ser  Val  Thr  Val  Asp  Gly  Cys  Thr  Ser  His  Thr
1430                1435                1440 ggc  gct  tgg  ggt  aaa  aca  gtt  atc  gag  tat  aag  act  aca  aaa  aca         4551
Gly  Ala  Trp  Gly  Lys  Thr  Val  Ile  Glu  Tyr  Lys  Thr  Thr  Lys  Thr
1445                1450                1455 tca  aga  ctc  cca  atc  att  gat  gtt  gct  cct  ctc  gat  gtt  ggc  gct         4596
Ser  Arg  Leu  Pro  Ile  Ile  Asp  Val  Ala  Pro  Leu  Asp  Val  Gly  Ala
1460                1465                1470 cct  gat  caa  gag  ttc  ggt  ttt  gat  gtg  ggc  cca  gtt  tgt  ttc  ctc         4641
Pro  Asp  Gln  Glu  Phe  Gly  Phe  Asp  Val  Gly  Pro  Val  Cys  Phe  Leu
1475                1480                1485 taa  tgagctcgcg  gccgcatc                                                          4662
```

<210> SEQ ID NO 3
<211> LENGTH: 1489
<212> TYPE: PRT
<213> ORGANISM: Artificial sequence
<220> FEATURE:
<223> OTHER INFORMATION: Synthetic Construct

<400> SEQUENCE: 3

```
Met  Ala  His  Ala  Arg  Val  Leu  Leu  Ala  Leu  Ala  Val  Leu  Ala  Thr
1                 5                   10                  15

Ala  Ala  Val  Ala  Val  Ala  Ser  Ser  Ser  Phe  Ala  Asp  Ser  Asn  Pro
                 20                  25                  30

Ile  Arg  Pro  Val  Thr  Asp  Arg  Ala  Ala  Ser  Thr  Leu  Ala  Gln  Leu  Gln
            35                  40                  45

Glu  Glu  Gly  Gln  Val  Glu  Gly  Gln  Asp  Glu  Asp  Ile  Pro  Pro  Ile  Thr
        50                  55                  60

Cys  Val  Gln  Asn  Gly  Leu  Arg  Tyr  His  Asp  Arg  Asp  Val  Trp  Lys  Pro
65                  70                  75                  80

Glu  Pro  Cys  Arg  Ile  Cys  Val  Cys  Asp  Asn  Gly  Lys  Val  Leu  Cys  Asp
                85                  90                  95

Asp  Val  Ile  Cys  Asp  Glu  Thr  Lys  Asn  Cys  Pro  Gly  Ala  Glu  Val  Pro
            100                 105                 110

Glu  Gly  Glu  Cys  Cys  Pro  Val  Cys  Pro  Asp  Gly  Ser  Glu  Ser  Pro  Thr
        115                 120                 125

Asp  Gln  Glu  Thr  Thr  Gly  Val  Glu  Gly  Pro  Lys  Gly  Asp  Thr  Gly  Pro
    130                 135                 140

Arg  Gly  Pro  Arg  Gly  Pro  Ala  Gly  Pro  Pro  Gly  Arg  Asp  Gly  Ile  Pro
145                 150                 155                 160
```

```
Gly Gln Pro Gly Leu Pro Gly Pro Pro Gly Pro Pro Gly
            165                 170                 175
Pro Pro Gly Leu Gly Gly Asn Phe Ala Pro Gln Leu Ser Tyr Gly Tyr
            180                 185                 190
Asp Glu Lys Ser Thr Gly Gly Ile Ser Val Pro Gly Pro Met Gly Pro
            195                 200                 205
Ser Gly Pro Arg Gly Leu Pro Gly Pro Pro Gly Ala Pro Gly Pro Gln
210                 215                 220
Gly Phe Gln Gly Pro Pro Gly Glu Pro Gly Glu Pro Gly Ala Ser Gly
225                 230                 235                 240
Pro Met Gly Pro Arg Gly Pro Pro Gly Pro Pro Gly Lys Asn Gly Asp
                245                 250                 255
Asp Gly Glu Ala Gly Lys Pro Gly Arg Pro Gly Glu Arg Gly Pro Pro
            260                 265                 270
Gly Pro Gln Gly Ala Arg Gly Leu Pro Gly Thr Ala Gly Leu Pro Gly
            275                 280                 285
Met Lys Gly His Arg Gly Phe Ser Gly Leu Asp Gly Ala Lys Gly Asp
            290                 295                 300
Ala Gly Pro Ala Gly Pro Lys Gly Glu Pro Gly Ser Pro Gly Glu Asn
305                 310                 315                 320
Gly Ala Pro Gly Gln Met Gly Pro Arg Gly Leu Pro Gly Glu Arg Gly
                325                 330                 335
Arg Pro Gly Ala Pro Gly Pro Ala Gly Ala Arg Gly Asn Asp Gly Ala
            340                 345                 350
Thr Gly Ala Ala Gly Pro Pro Gly Pro Thr Gly Pro Ala Gly Pro Pro
            355                 360                 365
Gly Phe Pro Gly Ala Val Gly Ala Lys Gly Glu Ala Gly Pro Gln Gly
            370                 375                 380
Pro Arg Gly Ser Glu Gly Pro Gln Gly Val Arg Gly Glu Pro Gly Pro
385                 390                 395                 400
Pro Gly Pro Ala Gly Ala Ala Gly Pro Ala Gly Asn Pro Gly Ala Asp
                405                 410                 415
Gly Gln Pro Gly Ala Lys Gly Ala Asn Gly Ala Pro Gly Ile Ala Gly
            420                 425                 430
Ala Pro Gly Phe Pro Gly Ala Arg Gly Pro Ser Gly Pro Gln Gly Pro
            435                 440                 445
Gly Gly Pro Pro Gly Pro Lys Gly Asn Ser Gly Glu Pro Gly Ala Pro
450                 455                 460
Gly Ser Lys Gly Asp Thr Gly Ala Lys Gly Glu Pro Gly Pro Val Gly
465                 470                 475                 480
Val Gln Gly Pro Pro Gly Pro Ala Gly Glu Glu Gly Lys Arg Gly Ala
                485                 490                 495
Arg Gly Glu Pro Gly Pro Thr Gly Leu Pro Gly Pro Pro Gly Glu Arg
            500                 505                 510
Gly Gly Pro Gly Ser Arg Gly Phe Pro Gly Ala Asp Gly Val Ala Gly
            515                 520                 525
Pro Lys Gly Pro Ala Gly Glu Arg Gly Ser Pro Gly Pro Ala Gly Pro
            530                 535                 540
Lys Gly Ser Pro Gly Glu Ala Gly Arg Pro Gly Glu Ala Gly Leu Pro
545                 550                 555                 560
Gly Ala Lys Gly Leu Thr Gly Ser Pro Gly Ser Pro Gly Pro Asp Gly
                565                 570                 575
Lys Thr Gly Pro Pro Gly Pro Ala Gly Gln Asp Gly Arg Pro Gly Pro
```

```
                    580             585             590
Pro Gly Pro Pro Gly Ala Arg Gly Gln Ala Gly Val Met Gly Phe Pro
            595                 600                 605
Gly Pro Lys Gly Ala Ala Gly Glu Pro Gly Lys Ala Gly Glu Arg Gly
            610                 615                 620
Val Pro Gly Pro Pro Gly Ala Val Gly Pro Ala Gly Lys Asp Gly Glu
625                 630                 635                 640
Ala Gly Ala Gln Gly Pro Pro Gly Pro Ala Gly Pro Ala Gly Glu Arg
                645                 650                 655
Gly Glu Gln Gly Pro Ala Gly Ser Pro Gly Phe Gln Gly Leu Pro Gly
            660                 665                 670
Pro Ala Gly Pro Pro Gly Glu Ala Gly Lys Pro Gly Glu Gln Gly Val
            675                 680                 685
Pro Gly Asp Leu Gly Ala Pro Gly Pro Ser Gly Ala Arg Gly Glu Arg
            690                 695                 700
Gly Phe Pro Gly Glu Arg Gly Val Gln Gly Pro Pro Gly Pro Ala Gly
705                 710                 715                 720
Pro Arg Gly Ala Asn Gly Ala Pro Gly Asn Asp Gly Ala Lys Gly Asp
                725                 730                 735
Ala Gly Ala Pro Gly Ala Pro Gly Ser Gln Gly Ala Pro Gly Leu Gln
            740                 745                 750
Gly Met Pro Gly Glu Arg Gly Ala Ala Gly Leu Pro Gly Pro Lys Gly
            755                 760                 765
Asp Arg Gly Asp Ala Gly Pro Lys Gly Ala Asp Gly Ser Pro Gly Lys
            770                 775                 780
Asp Gly Val Arg Gly Leu Thr Gly Pro Ile Gly Pro Pro Gly Pro Ala
785                 790                 795                 800
Gly Ala Pro Gly Asp Lys Gly Glu Ser Gly Pro Ser Gly Pro Ala Gly
                805                 810                 815
Pro Thr Gly Ala Arg Gly Ala Pro Gly Asp Arg Gly Glu Pro Gly Pro
            820                 825                 830
Pro Gly Pro Ala Gly Phe Ala Gly Pro Pro Gly Ala Asp Gly Gln Pro
            835                 840                 845
Gly Ala Lys Gly Glu Pro Gly Asp Ala Gly Ala Lys Gly Asp Ala Gly
            850                 855                 860
Pro Pro Gly Pro Ala Gly Pro Ala Gly Pro Pro Gly Pro Ile Gly Asn
865                 870                 875                 880
Val Gly Ala Pro Gly Ala Lys Gly Ala Arg Gly Ser Ala Gly Pro Pro
                885                 890                 895
Gly Ala Thr Gly Phe Pro Gly Ala Ala Gly Arg Val Gly Pro Pro Gly
            900                 905                 910
Pro Ser Gly Asn Ala Gly Pro Pro Gly Pro Pro Gly Pro Ala Gly Lys
            915                 920                 925
Glu Gly Gly Lys Gly Pro Arg Gly Glu Thr Gly Pro Ala Gly Arg Pro
            930                 935                 940
Gly Glu Val Gly Pro Pro Gly Pro Pro Gly Pro Ala Gly Glu Lys Gly
945                 950                 955                 960
Ser Pro Gly Ala Asp Gly Pro Ala Gly Ala Pro Gly Thr Pro Gly Pro
                965                 970                 975
Gln Gly Ile Ala Gly Gln Arg Gly Val Val Gly Leu Pro Gly Gln Arg
            980                 985                 990
Gly Glu Arg Gly Phe Pro Gly Leu Pro Gly Pro Ser Gly Glu Pro Gly
            995                 1000                1005
```

-continued

```
Lys Gln Gly Pro Ser Gly Ala Ser Gly Glu Arg Gly Pro Pro Gly
    1010            1015                1020
Pro Met Gly Pro Pro Gly Leu Ala Gly Pro Pro Gly Glu Ser Gly
    1025            1030                1035
Arg Glu Gly Ala Pro Gly Ala Glu Gly Ser Pro Gly Arg Asp Gly
    1040            1045                1050
Ser Pro Gly Ala Lys Gly Asp Arg Gly Glu Thr Gly Pro Ala Gly
    1055            1060                1065
Pro Pro Gly Ala Pro Gly Ala Pro Gly Ala Pro Gly Pro Val Gly
    1070            1075                1080
Pro Ala Gly Lys Ser Gly Asp Arg Gly Glu Thr Gly Pro Ala Gly
    1085            1090                1095
Pro Ala Gly Pro Val Gly Pro Ala Gly Ala Arg Gly Pro Ala Gly
    1100            1105                1110
Pro Gln Gly Pro Arg Gly Asp Lys Gly Glu Thr Gly Glu Gln Gly
    1115            1120                1125
Asp Arg Gly Ile Lys Gly His Arg Gly Phe Ser Gly Leu Gln Gly
    1130            1135                1140
Pro Pro Gly Pro Pro Gly Ser Pro Gly Glu Gln Gly Pro Ser Gly
    1145            1150                1155
Ala Ser Gly Pro Ala Gly Pro Arg Gly Pro Pro Gly Ser Ala Gly
    1160            1165                1170
Ala Pro Gly Lys Asp Gly Leu Asn Gly Leu Pro Gly Pro Ile Gly
    1175            1180                1185
Pro Pro Gly Pro Arg Gly Arg Thr Gly Asp Ala Gly Pro Val Gly
    1190            1195                1200
Pro Pro Gly Pro Pro Gly Pro Pro Gly Pro Pro Gly Pro Pro Ser
    1205            1210                1215
Ala Gly Phe Asp Phe Ser Phe Leu Pro Gln Pro Pro Gln Glu Lys
    1220            1225                1230
Ala His Asp Gly Gly Arg Tyr Tyr Arg Ala Asp Asp Ala Asn Val
    1235            1240                1245
Val Arg Asp Arg Asp Leu Glu Val Asp Thr Thr Leu Lys Ser Leu
    1250            1255                1260
Ser Gln Gln Ile Glu Asn Ile Arg Ser Pro Glu Gly Ser Arg Lys
    1265            1270                1275
Asn Pro Ala Arg Thr Cys Arg Asp Leu Lys Met Cys His Ser Asp
    1280            1285                1290
Trp Lys Ser Gly Glu Tyr Trp Ile Asp Pro Asn Gln Gly Cys Asn
    1295            1300                1305
Leu Asp Ala Ile Lys Val Phe Cys Asn Met Glu Thr Gly Glu Thr
    1310            1315                1320
Cys Val Tyr Pro Thr Gln Pro Ser Val Ala Gln Lys Asn Trp Tyr
    1325            1330                1335
Ile Ser Lys Asn Pro Lys Asp Lys Arg His Val Trp Phe Gly Glu
    1340            1345                1350
Ser Met Thr Asp Gly Phe Gln Phe Glu Tyr Gly Gly Gln Gly Ser
    1355            1360                1365
Asp Pro Ala Asp Val Ala Ile Gln Leu Thr Phe Leu Arg Leu Met
    1370            1375                1380
Ser Thr Glu Ala Ser Gln Asn Ile Thr Tyr His Cys Lys Asn Ser
    1385            1390                1395
Val Ala Tyr Met Asp Gln Gln Thr Gly Asn Leu Lys Lys Ala Leu
    1400            1405                1410
```

| Leu | Leu | Lys | Gly | Ser | Asn | Glu | Ile | Glu | Ile | Arg | Ala | Glu | Gly | Asn |
| | 1415 | | | | 1420 | | | | 1425 | | | | | |

| Ser | Arg | Phe | Thr | Tyr | Ser | Val | Thr | Val | Asp | Gly | Cys | Thr | Ser | His |
| 1430 | | | | | 1435 | | | | 1440 | | | | | |

| Thr | Gly | Ala | Trp | Gly | Lys | Thr | Val | Ile | Glu | Tyr | Lys | Thr | Thr | Lys |
| 1445 | | | | | 1450 | | | | | 1455 | | | | |

| Thr | Ser | Arg | Leu | Pro | Ile | Ile | Asp | Val | Ala | Pro | Leu | Asp | Val | Gly |
| 1460 | | | | | 1465 | | | | | 1470 | | | | |

| Ala | Pro | Asp | Gln | Glu | Phe | Gly | Phe | Asp | Val | Gly | Pro | Val | Cys | Phe |
| 1475 | | | | | 1480 | | | | | 1485 | | | | |

Leu

<210> SEQ ID NO 4
<211> LENGTH: 4362
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Collagen alpha 2(I)
      chain and flanking regions

<400> SEQUENCE: 4

```
gcgatgcatg taatgtcatg agccacatga tccaatggcc acaggaacgt aagaatgtag    60
atagatttga ttttgtccgt tagatagcaa acaacattat aaaaggtgtg tatcaatacg   120
aactaattca ctcattggat tcatagaagt ccattcctcc taagtatcta aaccatggct   180
cacgctcgtg ttctcctcct cgctctcgct gttttggcaa cagctgctgt ggctgtggct   240
tcaagttcta gttttgctga ttccaaccca attcgtccag ttactgatag agcagcttcc   300
actttggctc aattgcttca agaagaaact gtgaggaagg ccctgctgg cgatagggc    360
cctaggggcg aaaggggtcc accaggacct ccagcaggg atggcgaaga tggtccaact   420
ggccctcctg gacctcctgg ccctccaggg ccaccggct tgggcggaaa cttcgcagct   480
caatacgatg caagggtgt tggtcttggt cctggtccta tgggcttgat gggacctaga   540
ggcccacctg gtgctgctgg tgctcctgga ccacagggtt tcagggacc agctggcgag   600
ccaggagagc caggccaaac aggaccagct ggtgcaaggg gacctgctgg acctcctgga   660
aaagctggtg aagatggtca cccaggcaaa ccaggacgtc ctggcgaaag aggtgttgtt   720
ggaccacaag cgctagggg atttccaggt acacctggat tgccaggttt aagggcatt    780
cgtggtcata acggcctcga tggattgaag ggacagcctg gcgcacctgg cgttaagggt   840
gaacctggag caccaggtga aaacggtact cctggccaga ctggtgcaag aggactccca   900
ggtgaaaggg gtagagttgg tgctcctgga cctgctggag ctaggggtag tgatggtagt   960
gttggtcctg tgggccctgc tggtccaatc ggttccgctg gcccacctgg attcccaggc  1020
gctccaggac ctaaaggaga aatcggtgct gtgggtaacg caggtcctac tggtccagca  1080
ggtcctcgtg gagaagtggg attgccagga cttctggtc cagtgggccc tccaggcaac  1140
cctggagcta acggcttgac aggagctaaa ggcgcagcag gactccctgg agtggctggc  1200
gcaccaggat tgcctggtcc aaggggtatc ccaggccctg ttggcgcagc tggagctact  1260
ggtgcacgtg gacttgttgg cgaaccaggc cctgctggat caaaaggcga gtctggaaat  1320
aagggagaac ctggttctgc tggacctcaa gtcctcctg gaccttctgg agaagaagga  1380
aaaaggggac caaatggcga ggctggatca gcaggtccac caggaccacc tggacttcgt  1440
ggatccctg gtagtagag acttccagge gctgatggta gagcaggcgt tatgggacca  1500
```

```
ccaggaagta gaggagcatc cggtccagca ggagttaggg gtcctaacgg agatgctggt    1560
agaccaggtg aaccaggtct tatgggccca aggggcctcc caggtagtcc aggaaatatc    1620
ggccctgctg gaaaagaagg ccctgttgga cttccaggta ttgatggacg tcctggccct    1680
attggcccag caggtgcaag aggagaacct ggcaatattg gatttccagg accaaagggt    1740
ccaacaggcg atcctggaaa aaatggagat aagggtcatg ctggattggc aggcgcaagg    1800
ggcgctcctg gtccagatgg aaacaacggc gcacagggtc cacctggccc tcagggtgtt    1860
caaggcggaa aaggcaaaca aggcccagct ggaccaccag gctttcaagg cttgccagga    1920
ccaagtggtc cagcaggtga agttggcaag ccaggcgagc gtggacttca tggcgagttt    1980
ggactccctg gaccagcagg accaaggggt gaaagaggcc ctcctggaga gagtggcgct    2040
gctggaccaa caggcccaat cggtagtaga ggtcctagtg gacctccagg cccagatgga    2100
aataagggtg aaccaggagt tgtgggcgct gttggaacag ctggtccttc aggaccatca    2160
ggactcccag gcgagagagg cgctgctggc attcctggag aaaaggtga aaaaggcgaa    2220 cctggcctcc gtggcgaaat cggaaatcct ggacgtgatg gtgctcgtgg tgcacacggc    2280
gctgtgggcg ctccaggccc tgctggtgct actggtgata gaggagaggc tggcgcagct    2340
ggcccagcag gtcctgctgg cccaaggggt agtcctggtg aaagaggcga agttggacct    2400
gctgccccta acggctttgc tggccctgct ggagcagcag tcaacctggc gctaaaggt    2460 gaaggggcg gaagggccc aaaaggtgaa atggcgttg tgggaccaac tggtccagtg    2520
ggcgcagctg gacctgctgg tccaaatgga ccaccaggac cagcaggtag tagaggagat    2580
ggtggacctc caggaatgac aggttttcca ggtgctgctg gtagaacagg acctcctggt    2640
cctagtggta tttctggtcc accaggacca ccaggtcctg ctggaaaaga aggattgagg    2700
ggtccacgtg gtgatcaagg accagtgggc agaactggtg aagttggcgc agtgggacca    2760
cctggttttg ctggagaaaaa gggcccttct ggagaggcag gaacagctgg tcctcctggt    2820
acacctggac ctcaaggact tttgggtgca cctggtattc tcggattgcc aggaagtagg    2880
ggcgaacgtg gacttcctgg cgtggcagga gcagttggag aacctggccc tctcggaatc    2940
gcaggcccac caggcgcaag aggaccacca ggagctgttg gatcaccagg cgtgaatggt    3000
gcacctggcg aggctggtcg tgatggaaac ccaggaaatg atggcccacc aggaagagat    3060
ggtcaacctg gacacaaagg cgagagggc tacccaggaa atattggccc agttggtgct    3120
gctggcgcac caggcccaca cggtccagtt ggaccagcag gaaaacacgg taatcgtggc    3180
gaaacaggcc cttcaggccc agtgggacct gctggtgctg ttggcccaag aggaccatct    3240
ggacctcaag gcattagagg cgataaggga gagcctggcg aaaaaggacc tagaggcttg    3300 cctggttttta aaggacacaa cggtctccaa ggacttccag gtatcgctgg tcatcatgga    3360
gatcagggtg ctcctggatc agtgggtcca gcaggtccta gaggcccagc aggcccttcc    3420
ggtccagcag gaaaggatgg acgtactggc caccctggaa ctgtgggccc tgctggaatt    3480
agaggtcctc aaggtcatca gggccctgct ggccctccag tccaccagg tcctccaggc    3540 ccaccaggag tttcaggtgg tggttacgat tttggttacg atggtgattt ttaccgtgct    3600
gatcaaccta gaagtgctcc ttctctccgt cctaaagatt atgaagttga tgctactttg    3660
aaatcactta acaaccagat tgagactctt ctcacacctg agggatcaag aaagaatcca    3720
gcacgtacat gccgtgatct cagacttagt cacccagagt ggtcaagtgg ctattattgg    3780
attgatccta atcaggggttg tacaatggag gctatcaaag tttactgtga tttttccaact    3840 ggagagacat gtattagggc acaacctgag aacattccag ctaaaaattg gtatcgttcc    3900
```

```
tctaaagata agaaacatgt ttggctcgga gagactatta acgctggttc tcagttcgag   3960
tataatgttg agggcgttac ttctaaagag atggcaactc agctcgcttt tatgagattg   4020
ctcgctaact acgcatccca aaacatcact tatcactgca aaaattccat tgcatatatg   4080
gatgaggaga caggaaattt gaagaaagca gttattctcc aaggtagtaa cgatgttgag   4140
cttgtggctg agggaaatag tagattcact tacacagttt tggtggatgg atgctcaaag   4200
aaaactaatg agtggggcaa gacaatcatt gagtacaaga caaataagcc ttctaggctc   4260
ccatttctcg atattgcacc tcttgatatc ggaggagctg atcacgagtt ttttgttgat   4320
atcggacctg tttgttttaa gtaatgagct cgcggccgca tc                     4362

<210> SEQ ID NO 5
<211> LENGTH: 4362
<212> TYPE: DNA
<213> ORGANISM: Artificial sequence
<220> FEATURE:
<223> OTHER INFORMATION: Synthetic sequence of the vacuolar signal
      sequence of barley gene for Thiol protease aleurain precursor
      fused to the human Collagen alpha 2(I) chain and flanking regions
<220> FEATURE:
<221> NAME/KEY: CDS
<222> LOCATION: (175)..(4344)

<400> SEQUENCE: 5
gcgatgcatg taatgtcatg agccacatga tccaatggcc acaggaacgt aagaatgtag    60
atagatttga ttttgtccgt tagatagcaa acaacattat aaaaggtgtg tatcaatacg   120
aactaattca ctcattggat tcatagaagt ccattcctcc taagtatcta aacc atg    177
                                                              Met
                                                               1 gct cac gct cgt gtt ctc ctc ctc gct ctc gct gtt ttg gca aca gct    225
Ala His Ala Arg Val Leu Leu Leu Ala Leu Ala Val Leu Ala Thr Ala
            5                  10                  15 gct gtg gct gtg gct tca agt tct agt ttt gct gat tcc aac cca att    273
Ala Val Ala Val Ala Ser Ser Ser Ser Phe Ala Asp Ser Asn Pro Ile
         20                  25                  30 cgt cca gtt act gat aga gca gct tcc act ttg gct caa ttg ctt caa    321
Arg Pro Val Thr Asp Arg Ala Ala Ser Thr Leu Ala Gln Leu Leu Gln
     35                  40                  45 gaa gaa act gtg agg aag ggc cct gct ggc gat agg ggc cct agg ggc    369
Glu Glu Thr Val Arg Lys Gly Pro Ala Gly Asp Arg Gly Pro Arg Gly
 50                  55                  60                  65 gaa agg ggt cca cca gga cct cca ggc agg gat ggc gaa gat ggt cca    417
Glu Arg Gly Pro Pro Gly Pro Pro Gly Arg Asp Gly Glu Asp Gly Pro
                 70                  75                  80 act ggc cct cct gga cct cct ggc cct cca ggg cca ccc ggc ttg ggc    465
Thr Gly Pro Pro Gly Pro Pro Gly Pro Pro Gly Pro Pro Gly Leu Gly
             85                  90                  95 gga aac ttc gca gct caa tac gat ggc aag ggt gtt ggt ctt ggt cct    513
Gly Asn Phe Ala Ala Gln Tyr Asp Gly Lys Gly Val Gly Leu Gly Pro
        100                 105                 110 ggt cct atg ggc ttg atg gga cct aga ggc cca cct ggt gct gct ggt    561
Gly Pro Met Gly Leu Met Gly Pro Arg Gly Pro Pro Gly Ala Ala Gly
    115                 120                 125 gct cct gga cca cag ggt ttt cag gga cca gct ggc gag cca gga gag    609
Ala Pro Gly Pro Gln Gly Phe Gln Gly Pro Ala Gly Glu Pro Gly Glu
130                 135                 140                 145 cca ggc caa aca gga cca gct ggt gca agg gga cct gct gga cct cct    657
Pro Gly Gln Thr Gly Pro Ala Gly Ala Arg Gly Pro Ala Gly Pro Pro
                150                 155                 160
```

-continued

| | | |
|---|---|---|
| gga aaa gct ggt gaa gat ggt cac cca ggc aaa cca gga cgt cct ggc<br>Gly Lys Ala Gly Glu Asp Gly His Pro Gly Lys Pro Gly Arg Pro Gly<br>                  165                        170                        175 | 705 | |
| gaa aga ggt gtt gtt gga cca caa ggc gct agg gga ttt cca ggt aca<br>Glu Arg Gly Val Val Gly Pro Gln Gly Ala Arg Gly Phe Pro Gly Thr<br>         180                        185                        190 | 753 | |
| cct gga ttg cca ggt ttt aag ggc att cgt ggt cat aac ggc ctc gat<br>Pro Gly Leu Pro Gly Phe Lys Gly Ile Arg Gly His Asn Gly Leu Asp<br>         195                        200                        205 | 801 | |
| gga ttg aag gga cag cct ggc gca cct ggc gtt aag ggt gaa cct gga<br>Gly Leu Lys Gly Gln Pro Gly Ala Pro Gly Val Lys Gly Glu Pro Gly<br>210                        215                        220                        225 | 849 | |
| gca cca ggt gaa aac ggt act cct ggc cag act ggt gca aga gga ctc<br>Ala Pro Gly Glu Asn Gly Thr Pro Gly Gln Thr Gly Ala Arg Gly Leu<br>                        230                        235                        240 | 897 | |
| cca ggt gaa agg ggt aga gtt ggt gct cct gga cct gct gga gct agg<br>Pro Gly Glu Arg Gly Arg Val Gly Ala Pro Gly Pro Ala Gly Ala Arg<br>                      245                        250                        255 | 945 | |
| ggt agt gat ggt agt gtt ggt cct gtg ggc cct gct ggt cca atc ggt<br>Gly Ser Asp Gly Ser Val Gly Pro Val Gly Pro Ala Gly Pro Ile Gly<br>                    260                        265                        270 | 993 | |
| tcc gct ggc cca cct gga ttc cca ggc gct cca gga cct aaa gga gaa<br>Ser Ala Gly Pro Pro Gly Phe Pro Gly Ala Pro Gly Pro Lys Gly Glu<br>275                        280                        285 | 1041 | |
| atc ggt gct gtg ggt aac gca ggt cct act ggt cca gca ggt cct cgt<br>Ile Gly Ala Val Gly Asn Ala Gly Pro Thr Gly Pro Ala Gly Pro Arg<br>290                        295                        300                        305 | 1089 | |
| gga gaa gtg gga ttg cca gga ctt tct ggt cca gtg ggc cct cca ggc<br>Gly Glu Val Gly Leu Pro Gly Leu Ser Gly Pro Val Gly Pro Pro Gly<br>                    310                        315                        320 | 1137 | |
| aac cct gga gct aac ggc ttg aca gga gct aaa ggc gca gca gga ctc<br>Asn Pro Gly Ala Asn Gly Leu Thr Gly Ala Lys Gly Ala Ala Gly Leu<br>                        325                        330                        335 | 1185 | |
| cct gga gtg gct ggc gca cca gga ttg cct ggt cca agg ggt atc cca<br>Pro Gly Val Ala Gly Ala Pro Gly Leu Pro Gly Pro Arg Gly Ile Pro<br>                    340                        345                        350 | 1233 | |
| ggc cct gtt ggc gca gct gga gct act ggt gca cgt gga ctt gtt ggc<br>Gly Pro Val Gly Ala Ala Gly Ala Thr Gly Ala Arg Gly Leu Val Gly<br>355                        360                        365 | 1281 | |
| gaa cca ggc cct gct gga tca aaa ggc gag tct gga aat aag gga gaa<br>Glu Pro Gly Pro Ala Gly Ser Lys Gly Glu Ser Gly Asn Lys Gly Glu<br>370                        375                        380                        385 | 1329 | |
| cct ggt tct gct gga cct caa ggt cct cct gga cct tct gga gaa gaa<br>Pro Gly Ser Ala Gly Pro Gln Gly Pro Pro Gly Pro Ser Gly Glu Glu<br>                    390                        395                        400 | 1377 | |
| gga aaa agg gga cca aat ggc gag gct gga tca gca ggt cca cca gga<br>Gly Lys Arg Gly Pro Asn Gly Glu Ala Gly Ser Ala Gly Pro Pro Gly<br>                        405                        410                        415 | 1425 | |
| cca cct gga ctt cgt gga tcc cct ggt agt aga gga ctt cca ggc gct<br>Pro Pro Gly Leu Arg Gly Ser Pro Gly Ser Arg Gly Leu Pro Gly Ala<br>                    420                        425                        430 | 1473 | |
| gat ggt aga gca ggc gtt atg gga cca cca gga agt aga gga gca tcc<br>Asp Gly Arg Ala Gly Val Met Gly Pro Pro Gly Ser Arg Gly Ala Ser<br>435                        440                        445 | 1521 | |
| ggt cca gca gga gtt agg ggt cct aac gga gat gct ggt aga cca ggt<br>Gly Pro Ala Gly Val Arg Gly Pro Asn Gly Asp Ala Gly Arg Pro Gly<br>450                        455                        460                        465 | 1569 | |
| gaa cca ggt ctt atg ggc cca agg ggc ctc cca ggt agt cca gga aat<br>Glu Pro Gly Leu Met Gly Pro Arg Gly Leu Pro Gly Ser Pro Gly Asn<br>                    470                        475                        480 | 1617 | |

-continued

| | | |
|---|---|---|
| atc ggc cct gct gga aaa gaa ggc cct gtt gga ctt cca ggt att gat<br>Ile Gly Pro Ala Gly Lys Glu Gly Pro Val Gly Leu Pro Gly Ile Asp<br>485 490 495 | 1665 | |
| gga cgt cct ggc cct att ggc cca gca ggt gca aga gga gaa cct ggc<br>Gly Arg Pro Gly Pro Ile Gly Pro Ala Gly Ala Arg Gly Glu Pro Gly<br>500 505 510 | 1713 | |
| aat att gga ttt cca gga cca aag ggt cca aca ggc gat cct gga aaa<br>Asn Ile Gly Phe Pro Gly Pro Lys Gly Pro Thr Gly Asp Pro Gly Lys<br>515 520 525 | 1761 | |
| aat gga gat aag ggt cat gct gga ttg gca ggc gca agg ggc gct cct<br>Asn Gly Asp Lys Gly His Ala Gly Leu Ala Gly Ala Arg Gly Ala Pro<br>530 535 540 545 | 1809 | |
| ggt cca gat gga aac aac ggc gca cag ggt cca cct ggc cct cag ggt<br>Gly Pro Asp Gly Asn Asn Gly Ala Gln Gly Pro Pro Gly Pro Gln Gly<br>550 555 560 | 1857 | |
| gtt caa ggc gga aaa ggc gaa caa ggc cca gct gga cca cca ggc ttt<br>Val Gln Gly Gly Lys Gly Glu Gln Gly Pro Ala Gly Pro Pro Gly Phe<br>565 570 575 | 1905 | |
| caa ggc ttg cca gga cca agt ggt cca gca ggt gaa gtt ggc aag cca<br>Gln Gly Leu Pro Gly Pro Ser Gly Pro Ala Gly Glu Val Gly Lys Pro<br>580 585 590 | 1953 | |
| ggc gag cgt gga ctt cat ggc gag ttt gga ctc cct gga cca gca gga<br>Gly Glu Arg Gly Leu His Gly Glu Phe Gly Leu Pro Gly Pro Ala Gly<br>595 600 605 | 2001 | |
| cca agg ggt gaa aga ggc cct cct gga gag agt ggc gct gct gga cca<br>Pro Arg Gly Glu Arg Gly Pro Pro Gly Glu Ser Gly Ala Ala Gly Pro<br>610 615 620 625 | 2049 | |
| aca ggc cca atc ggt agt aga ggt cct agt gga cct cca ggc cca gat<br>Thr Gly Pro Ile Gly Ser Arg Gly Pro Ser Gly Pro Pro Gly Pro Asp<br>630 635 640 | 2097 | |
| gga aat aag ggt gaa cca gga gtt gtg ggc gct gtt gga aca gct ggt<br>Gly Asn Lys Gly Glu Pro Gly Val Val Gly Ala Val Gly Thr Ala Gly<br>645 650 655 | 2145 | |
| cct tca gga cca tca gga ctc cca ggc gag aga ggc gct gct ggc att<br>Pro Ser Gly Pro Ser Gly Leu Pro Gly Glu Arg Gly Ala Ala Gly Ile<br>660 665 670 | 2193 | |
| cct gga gga aaa ggt gaa aaa ggc gaa cct ggc ctc cgt ggc gaa atc<br>Pro Gly Gly Lys Gly Glu Lys Gly Glu Pro Gly Leu Arg Gly Glu Ile<br>675 680 685 | 2241 | |
| gga aat cct gga cgt gat ggt gct cgt ggt gca cac ggc gct gtg ggc<br>Gly Asn Pro Gly Arg Asp Gly Ala Arg Gly Ala His Gly Ala Val Gly<br>690 695 700 705 | 2289 | |
| gct cca ggc cct gct ggt gct act ggt gat aga gga gag gct ggc gca<br>Ala Pro Gly Pro Ala Gly Ala Thr Gly Asp Arg Gly Glu Ala Gly Ala<br>710 715 720 | 2337 | |
| gct ggc cca gca ggt cct gct ggc cca agg ggt agt cct ggt gaa aga<br>Ala Gly Pro Ala Gly Pro Ala Gly Pro Arg Gly Ser Pro Gly Glu Arg<br>725 730 735 | 2385 | |
| ggc gaa gtt gga cct gct ggc cct aac ggc ttt gct ggc cct gct gga<br>Gly Glu Val Gly Pro Ala Gly Pro Asn Gly Phe Ala Gly Pro Ala Gly<br>740 745 750 | 2433 | |
| gca gca ggt caa cct ggc gct aaa ggt gaa agg ggc gga aag ggc cca<br>Ala Ala Gly Gln Pro Gly Ala Lys Gly Glu Arg Gly Gly Lys Gly Pro<br>755 760 765 | 2481 | |
| aaa ggt gaa aat ggc gtt gtg gga cca act ggt cca gtg ggc gca gct<br>Lys Gly Glu Asn Gly Val Val Gly Pro Thr Gly Pro Val Gly Ala Ala<br>770 775 780 785 | 2529 | |
| gga cct gct ggt cca aat gga cca cca gga cca gca ggt agt aga gga<br>Gly Pro Ala Gly Pro Asn Gly Pro Pro Gly Pro Ala Gly Ser Arg Gly<br>790 795 800 | 2577 | |

-continued

| | |
|---|---|
| gat ggt gga cct cca gga atg aca ggt ttt cca ggt gct gct ggt aga<br>Asp Gly Gly Pro Pro Gly Met Thr Gly Phe Pro Gly Ala Ala Gly Arg<br>805 810 815 | 2625 |
| aca gga cct cct ggt cct agt ggt att tct ggt cca cca gga cca cca<br>Thr Gly Pro Pro Gly Pro Ser Gly Ile Ser Gly Pro Pro Gly Pro Pro<br>820 825 830 | 2673 |
| ggt cct gct gga aaa gaa gga ttg agg ggt cca cgt ggt gat caa gga<br>Gly Pro Ala Gly Lys Glu Gly Leu Arg Gly Pro Arg Gly Asp Gln Gly<br>835 840 845 | 2721 |
| cca gtg ggc aga act ggt gaa gtt ggc gca gtg gga cca cct ggt ttt<br>Pro Val Gly Arg Thr Gly Glu Val Gly Ala Val Gly Pro Pro Gly Phe<br>850 855 860 865 | 2769 |
| gct gga gaa aag ggc cct tct gga gag gca gga aca gct ggt cct cct<br>Ala Gly Glu Lys Gly Pro Ser Gly Glu Ala Gly Thr Ala Gly Pro Pro<br>870 875 880 | 2817 |
| ggt aca cct gga cct caa gga ctt ttg ggt gca cct ggt att ctc gga<br>Gly Thr Pro Gly Pro Gln Gly Leu Leu Gly Ala Pro Gly Ile Leu Gly<br>885 890 895 | 2865 |
| ttg cca gga agt agg ggc gaa cgt gga ctt cct ggc gtg gca gga gca<br>Leu Pro Gly Ser Arg Gly Glu Arg Gly Leu Pro Gly Val Ala Gly Ala<br>900 905 910 | 2913 |
| gtt gga gaa cct ggc cct ctc gga atc gca ggc cca cca ggc gca aga<br>Val Gly Glu Pro Gly Pro Leu Gly Ile Ala Gly Pro Pro Gly Ala Arg<br>915 920 925 | 2961 |
| gga cca cca gga gct gtt gga tca cca ggc gtg aat ggt gca cct ggc<br>Gly Pro Pro Gly Ala Val Gly Ser Pro Gly Val Asn Gly Ala Pro Gly<br>930 935 940 945 | 3009 |
| gag gct ggt cgt gat gga aac cca gga aat gat ggc cca cca gga aga<br>Glu Ala Gly Arg Asp Gly Asn Pro Gly Asn Asp Gly Pro Pro Gly Arg<br>950 955 960 | 3057 |
| gat ggt caa cct gga cac aaa ggc gag agg ggc tac cca gga aat att<br>Asp Gly Gln Pro Gly His Lys Gly Glu Arg Gly Tyr Pro Gly Asn Ile<br>965 970 975 | 3105 |
| ggc cca gtt ggt gct gct ggc gca cca ggc cca cac ggt cca gtt gga<br>Gly Pro Val Gly Ala Ala Gly Ala Pro Gly Pro His Gly Pro Val Gly<br>980 985 990 | 3153 |
| cca gca gga aaa cac ggt aat cgt ggc gaa aca ggc cct tca ggc cca<br>Pro Ala Gly Lys His Gly Asn Arg Gly Glu Thr Gly Pro Ser Gly Pro<br>995 1000 1005 | 3201 |
| gtg gga cct gct ggt gct gtt ggc cca aga gga cca tct gga cct<br>Val Gly Pro Ala Gly Ala Val Gly Pro Arg Gly Pro Ser Gly Pro<br>1010 1015 1020 | 3246 |
| caa ggc att aga ggc gat aag gga gag cct ggc gaa aaa gga cct<br>Gln Gly Ile Arg Gly Asp Lys Gly Glu Pro Gly Glu Lys Gly Pro<br>1025 1030 1035 | 3291 |
| aga ggc ttg cct ggt ttt aaa gga cac aac ggt ctc caa gga ctt<br>Arg Gly Leu Pro Gly Phe Lys Gly His Asn Gly Leu Gln Gly Leu<br>1040 1045 1050 | 3336 |
| cca ggt atc gct ggt cat cat gga gat cag ggt gct cct gga tca<br>Pro Gly Ile Ala Gly His His Gly Asp Gln Gly Ala Pro Gly Ser<br>1055 1060 1065 | 3381 |
| gtg ggt cca gca ggt cct aga ggc cca gca ggc cct tcc ggt cca<br>Val Gly Pro Ala Gly Pro Arg Gly Pro Ala Gly Pro Ser Gly Pro<br>1070 1075 1080 | 3426 |
| gca gga aag gat gga cgt act ggc cac cct gga act gtg ggc cct<br>Ala Gly Lys Asp Gly Arg Thr Gly His Pro Gly Thr Val Gly Pro<br>1085 1090 1095 | 3471 |
| gct gga att aga ggt cct caa ggt cat cag ggc cct gct ggc cct<br>Ala Gly Ile Arg Gly Pro Gln Gly His Gln Gly Pro Ala Gly Pro<br>1100 1105 1110 | 3516 |

| | | | | | | | | | | | | | | |
|---|---|---|---|---|---|---|---|---|---|---|---|---|---|---|
| cca | ggt | cca | cca | ggt | cct | cca | ggc | cca | cca | gga | gtt | tca | ggt | ggt | 3561 |
| Pro | Gly | Pro | Pro | Gly | Pro | Pro | Gly | Pro | Pro | Gly | Val | Ser | Gly | Gly | |
| 1115 | | | | 1120 | | | | | 1125 | | | | | | |

| ggt | tac | gat | ttt | ggt | tac | gat | ggt | gat | ttt | tac | cgt | gct | gat | caa | 3606 |
| Gly | Tyr | Asp | Phe | Gly | Tyr | Asp | Gly | Asp | Phe | Tyr | Arg | Ala | Asp | Gln | |
| 1130 | | | | 1135 | | | | | 1140 | | | | | | |

| cct | aga | agt | gct | cct | tct | ctc | cgt | cct | aaa | gat | tat | gaa | gtt | gat | 3651 |
| Pro | Arg | Ser | Ala | Pro | Ser | Leu | Arg | Pro | Lys | Asp | Tyr | Glu | Val | Asp | |
| 1145 | | | | 1150 | | | | | 1155 | | | | | | |

| gct | act | ttg | aaa | tca | ctt | aac | aac | cag | att | gag | act | ctt | ctc | aca | 3696 |
| Ala | Thr | Leu | Lys | Ser | Leu | Asn | Asn | Gln | Ile | Glu | Thr | Leu | Leu | Thr | |
| 1160 | | | | 1165 | | | | | 1170 | | | | | | |

| cct | gag | gga | tca | aga | aag | aat | cca | gca | cgt | aca | tgc | cgt | gat | ctc | 3741 |
| Pro | Glu | Gly | Ser | Arg | Lys | Asn | Pro | Ala | Arg | Thr | Cys | Arg | Asp | Leu | |
| 1175 | | | | 1180 | | | | | 1185 | | | | | | |

| aga | ctt | agt | cac | cca | gag | tgg | tca | agt | ggc | tat | tat | tgg | att | gat | 3786 |
| Arg | Leu | Ser | His | Pro | Glu | Trp | Ser | Ser | Gly | Tyr | Tyr | Trp | Ile | Asp | |
| 1190 | | | | 1195 | | | | | 1200 | | | | | | |

| cct | aat | cag | ggt | tgt | aca | atg | gag | gct | atc | aaa | gtt | tac | tgt | gat | 3831 |
| Pro | Asn | Gln | Gly | Cys | Thr | Met | Glu | Ala | Ile | Lys | Val | Tyr | Cys | Asp | |
| 1205 | | | | 1210 | | | | | 1215 | | | | | | |

| ttt | cca | act | gga | gag | aca | tgt | att | agg | gca | caa | cct | gag | aac | att | 3876 |
| Phe | Pro | Thr | Gly | Glu | Thr | Cys | Ile | Arg | Ala | Gln | Pro | Glu | Asn | Ile | |
| 1220 | | | | 1225 | | | | | 1230 | | | | | | |

| cca | gct | aaa | aat | tgg | tat | cgt | tcc | tct | aaa | gat | aag | aaa | cat | gtt | 3921 |
| Pro | Ala | Lys | Asn | Trp | Tyr | Arg | Ser | Ser | Lys | Asp | Lys | Lys | His | Val | |
| 1235 | | | | 1240 | | | | | 1245 | | | | | | |

| tgg | ctc | gga | gag | act | att | aac | gct | ggt | tct | cag | ttc | gag | tat | aat | 3966 |
| Trp | Leu | Gly | Glu | Thr | Ile | Asn | Ala | Gly | Ser | Gln | Phe | Glu | Tyr | Asn | |
| 1250 | | | | 1255 | | | | | 1260 | | | | | | |

| gtt | gag | ggc | gtt | act | tct | aaa | gag | atg | gca | act | cag | ctc | gct | ttt | 4011 |
| Val | Glu | Gly | Val | Thr | Ser | Lys | Glu | Met | Ala | Thr | Gln | Leu | Ala | Phe | |
| 1265 | | | | 1270 | | | | | 1275 | | | | | | |

| atg | aga | ttg | ctc | gct | aac | tac | gca | tcc | caa | aac | atc | act | tat | cac | 4056 |
| Met | Arg | Leu | Leu | Ala | Asn | Tyr | Ala | Ser | Gln | Asn | Ile | Thr | Tyr | His | |
| 1280 | | | | 1285 | | | | | 1290 | | | | | | |

| tgc | aaa | aat | tcc | att | gca | tat | atg | gat | gag | gag | aca | gga | aat | ttg | 4101 |
| Cys | Lys | Asn | Ser | Ile | Ala | Tyr | Met | Asp | Glu | Glu | Thr | Gly | Asn | Leu | |
| 1295 | | | | 1300 | | | | | 1305 | | | | | | |

| aag | aaa | gca | gtt | att | ctc | caa | ggt | agt | aac | gat | gtt | gag | ctt | gtg | 4146 |
| Lys | Lys | Ala | Val | Ile | Leu | Gln | Gly | Ser | Asn | Asp | Val | Glu | Leu | Val | |
| 1310 | | | | 1315 | | | | | 1320 | | | | | | |

| gct | gag | gga | aat | agt | aga | ttc | act | tac | aca | gtt | ttg | gtg | gat | gga | 4191 |
| Ala | Glu | Gly | Asn | Ser | Arg | Phe | Thr | Tyr | Thr | Val | Leu | Val | Asp | Gly | |
| 1325 | | | | 1330 | | | | | 1335 | | | | | | |

| tgc | tca | aag | aaa | act | aat | gag | tgg | ggc | aag | aca | atc | att | gag | tac | 4236 |
| Cys | Ser | Lys | Lys | Thr | Asn | Glu | Trp | Gly | Lys | Thr | Ile | Ile | Glu | Tyr | |
| 1340 | | | | 1345 | | | | | 1350 | | | | | | |

| aag | aca | aat | aag | cct | tct | agg | ctc | cca | ttt | ctc | gat | att | gca | cct | 4281 |
| Lys | Thr | Asn | Lys | Pro | Ser | Arg | Leu | Pro | Phe | Leu | Asp | Ile | Ala | Pro | |
| 1355 | | | | 1360 | | | | | 1365 | | | | | | |

| ctt | gat | atc | gga | gga | gct | gat | cac | gag | ttt | ttt | gtt | gat | atc | gga | 4326 |
| Leu | Asp | Ile | Gly | Gly | Ala | Asp | His | Glu | Phe | Phe | Val | Asp | Ile | Gly | |
| 1370 | | | | 1375 | | | | | 1380 | | | | | | |

| cct | gtt | tgt | ttt | aag | taa | tgagctcgcg | gccgcatc | | | | | | | | 4362 |
| Pro | Val | Cys | Phe | Lys | | | | | | | | | | | |
| 1385 | | | | | | | | | | | | | | | |

<210> SEQ ID NO 6
<211> LENGTH: 1389
<212> TYPE: PRT

<213> ORGANISM: Artificial sequence
<220> FEATURE:
<223> OTHER INFORMATION: Synthetic Construct

<400> SEQUENCE: 6

```
Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ser Thr Leu Ala Gln Leu Leu
            35                  40                  45

Gln Glu Glu Thr Val Arg Lys Gly Pro Ala Gly Asp Arg Gly Pro Arg
50                      55                  60

Gly Glu Arg Gly Pro Pro Gly Pro Gly Arg Asp Gly Glu Asp Gly
65                  70                  75                  80

Pro Thr Gly Pro Pro Gly Pro Pro Gly Pro Pro Gly Pro Pro Gly Leu
                85                  90                  95

Gly Gly Asn Phe Ala Ala Gln Tyr Asp Gly Lys Gly Val Gly Leu Gly
                100                 105                 110

Pro Gly Pro Met Gly Leu Met Gly Pro Arg Gly Pro Pro Gly Ala Ala
                115                 120                 125

Gly Ala Pro Gly Pro Gln Gly Phe Gln Gly Pro Ala Gly Glu Pro Gly
                130                 135                 140

Glu Pro Gly Gln Thr Gly Pro Ala Gly Ala Arg Gly Pro Ala Gly Pro
145                     150                 155                 160

Pro Gly Lys Ala Gly Glu Asp Gly His Pro Gly Lys Pro Gly Arg Pro
                165                 170                 175

Gly Glu Arg Gly Val Val Gly Pro Gln Gly Ala Arg Gly Phe Pro Gly
                180                 185                 190

Thr Pro Gly Leu Pro Gly Phe Lys Gly Ile Arg Gly His Asn Gly Leu
                195                 200                 205

Asp Gly Leu Lys Gly Gln Pro Gly Ala Pro Gly Val Lys Gly Glu Pro
210                     215                 220

Gly Ala Pro Gly Glu Asn Gly Thr Pro Gly Gln Thr Gly Ala Arg Gly
225                     230                 235                 240

Leu Pro Gly Glu Arg Gly Arg Val Gly Ala Pro Gly Pro Ala Gly Ala
                245                 250                 255

Arg Gly Ser Asp Gly Ser Val Gly Pro Val Gly Pro Ala Gly Pro Ile
                260                 265                 270

Gly Ser Ala Gly Pro Pro Gly Phe Pro Gly Ala Pro Gly Pro Lys Gly
                275                 280                 285

Glu Ile Gly Ala Val Gly Asn Ala Gly Pro Thr Gly Pro Ala Gly Pro
                290                 295                 300

Arg Gly Glu Val Gly Leu Pro Gly Leu Ser Gly Pro Val Gly Pro Pro
305                     310                 315                 320

Gly Asn Pro Gly Ala Asn Gly Leu Thr Gly Ala Lys Gly Ala Ala Gly
                325                 330                 335

Leu Pro Gly Val Ala Gly Ala Pro Gly Leu Pro Gly Pro Arg Gly Ile
                340                 345                 350

Pro Gly Pro Val Gly Ala Ala Gly Ala Thr Gly Ala Arg Gly Leu Val
                355                 360                 365

Gly Glu Pro Gly Pro Ala Gly Ser Lys Gly Glu Ser Gly Asn Lys Gly
                370                 375                 380

Glu Pro Gly Ser Ala Gly Pro Gln Gly Pro Pro Gly Pro Ser Gly Glu
385                     390                 395                 400
```

```
Glu Gly Lys Arg Gly Pro Asn Gly Glu Ala Gly Ser Ala Gly Pro Pro
            405                 410                 415
Gly Pro Pro Gly Leu Arg Gly Ser Pro Gly Ser Arg Gly Leu Pro Gly
        420                 425                 430
Ala Asp Gly Arg Ala Gly Val Met Gly Pro Pro Gly Ser Arg Gly Ala
            435                 440                 445
Ser Gly Pro Ala Gly Val Arg Gly Pro Asn Gly Asp Ala Gly Arg Pro
        450                 455                 460
Gly Glu Pro Gly Leu Met Gly Pro Arg Gly Leu Pro Gly Ser Pro Gly
465                 470                 475                 480
Asn Ile Gly Pro Ala Gly Lys Glu Gly Pro Val Gly Leu Pro Gly Ile
                485                 490                 495
Asp Gly Arg Pro Gly Pro Ile Gly Pro Ala Gly Ala Arg Gly Glu Pro
            500                 505                 510
Gly Asn Ile Gly Phe Pro Gly Pro Lys Gly Pro Thr Gly Asp Pro Gly
        515                 520                 525
Lys Asn Gly Asp Lys Gly His Ala Gly Leu Ala Gly Ala Arg Gly Ala
        530                 535                 540
Pro Gly Pro Asp Gly Asn Asn Gly Ala Gln Gly Pro Pro Gly Pro Gln
545                 550                 555                 560
Gly Val Gln Gly Gly Lys Gly Glu Gln Gly Pro Ala Gly Pro Pro Gly
                565                 570                 575
Phe Gln Gly Leu Pro Gly Pro Ser Gly Pro Ala Gly Glu Val Gly Lys
            580                 585                 590
Pro Gly Glu Arg Gly Leu His Gly Glu Phe Gly Leu Pro Gly Pro Ala
        595                 600                 605
Gly Pro Arg Gly Glu Arg Gly Pro Pro Gly Glu Ser Gly Ala Ala Gly
        610                 615                 620
Pro Thr Gly Pro Ile Gly Ser Arg Gly Pro Ser Gly Pro Pro Gly Pro
625                 630                 635                 640
Asp Gly Asn Lys Gly Glu Pro Gly Val Val Gly Ala Val Gly Thr Ala
                645                 650                 655
Gly Pro Ser Gly Pro Ser Gly Leu Pro Gly Glu Arg Gly Ala Ala Gly
            660                 665                 670
Ile Pro Gly Gly Lys Gly Glu Lys Gly Glu Pro Gly Leu Arg Gly Glu
        675                 680                 685
Ile Gly Asn Pro Gly Arg Asp Gly Ala Arg Gly Ala His Gly Ala Val
        690                 695                 700
Gly Ala Pro Gly Pro Ala Gly Ala Thr Gly Asp Arg Gly Glu Ala Gly
705                 710                 715                 720
Ala Ala Gly Pro Ala Gly Pro Ala Gly Pro Arg Gly Ser Pro Gly Glu
                725                 730                 735
Arg Gly Glu Val Gly Pro Ala Gly Pro Asn Gly Phe Ala Gly Pro Ala
            740                 745                 750
Gly Ala Ala Gly Gln Pro Gly Ala Lys Gly Glu Arg Gly Gly Lys Gly
        755                 760                 765
Pro Lys Gly Glu Asn Gly Val Val Gly Pro Thr Gly Pro Val Gly Ala
        770                 775                 780
Ala Gly Pro Ala Gly Pro Asn Gly Pro Pro Gly Pro Ala Gly Ser Arg
785                 790                 795                 800
Gly Asp Gly Gly Pro Pro Gly Met Thr Gly Phe Pro Gly Ala Ala Gly
                805                 810                 815
Arg Thr Gly Pro Pro Gly Pro Ser Gly Ile Ser Gly Pro Pro Gly Pro
```

-continued

```
                820             825             830
Pro Gly Pro Ala Gly Lys Glu Gly Leu Arg Gly Pro Arg Gly Asp Gln
            835             840             845
Gly Pro Val Gly Arg Thr Gly Glu Val Gly Ala Val Gly Pro Pro Gly
            850             855             860
Phe Ala Gly Glu Lys Gly Pro Ser Gly Glu Ala Gly Thr Ala Gly Pro
865             870             875             880
Pro Gly Thr Pro Gly Pro Gln Gly Leu Leu Gly Ala Pro Gly Ile Leu
            885             890             895
Gly Leu Pro Gly Ser Arg Gly Glu Arg Gly Leu Pro Gly Val Ala Gly
            900             905             910
Ala Val Gly Glu Pro Gly Pro Leu Gly Ile Ala Gly Pro Pro Gly Ala
            915             920             925
Arg Gly Pro Pro Gly Ala Val Gly Ser Pro Gly Val Asn Gly Ala Pro
            930             935             940
Gly Glu Ala Gly Arg Asp Gly Asn Pro Gly Asn Asp Gly Pro Pro Gly
945             950             955             960
Arg Asp Gly Gln Pro Gly His Lys Gly Glu Arg Gly Tyr Pro Gly Asn
            965             970             975
Ile Gly Pro Val Gly Ala Ala Gly Ala Pro Gly Pro His Gly Pro Val
            980             985             990
Gly Pro Ala Gly Lys His Gly Asn Arg Gly Glu Thr Gly Pro Ser Gly
            995             1000            1005
Pro Val Gly Pro Ala Gly Ala Val Gly Pro Arg Gly Pro Ser Gly
    1010            1015            1020
Pro Gln Gly Ile Arg Gly Asp Lys Gly Glu Pro Gly Glu Lys Gly
    1025            1030            1035
Pro Arg Gly Leu Pro Gly Phe Lys Gly His Asn Gly Leu Gln Gly
    1040            1045            1050
Leu Pro Gly Ile Ala Gly His His Gly Asp Gln Gly Ala Pro Gly
    1055            1060            1065
Ser Val Gly Pro Ala Gly Pro Arg Gly Pro Ala Gly Pro Ser Gly
    1070            1075            1080
Pro Ala Gly Lys Asp Gly Arg Thr Gly His Pro Gly Thr Val Gly
    1085            1090            1095
Pro Ala Gly Ile Arg Gly Pro Gln Gly His Gln Gly Pro Ala Gly
    1100            1105            1110
Pro Pro Gly Pro Pro Gly Pro Gly Pro Pro Gly Val Ser Gly
    1115            1120            1125
Gly Gly Tyr Asp Phe Gly Tyr Asp Gly Asp Phe Tyr Arg Ala Asp
    1130            1135            1140
Gln Pro Arg Ser Ala Pro Ser Leu Arg Pro Lys Asp Tyr Glu Val
    1145            1150            1155
Asp Ala Thr Leu Lys Ser Leu Asn Asn Gln Ile Glu Thr Leu Leu
    1160            1165            1170
Thr Pro Glu Gly Ser Arg Lys Asn Pro Ala Arg Thr Cys Arg Asp
    1175            1180            1185
Leu Arg Leu Ser His Pro Glu Trp Ser Ser Gly Tyr Tyr Trp Ile
    1190            1195            1200
Asp Pro Asn Gln Gly Cys Thr Met Glu Ala Ile Lys Val Tyr Cys
    1205            1210            1215
Asp Phe Pro Thr Gly Glu Thr Cys Ile Arg Ala Gln Pro Glu Asn
    1220            1225            1230
```

-continued

```
Ile Pro Ala Lys Asn Trp Tyr Arg Ser Ser Lys Asp Lys Lys His
    1235                1240                1245

Val Trp Leu Gly Glu Thr Ile Asn Ala Gly Ser Gln Phe Glu Tyr
    1250                1255                1260

Asn Val Glu Gly Val Thr Ser Lys Glu Met Ala Thr Gln Leu Ala
    1265                1270                1275

Phe Met Arg Leu Leu Ala Asn Tyr Ala Ser Gln Asn Ile Thr Tyr
    1280                1285                1290

His Cys Lys Asn Ser Ile Ala Tyr Met Asp Glu Glu Thr Gly Asn
    1295                1300                1305

Leu Lys Lys Ala Val Ile Leu Gln Gly Ser Asn Asp Val Glu Leu
    1310                1315                1320

Val Ala Glu Gly Asn Ser Arg Phe Thr Tyr Thr Val Leu Val Asp
    1325                1330                1335

Gly Cys Ser Lys Lys Thr Asn Glu Trp Gly Lys Thr Ile Ile Glu
    1340                1345                1350

Tyr Lys Thr Asn Lys Pro Ser Arg Leu Pro Phe Leu Asp Ile Ala
    1355                1360                1365

Pro Leu Asp Ile Gly Gly Ala Asp His Glu Phe Val Asp Ile
    1370                1375                1380

Gly Pro Val Cys Phe Lys
    1385

<210> SEQ ID NO 7
<211> LENGTH: 127
<212> TYPE: DNA
<213> ORGANISM: Artificial sequence
<220> FEATURE:
<223> OTHER INFORMATION: Synthetic sequence containing the coding region
      of the appoplast signal of Arabidopsis thaliana endo-1,4-beta-
      glucanase and flanking regions

<400> SEQUENCE: 7
gccatggcta ggaagtcttt gattttccca gtgattcttc ttgctgtgct tcttttctct      60
ccacctattt actctgctgg acacgattat agggatgctc ttaggaagtc atctatggct     120
caattgc                                                              127

<210> SEQ ID NO 8
<211> LENGTH: 127
<212> TYPE: DNA
<213> ORGANISM: Artificial sequence
<220> FEATURE:
<223> OTHER INFORMATION: Synthetic sequence of the appoplast signal of
      Arabidopsis thaliana endo-1,4-beta-glucanase and flanking regions
<220> FEATURE:
<221> NAME/KEY: CDS
<222> LOCATION: (10)..(120)

<400> SEQUENCE: 8 gccatggct agg aag tct ttg att ttc cca gtg att ctt ctt gct gtg ctt      51
          Arg Lys Ser Leu Ile Phe Pro Val Ile Leu Leu Ala Val Leu
            1               5                   10 ctt ttc tct cca cct att tac tct gct gga cac gat tat agg gat gct       99
Leu Phe Ser Pro Pro Ile Tyr Ser Ala Gly His Asp Tyr Arg Asp Ala
 15                  20                  25                  30 ctt agg aag tca tct atg gct caattgc                                  127
Leu Arg Lys Ser Ser Met Ala
                35

<210> SEQ ID NO 9
<211> LENGTH: 37
```

```
<212> TYPE: PRT
<213> ORGANISM: Artificial sequence
<220> FEATURE:
<223> OTHER INFORMATION: Synthetic Construct

<400> SEQUENCE: 9

Arg Lys Ser Leu Ile Phe Pro Val Ile Leu Leu Ala Val Leu Leu Phe
1               5                   10                  15

Ser Pro Pro Ile Tyr Ser Ala Gly His Asp Tyr Arg Asp Ala Leu Arg
            20                  25                  30

Lys Ser Ser Met Ala
        35

<210> SEQ ID NO 10
<211> LENGTH: 1037
<212> TYPE: DNA
<213> ORGANISM: Artificial sequence
<220> FEATURE:
<223> OTHER INFORMATION: Chrysanthemum rbcS1 promoter and 5' UTR

<400> SEQUENCE: 10
aaatggcgcg ccaagcttag acaaacaccc cttgttatac aaagaatttc gctttacaaa      60
atcaaattcg agaaaataat atatgcacta ataagatca ttcggatcca atctaaccaa     120
ttacgatacg ctttgggtac acttgatttt tgtttcagta gttacatata tcttgtttta    180
tatgctatct ttaaggatct tcactcaaag actatttgtt gatgttcttg atggggctcg    240
gaagatttga tatgatacac tctaatcttt aggagatacc agccaggatt atattcagta    300
agacaatcaa attttacgtg ttcaaactcg ttatcttttc atttaatgga tgagccagaa    360
tctctataga atgattgcaa tcgagaatat gttcggccga tatcccttg ttggcttcaa     420
tattctacat atcacacaag aatcgaccgt attgtaccct ctttccataa aggaacacac    480
agtatgcaga tgcttttttc ccacatgcag taacataggt attcaaaaat ggctaaaaga    540
agttggataa caaattgaca actatttcca tttctgttat ataaatttca caacacacaa    600
aagcccgtaa tcaagagtct gcccatgtac gaaataactt ctattatttg gtattgggcc    660
taagcccagc tcagagtacg tgggggtacc acatatagga aggtaacaaa atactgcaag    720
atagccccat aacgtaccag cctctcctta ccacgaagag ataagatata agacccaccc    780
tgccacgtgt cacatcgtca tggtggttaa tgataaggga ttcatccctt ctatgtttgt    840
ggacatgatg catgtaatgt catgagccac atgatccaat ggccacagga acgtaagaat    900
gtagatagat ttgattttgt ccgttagata gcaaacaaca ttataaaagg tgtgtatcaa    960
tacgaactaa ttcactcatt ggattcatag aagtccattc ctcctaagta tctaaacata   1020
tgcaattgtc gactaaa                                                   1037

<210> SEQ ID NO 11
<211> LENGTH: 975
<212> TYPE: DNA
<213> ORGANISM: Artificial sequence
<220> FEATURE:
<223> OTHER INFORMATION: Chrysanthemum rbcS1 3'UTR and terminator

<400> SEQUENCE: 11
aaaaggatcc gcggccgcat aagtttact atttaccaag acttttgaat attaaccttc       60
ttgtaacgag tcggttaaat ttgattgttt agggttttgt attattttttt tttggtcttt    120
taattcatca ctttaattcc ctaattgtct gttcatttcg ttgtttgttt ccggatcgat    180
aatgaaatgt aagagatatc atatataaat aataaattgt cgtttcatat ttgcaatctt    240
```

| | |
|---|---|
| ttttttacaaa cctttaatta attgtatgta tgacattttc ttcttgttat attaggggga | 300 |
| aataatgtta aataaaagta caaaataaac tacagtacat cgtactgaat aaattaccta | 360 |
| gccaaaaagt acacctttcc atatacttcc tacatgaagg cattttcaac attttcaaat | 420 |
| aaggaatgct acaaccgcat aataacatcc acaaattttt ttataaaata acatgtcaga | 480 |
| cagtgattga aagattttat tatagtttcg ttatcttctt ttctcattaa gcgaatcact | 540 |
| acctaacacg tcattttgtg aaatattttt tgaatgtttt tatatagttg tagcattcct | 600 |
| cttttcaaat tagggtttgt ttgagatagc atttcagccg gttcatacaa cttaaaagca | 660 |
| tactctaatg ctggaaaaaa gactaaaaaa tcttgtaagt tagcgcagaa tattgaccca | 720 |
| aattatatac acacatgacc ccatatagag actaattaca cttttaacca ctaataatta | 780 |
| ttactgtatt ataacatcta ctaattaaac ttgtgagttt ttgctagaat tattatcata | 840 |
| tatactaaaa ggcaggaacg caaacattgc cccggtactg tagcaactac ggtagacgca | 900 |
| ttaattgtct atagtggacg cattaattaa ccaaaaccgc ctctttcccc ttcttcttga | 960 |
| agcttgagct ctttt | 975 |

<210> SEQ ID NO 12
<211> LENGTH: 1633
<212> TYPE: DNA
<213> ORGANISM: Artificial sequence
<220> FEATURE:
<223> OTHER INFORMATION: Synthetic sequence containing the coding
    regions of the vacuolar signal sequence of barley gene for Thiol
    protease aleurain precursor fused to the human Prolyl
    4-hydroxylase beta subunit and flanking regions

<400> SEQUENCE: 12

| | |
|---|---|
| ctcgagtaaa ccatggctca tgctagggtt ttgcttttgg ctcttgctgt tcttgctact | 60 |
| gctgctgttg ctgtggcttc ttcttcatct ttcgctgatt ctaacccaat taggccagtg | 120 |
| actgatagag ctgcttctac tcttgctcaa ttggtcgaca tggatgctcc agaagaggag | 180 |
| gatcacgttc ttgtgcttag gaagtctaac ttcgctgaag ctcttgctgc tcacaagtac | 240 |
| cttcttgtgg agttttatgc tccttggtgc ggacattgca aagctcttgc tccagagtat | 300 |
| gctaaggctg ctggaaagtt gaaggctgag ggatctgaaa ttaggcttgc taaagtggat | 360 |
| gctactgagg agtctgatct tgctcaacag tacggagtta ggggataccc aactattaag | 420 |
| ttcttcagga acggagatac tgcttctcca aaggagtata ctgctggaag ggaggctgat | 480 |
| gatattgtga actggcttaa gaagagaact ggaccagctg ctactactct tccagatgga | 540 |
| gctgctgctg aatctcttgt ggagtcatct gaggtggcag tgattggatt cttcaaggat | 600 |
| gtggagtctg attctgctaa gcagttcctt caagctgctg aggctattga tgatattcca | 660 |
| ttcggaatta cttctaactc tgatgtgttc tctaagtacc agcttgataa ggatggagtg | 720 |
| gtgcttttca gaaaattcga tgagggaagg aacaatttcg agggagaggt gacaaaggag | 780 |
| aaccttcttg atttcattaa gcacaaccag cttccacttg tgattgagtt cactgagcag | 840 |
| actgctccaa agattttcgg aggagagatt aagactcaca ttcttctttt ccttccaaag | 900 |
| tctgtgtctg attacgatgg aaagttgtct aacttcaaga ctgctgctga gtcttttcaag | 960 |
| ggaaagattc ttttcatttt cattgattct gatcacactg ataaccagag gattcttgag | 1020 |
| ttcttcggac ttaagaagga gagtgccca gctgttaggc ttattactct tgaggaggag | 1080 |
| atgactaagt acaagccaga gtctgaagaa cttactgctg agaggattac tgagttctgc | 1140 |
| cacagattcc ttgagggaaa gattaagcca caccttatgt ctcaagagct tccagaggat | 1200 |
| tgggataagc agccagttaa ggtgttggtg ggtaaaaact tcgaggatgt ggctttcgat | 1260 |

-continued

```
gagaagaaga acgtgttcgt ggagttctac gcaccttggt gtggtcactg taagcagctt    1320
gctccaattt gggataagtt gggagagact tacaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca agaagttcct tgagtctgga ggacaagatg gagctggaga tgatgatgat    1560
cttgaggatt tggaagaagc tgaggagcca gatatggagg aggatgatga tcagaaggct    1620
gtgtgatgag ctc                                                      1633
```

```
<210> SEQ ID NO 13
<211> LENGTH: 537
<212> TYPE: PRT
<213> ORGANISM: Artificial sequence
<220> FEATURE:
<223> OTHER INFORMATION: Synthetic sequence containing the vacuolar
      signal sequence of barley gene for Thiol protease aleurain
      precursor fused to the human Prolyl 4-hydroxylase beta subunit and
      flanking regions

<400> SEQUENCE: 13
```

```
Met Ala His Ala Arg Val Leu Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala Gln Leu Val
        35                  40                  45

Asp Met Asp Ala Pro Glu Glu Glu Asp His Val Leu Val Leu Arg Lys
    50                  55                  60

Ser Asn Phe Ala Glu Ala Leu Ala Ala His Lys Tyr Leu Leu Val Glu
65                  70                  75                  80

Phe Tyr Ala Pro Trp Cys Gly His Cys Lys Ala Leu Ala Pro Glu Tyr
                85                  90                  95

Ala Lys Ala Ala Gly Lys Leu Lys Ala Glu Gly Ser Glu Ile Arg Leu
            100                 105                 110

Ala Lys Val Asp Ala Thr Glu Glu Ser Asp Leu Ala Gln Gln Tyr Gly
        115                 120                 125

Val Arg Gly Tyr Pro Thr Ile Lys Phe Phe Arg Asn Gly Asp Thr Ala
    130                 135                 140

Ser Pro Lys Glu Tyr Thr Ala Gly Arg Glu Ala Asp Asp Ile Val Asn
145                 150                 155                 160

Trp Leu Lys Lys Arg Thr Gly Pro Ala Ala Thr Thr Leu Pro Asp Gly
                165                 170                 175

Ala Ala Ala Glu Ser Leu Val Glu Ser Ser Glu Val Ala Val Ile Gly
            180                 185                 190

Phe Phe Lys Asp Val Glu Ser Asp Ser Ala Lys Gln Phe Leu Gln Ala
        195                 200                 205

Ala Glu Ala Ile Asp Asp Ile Pro Phe Gly Ile Thr Ser Asn Ser Asp
    210                 215                 220

Val Phe Ser Lys Tyr Gln Leu Asp Lys Asp Gly Val Val Leu Phe Lys
225                 230                 235                 240

Lys Phe Asp Glu Gly Arg Asn Asn Phe Glu Gly Glu Val Thr Lys Glu
                245                 250                 255

Asn Leu Leu Asp Phe Ile Lys His Asn Gln Leu Pro Leu Val Ile Glu
            260                 265                 270

Phe Thr Glu Gln Thr Ala Pro Lys Ile Phe Gly Gly Glu Ile Lys Thr
```

```
                                275                 280                 285
His Ile Leu Leu Phe Leu Pro Lys Ser Val Ser Asp Tyr Asp Gly Lys
        290                 295                 300

Leu Ser Asn Phe Lys Thr Ala Ala Glu Ser Phe Lys Gly Lys Ile Leu
305                 310                 315                 320

Phe Ile Phe Ile Asp Ser Asp His Thr Asp Asn Gln Arg Ile Leu Glu
                325                 330                 335

Phe Phe Gly Leu Lys Lys Glu Glu Cys Pro Ala Val Arg Leu Ile Thr
                340                 345                 350

Leu Glu Glu Glu Met Thr Lys Tyr Lys Pro Glu Ser Glu Glu Leu Thr
        355                 360                 365

Ala Glu Arg Ile Thr Glu Phe Cys His Arg Phe Leu Glu Gly Lys Ile
        370                 375                 380

Lys Pro His Leu Met Ser Gln Glu Leu Pro Glu Asp Trp Asp Lys Gln
385                 390                 395                 400

Pro Val Lys Val Leu Val Gly Lys Asn Phe Glu Asp Val Ala Phe Asp
                405                 410                 415

Glu Lys Lys Asn Val Phe Val Glu Phe Tyr Ala Pro Trp Cys Gly His
                420                 425                 430

Cys Lys Gln Leu Ala Pro Ile Trp Asp Lys Leu Gly Glu Thr Tyr Lys
        435                 440                 445

Asp His Glu Asn Ile Val Ile Ala Lys Met Asp Ser Thr Ala Asn Glu
        450                 455                 460

Val Glu Ala Val Lys Val His Ser Phe Pro Thr Leu Lys Phe Phe Pro
465                 470                 475                 480

Ala Ser Ala Asp Arg Thr Val Ile Asp Tyr Asn Gly Glu Arg Thr Leu
                485                 490                 495

Asp Gly Phe Lys Lys Phe Leu Glu Ser Gly Gly Gln Asp Gly Ala Gly
                500                 505                 510

Asp Asp Asp Asp Leu Glu Asp Leu Glu Glu Ala Glu Glu Pro Asp Met
        515                 520                 525

Glu Glu Asp Asp Asp Gln Lys Ala Val
    530                 535

<210> SEQ ID NO 14
<211> LENGTH: 1723
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Prolyl
      4-hydroxylase alpha-1 subunit and flanking regions

<400> SEQUENCE: 14
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg     120
actgatagag ctgcttctac tcttgctcaa ttggtcgaca tgcacccagg attcttcact     180
tctattggac agatgactga tcttattcac actgagaagg atcttgtgac ttctcttaag     240
gattacatta aggctgagga ggataagttg gagcagatta agaagtgggc tgagaagttg     300
gataggctta cttctactgc tacaaaagat ccagagggat cgttggtca tccagtgaac     360 gctttcaagt tgatgaagag gcttaacact gagtggagtg agcttgagaa ccttgtgctt     420
aaggatatgt ctgatggatt catttctaac cttactattc agaggcagta cttcccaaat     480
gatgaggatc aagtgggagc tgctaaggct cttcttaggc ttcaggatac ttacaacctt     540
```

```
gatactgata caatttctaa gggaaacctt ccaggagtta agcacaagtc tttccttact      600
gctgaggatt gcttcgagct tggaaaggtt gcatacactg aggctgatta ctaccacact      660
gagctttgga tggaacaagc tcttaggcaa cttgatgagg agagatttc tactattgat       720 aaggtgtcag tgcttgatta ccttcttac gctgtgtacc agcagggtga tcttgataag       780
gctcttttgc ttactaagaa gttgcttgag cttgatccag aacatcagag ggctaacgga      840
aaccttaagt acttcgagta cattatggct aaggaaaagg atgtgaacaa gtctgcttct      900
gatgatcagt ctgatcaaaa gactactcca agaagaagg gagtggctgt tgattatctt       960
cctgagaggc agaagtatga gatgttgtgt aggggagagg gtattaagat gactccaagg     1020
aggcagaaga agttgttctg caggtatcac gatggaaaca ggaacccaaa gttcattctt     1080
gctccagcta agcaagaaga tgagtgggat aagccaagga ttattaggtt ccacgatatt     1140
atttctgatg ctgagattga gattgtgaag gatcttgcta agccaagact taggagggct     1200
actatttcta accctattac tggtgatctt gagactgtgc actacaggat ttctaagtct     1260
gcttggcttt ctggatacga gaacccagtg gtgtctagga ttaacatgag gattcaggat     1320
cttactggac ttgatgtgtc tactgctgag gagcttcaag ttgctaacta cggagttgga     1380
ggacaatatg agccacactt cgatttcgct aggaaggatg agccagatgc ttttaaggag     1440
cttggaactg gaaacaggat tgctacttgg ctttttctaca tgtctgatgt ttctgctgga     1500
ggagctactg ttttcccaga agtgggagct tctgtttggc aaagaagg aactgctgtg      1560 ttctggtaca acctttttcgc ttctggagag ggagattact ctactaggca tgctgcttgc     1620
ccagttcttg ttggaaacaa gtgggtgtca acaagtggc ttcatgagag gggacaagag     1680
tttagaaggc catgcactct ttctgagctt gagtgatgag ctc                        1723
```

<210> SEQ ID NO 15
<211> LENGTH: 567
<212> TYPE: PRT
<213> ORGANISM: Artificial sequence
<220> FEATURE:
<223> OTHER INFORMATION: Synthetic sequence containing the vacuolar
      signal sequence of barley gene for Thiol protease aleurain
      precursor fused to the human Prolyl 4-hydroxylase alpha-1 subunit
      and flanking regions

<400> SEQUENCE: 15

```
Met Ala His Ala Arg Val Leu Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala Gln Leu Val
        35                  40                  45

Asp Met His Pro Gly Phe Phe Thr Ser Ile Gly Gln Met Thr Asp Leu
    50                  55                  60

Ile His Thr Glu Lys Asp Leu Val Thr Ser Leu Lys Asp Tyr Ile Lys
65                  70                  75                  80

Ala Glu Glu Asp Lys Leu Glu Gln Ile Lys Lys Trp Ala Glu Lys Leu
                85                  90                  95

Asp Arg Leu Thr Ser Thr Ala Thr Lys Asp Pro Glu Gly Phe Val Gly
            100                 105                 110

His Pro Val Asn Ala Phe Lys Leu Met Lys Arg Leu Asn Thr Glu Trp
        115                 120                 125

Ser Glu Leu Glu Asn Leu Val Leu Lys Asp Met Ser Asp Gly Phe Ile
    130                 135                 140
```

```
Ser Asn Leu Thr Ile Gln Arg Gln Tyr Phe Pro Asn Asp Glu Asp Gln
145                 150                 155                 160

Val Gly Ala Ala Lys Ala Leu Leu Arg Leu Gln Asp Thr Tyr Asn Leu
                165                 170                 175

Asp Thr Asp Thr Ile Ser Lys Gly Asn Leu Pro Gly Val Lys His Lys
            180                 185                 190

Ser Phe Leu Thr Ala Glu Asp Cys Phe Glu Leu Gly Lys Val Ala Tyr
        195                 200                 205

Thr Glu Ala Asp Tyr Tyr His Thr Glu Leu Trp Met Glu Gln Ala Leu
    210                 215                 220

Arg Gln Leu Asp Glu Gly Glu Ile Ser Thr Ile Asp Lys Val Ser Val
225                 230                 235                 240

Leu Asp Tyr Leu Ser Tyr Ala Val Tyr Gln Gln Gly Asp Leu Asp Lys
                245                 250                 255

Ala Leu Leu Leu Thr Lys Lys Leu Leu Glu Leu Asp Pro Glu His Gln
            260                 265                 270

Arg Ala Asn Gly Asn Leu Lys Tyr Phe Glu Tyr Ile Met Ala Lys Glu
        275                 280                 285

Lys Asp Val Asn Lys Ser Ala Ser Asp Asp Gln Ser Asp Gln Lys Thr
    290                 295                 300

Thr Pro Lys Lys Gly Val Ala Val Asp Tyr Leu Pro Glu Arg Gln
305                 310                 315                 320

Lys Tyr Glu Met Leu Cys Arg Gly Glu Gly Ile Lys Met Thr Pro Arg
                325                 330                 335

Arg Gln Lys Lys Leu Phe Cys Arg Tyr His Asp Gly Asn Arg Asn Pro
            340                 345                 350

Lys Phe Ile Leu Ala Pro Ala Lys Gln Glu Asp Glu Trp Asp Lys Pro
        355                 360                 365

Arg Ile Ile Arg Phe His Asp Ile Ile Ser Asp Ala Glu Ile Glu Ile
    370                 375                 380

Val Lys Asp Leu Ala Lys Pro Arg Leu Arg Arg Ala Thr Ile Ser Asn
385                 390                 395                 400

Pro Ile Thr Gly Asp Leu Glu Thr Val His Tyr Arg Ile Ser Lys Ser
                405                 410                 415

Ala Trp Leu Ser Gly Tyr Glu Asn Pro Val Val Ser Arg Ile Asn Met
            420                 425                 430

Arg Ile Gln Asp Leu Thr Gly Leu Asp Val Ser Thr Ala Glu Glu Leu
        435                 440                 445

Gln Val Ala Asn Tyr Gly Val Gly Gly Gln Tyr Glu Pro His Phe Asp
    450                 455                 460

Phe Ala Arg Lys Asp Glu Pro Asp Ala Phe Lys Glu Leu Gly Thr Gly
465                 470                 475                 480

Asn Arg Ile Ala Thr Trp Leu Phe Tyr Met Ser Asp Val Ser Ala Gly
                485                 490                 495

Gly Ala Thr Val Phe Pro Glu Val Gly Ala Ser Val Trp Pro Lys Lys
            500                 505                 510

Gly Thr Ala Val Phe Trp Tyr Asn Leu Phe Ala Ser Gly Glu Gly Asp
        515                 520                 525

Tyr Ser Thr Arg His Ala Ala Cys Pro Val Leu Val Gly Asn Lys Trp
    530                 535                 540

Val Ser Asn Lys Trp Leu His Glu Arg Gly Gln Glu Phe Arg Arg Pro
545                 550                 555                 560

Cys Thr Leu Ser Glu Leu Glu
```

<210> SEQ ID NO 16
<211> LENGTH: 928
<212> TYPE: DNA
<213> ORGANISM: Artificial sequence
<220> FEATURE:
<223> OTHER INFORMATION: Synthetic sequence containing the coding
regions of the vacuolar signal sequence of barley gene for Thiol
protease aleurain precursor fused to the plant Prolyl
4-hydroxylase Plant and flanking regions

<400> SEQUENCE: 16

```
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg     120
actgatagag ctgcttctac tcttgctcaa ttggtcgaca tgcttggtat tctttctctt     180
ccaaacgcta acaggaactc ttctaagact aacgatctta ctaacattgt gaggaagtct     240
gagacttctt ctggagatga ggagggaaat ggagaaagat gggtggaagt gatttcttgg     300
gagccaaggg ctgttgttta ccacaacttc cttactaatg aggagtgcga gcaccttatt     360
tctcttgcta agccatctat ggtgaagtct actgtggtgg atgagaaaac tggaggatct     420
aaggattcaa gagtgaggac ttcatctggt actttcctta ggaggggaca tgatgaagtt     480
gtggaagtta ttgagaagag gatttctgat ttcactttca ttccagtgga aacggagaa      540
ggacttcaag ttcttcacta ccaagtggga caaaagtacg agccacacta cgattacttc     600
cttgatgagt tcaacactaa gaacggagga cagaggattg ctactgtgct tatgtacctt     660
tctgatgtgg atgatggagg agagactgtt tttccagctg ctaggggaaa catttctgct     720
gttccttggt ggaacgagct ttctaagtgt ggaaaggagg gactttctgt gcttccaaag     780
aaaagggatg ctcttctttt ctggaacatg aggccagatg cttctcttga tccatcttct     840
cttcatggag gatgcccagt tgttaaggga aacaagtggt catctactaa gtggttccac     900
gtgcacgagt tcaaggtgta atgagctc                                         928
```

<210> SEQ ID NO 17
<211> LENGTH: 302
<212> TYPE: PRT
<213> ORGANISM: Artificial sequence
<220> FEATURE:
<223> OTHER INFORMATION: Synthetic sequence containing the vacuolar
signal sequence of barley gene for Thiol protease aleurain
precursor fused to the plant Prolyl 4-hydroxylase Plant and
flanking regions

<400> SEQUENCE: 17

```
Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
                20                  25                  30

Ile Arg Pro Val Thr Asp Arg Ala Ala Ser Thr Leu Ala Gln Leu Val
            35                  40                  45

Asp Met Leu Gly Ile Leu Ser Leu Pro Asn Ala Asn Arg Asn Ser Ser
        50                  55                  60

Lys Thr Asn Asp Leu Thr Asn Ile Val Arg Lys Ser Glu Thr Ser Ser
65                  70                  75                  80

Gly Asp Glu Glu Gly Asn Gly Glu Arg Trp Val Glu Val Ile Ser Trp
                85                  90                  95

Glu Pro Arg Ala Val Val Tyr His Asn Phe Leu Thr Asn Glu Glu Cys
            100                 105                 110
```

Glu His Leu Ile Ser Leu Ala Lys Pro Ser Met Val Lys Ser Thr Val
            115                 120                 125

Val Asp Glu Lys Thr Gly Gly Ser Lys Asp Ser Arg Val Arg Thr Ser
    130                 135                 140

Ser Gly Thr Phe Leu Arg Arg Gly His Asp Glu Val Val Glu Val Ile
145                 150                 155                 160

Glu Lys Arg Ile Ser Asp Phe Thr Phe Ile Pro Val Glu Asn Gly Glu
                165                 170                 175

Gly Leu Gln Val Leu His Tyr Gln Val Gly Gln Lys Tyr Glu Pro His
            180                 185                 190

Tyr Asp Tyr Phe Leu Asp Glu Phe Asn Thr Lys Asn Gly Gly Gln Arg
            195                 200                 205

Ile Ala Thr Val Leu Met Tyr Leu Ser Asp Val Asp Asp Gly Gly Glu
            210                 215                 220

Thr Val Phe Pro Ala Ala Arg Gly Asn Ile Ser Ala Val Pro Trp Trp
225                 230                 235                 240

Asn Glu Leu Ser Lys Cys Gly Lys Glu Gly Leu Ser Val Leu Pro Lys
                245                 250                 255

Lys Arg Asp Ala Leu Leu Phe Trp Asn Met Arg Pro Asp Ala Ser Leu
            260                 265                 270

Asp Pro Ser Ser Leu His Gly Gly Cys Pro Val Val Lys Gly Asn Lys
            275                 280                 285

Trp Ser Ser Thr Lys Trp Phe His Val His Glu Phe Lys Val
290                 295                 300

<210> SEQ ID NO 18
<211> LENGTH: 2689
<212> TYPE: DNA
<213> ORGANISM: Artificial sequence
<220> FEATURE:
<223> OTHER INFORMATION: Synthetic sequence containing the coding
      regions of the human Procollagen C-proteinase and flanking regions

<400> SEQUENCE: 18
agatctatcg atgcatgcca tggtaccgcg ccatggctca attggctgca acatcaaggc      60
ctgaaagagt ttggccagat ggtgttattc ctttcgttat tggtggaaac tttactggat     120
ctcagagagc agttttttaga caagctatga cattggga aaagcacact tgtgtgacat      180
tccttgaaag gactgatgaa gattcttata ttgtgttcac ataccgtcca tgtggatgct     240
gctcatatgt tggtagaagg ggaggaggtc acaagcaatt tctattgga aaaaactgcg      300 ataagttcgg aattgtggtg catgaattgg acatgttgt tggtttctgg cacgaacaca     360
caaggccaga tagggatagg cacgtgtcta ttgtgaggga aaacattcag ccaggtcaag     420
agtacaattt tcttaagatg aacctcaag aggtggaatc tctcggagag acttacgact     480
tcgactccat catgcactac gcaaggaata ctttcagcag gggcatcttc ttggatacca     540
ttgtgcctaa gtacgaggtg aacggcgtta agccacctat tggtcaaagg actaggctct     600
ctaagggtga tattgcacag gctaggaagc tctacaaatg tccagcatgc ggagaaactc     660
ttcaggattc cactggcaac ttctcatctc cagagtaccc aaacggatac tctgctcata     720
tgcactgtgt ttgaggatc tcagtgactc ctggagagaa gatcatcctc aacttcactt     780
ccctcgatct ctatcgttct aggctctgtt ggtacgacta tgtggaagtg agagatggct     840
tctggagaaa ggctccactt agaggaaggt tctgcggatc taaacttcct gagccaatcg     900
tgtctactga ttccagattg tgggtggagt tcaggtcctc ttctaattgg gttggcaagg     960

-continued

```
gcttttttgc tgtgtacgag gctatttgtg gcggcgacgt gaaaaaggac tacggacata    1020
ttcaaagtcc aaattaccca gatgattacc gtccttcaaa agtgtgtatt tggaggattc    1080
aagtgagtga gggtttccat gttggattga cattccaatc tttcgaaatt gagagacacg    1140
attcatgcgc atacgattat ttggaagtga gagatggaca ctctgaatct tctacactta    1200
ttggaaggta ctgcggttat gagaaacctg atgatattaa gtctacttct agtaggttgt    1260
ggcttaaatt tgtgtcagat ggttctatta caaggctggt tttcgcagtg aacttcttca    1320
aggaagtgga tgaatgctca agacctaaca gaggaggatg tgagcaaaga tgccttaaca    1380
ctttgggaag ttacaagtgt tcttgcgatc tggatacga gttggctcct gataagagaa     1440
gatgcgaagc tgcttgcggt ggttttttga caaaattgaa cggatctatt acttctcctg    1500
gatggccaaa agagtaccca cctaataaga attgcatttg gcagcttgtt gcacctactc    1560
agtaccgtat ttcattgcaa ttcgattttt tcgagactga gggtaatgat gtgtgcaagt    1620
acgatttcgt ggaagtgaga tcaggtctta ctgctgatag taaattgcac ggaaagttct    1680
gcggatctga aaaccagaa gtgattacat cacagtacaa caatatgagg gtggagttca     1740
aatctgataa tactgtttct aaaaaaggtt ttaaggcaca tttctttttct gataaggacg    1800 agtgctctaa agataatggt ggttgccagc aggattgcgt gaacacattc ggttcatatg    1860
agtgccaatg ccgtagtgga tttgttcttc acgataacaa acatgattgc aaagaggcag    1920
gttgcgatca aaggtgaca tctacttcag gtactatcac atctccaaac tggcctgata     1980
agtatccttc aaaaaaagaa tgtacatggg caatttcttc tacaccaggt catagggtta    2040
agttgacatt catggagatg gatattgaga gtcaaccaga gtgcgcttat gatcatcttg    2100
aggtgttcga tggaagggat gctaaggctc ctgttcttgg tagattctgt ggtagtaaaa    2160
agccagaacc agtgcttgca acaggatcta ggatgttcct tagattctac tctgataact    2220
cagttcagag gaaaggattc caagctagtc acgcaactga atgcggtgga caagttagag    2280
cagatgttaa gactaaggat ctttactcac acgcacagtt cggagataac aactaccctg    2340
gaggagttga ttgcgagtgg gttattgtgg ctgaagaggg atacggagtt gagcttgttt    2400
tccagacatt cgaggtggag gaggaaactg attgcggtta cgattatatg gaacttttttg    2460 atggatacga tagtactgct ccaagacttg gaaggtattg tggtagtggt ccaccagaag    2520
aggtgtactc agctggagat agtgttcttg ttaagttcca cagtgatgat acaattacta    2580
agaagggatt ccatcttaga tatacttcaa ctaagtttca ggatactctt cattctagga    2640
agtaatgagc tcgcggccgc atccaagctt ctgcagacgc gtcgacgtc                2689
```

<210> SEQ ID NO 19
<211> LENGTH: 870
<212> TYPE: PRT
<213> ORGANISM: Artificial sequence
<220> FEATURE:
<223> OTHER INFORMATION: Synthetic sequence containing the human
      Procollagen C-proteinase and flanking regions

<400> SEQUENCE: 19

Met Ala Gln Leu Ala Ala Thr Ser Arg Pro Glu Arg Val Trp Pro Asp
1               5                   10                  15

Gly Val Ile Pro Phe Val Ile Gly Gly Asn Phe Thr Gly Ser Gln Arg
            20                  25                  30

Ala Val Phe Arg Gln Ala Met Arg His Trp Glu Lys His Thr Cys Val
        35                  40                  45

Thr Phe Leu Glu Arg Thr Asp Glu Asp Ser Tyr Ile Val Phe Thr Tyr
    50                  55                  60

-continued

```
Arg Pro Cys Gly Cys Cys Ser Tyr Val Gly Arg Gly Gly Pro
 65                  70                  75                  80

Gln Ala Ile Ser Ile Gly Lys Asn Cys Asp Lys Phe Gly Ile Val Val
                 85                  90                  95

His Glu Leu Gly His Val Gly Phe Trp His Glu His Thr Arg Pro
            100                 105                 110

Asp Arg Asp Arg His Val Ser Ile Val Arg Glu Asn Ile Gln Pro Gly
            115                 120                 125

Gln Glu Tyr Asn Phe Leu Lys Met Glu Pro Gln Glu Val Glu Ser Leu
        130                 135                 140

Gly Glu Thr Tyr Asp Phe Asp Ser Ile Met His Tyr Ala Arg Asn Thr
145                 150                 155                 160

Phe Ser Arg Gly Ile Phe Leu Asp Thr Ile Val Pro Lys Tyr Glu Val
                165                 170                 175

Asn Gly Val Lys Pro Pro Ile Gly Gln Arg Thr Arg Leu Ser Lys Gly
            180                 185                 190

Asp Ile Ala Gln Ala Arg Lys Leu Tyr Lys Cys Pro Ala Cys Gly Glu
        195                 200                 205

Thr Leu Gln Asp Ser Thr Gly Asn Phe Ser Ser Pro Glu Tyr Pro Asn
210                 215                 220

Gly Tyr Ser Ala His Met His Cys Val Trp Arg Ile Ser Val Thr Pro
225                 230                 235                 240

Gly Glu Lys Ile Ile Leu Asn Phe Thr Ser Leu Asp Leu Tyr Arg Ser
                245                 250                 255

Arg Leu Cys Trp Tyr Asp Tyr Val Glu Val Arg Asp Gly Phe Trp Arg
            260                 265                 270

Lys Ala Pro Leu Arg Gly Arg Phe Cys Gly Ser Lys Leu Pro Glu Pro
        275                 280                 285

Ile Val Ser Thr Asp Ser Arg Leu Trp Val Glu Phe Arg Ser Ser Ser
290                 295                 300

Asn Trp Val Gly Lys Gly Phe Phe Ala Val Tyr Glu Ala Ile Cys Gly
305                 310                 315                 320

Gly Asp Val Lys Lys Asp Tyr Gly His Ile Gln Ser Pro Asn Tyr Pro
                325                 330                 335

Asp Asp Tyr Arg Pro Ser Lys Val Cys Ile Trp Arg Ile Gln Val Ser
            340                 345                 350

Glu Gly Phe His Val Gly Leu Thr Phe Gln Ser Phe Glu Ile Glu Arg
        355                 360                 365

His Asp Ser Cys Ala Tyr Asp Tyr Leu Glu Val Arg Asp Gly His Ser
370                 375                 380

Glu Ser Ser Thr Leu Ile Gly Arg Tyr Cys Gly Tyr Glu Lys Pro Asp
385                 390                 395                 400

Asp Ile Lys Ser Thr Ser Ser Arg Leu Trp Leu Lys Phe Val Ser Asp
                405                 410                 415

Gly Ser Ile Asn Lys Ala Gly Phe Ala Val Asn Phe Phe Lys Glu Val
            420                 425                 430

Asp Glu Cys Ser Arg Pro Asn Arg Gly Gly Cys Glu Gln Arg Cys Leu
        435                 440                 445

Asn Thr Leu Gly Ser Tyr Lys Cys Ser Cys Asp Pro Gly Tyr Glu Leu
450                 455                 460

Ala Pro Asp Lys Arg Arg Cys Glu Ala Ala Cys Gly Gly Phe Leu Thr
465                 470                 475                 480

Lys Leu Asn Gly Ser Ile Thr Ser Pro Gly Trp Pro Lys Glu Tyr Pro
```

```
                    485                 490                 495
Pro Asn Lys Asn Cys Ile Trp Gln Leu Val Ala Pro Thr Gln Tyr Arg
            500                 505                 510

Ile Ser Leu Gln Phe Asp Phe Glu Thr Glu Gly Asn Asp Val Cys
        515                 520                 525

Lys Tyr Asp Phe Val Glu Val Arg Ser Gly Leu Thr Ala Asp Ser Lys
            530                 535                 540

Leu His Gly Lys Phe Cys Gly Ser Glu Lys Pro Glu Val Ile Thr Ser
545                 550                 555                 560

Gln Tyr Asn Asn Met Arg Val Glu Phe Lys Ser Asp Asn Thr Val Ser
                565                 570                 575

Lys Lys Gly Phe Lys Ala His Phe Phe Ser Asp Lys Asp Glu Cys Ser
            580                 585                 590

Lys Asp Asn Gly Gly Cys Gln Gln Asp Cys Val Asn Thr Phe Gly Ser
        595                 600                 605

Tyr Glu Cys Gln Cys Arg Ser Gly Phe Val Leu His Asp Asn Lys His
        610                 615                 620

Asp Cys Lys Glu Ala Gly Cys Asp His Lys Val Thr Ser Thr Ser Gly
625                 630                 635                 640

Thr Ile Thr Ser Pro Asn Trp Pro Asp Lys Tyr Pro Ser Lys Lys Glu
                645                 650                 655

Cys Thr Trp Ala Ile Ser Ser Thr Pro Gly His Arg Val Lys Leu Thr
            660                 665                 670

Phe Met Glu Met Asp Ile Glu Ser Gln Pro Glu Cys Ala Tyr Asp His
        675                 680                 685

Leu Glu Val Phe Asp Gly Arg Asp Ala Lys Ala Pro Val Leu Gly Arg
        690                 695                 700

Phe Cys Gly Ser Lys Lys Pro Glu Pro Val Leu Ala Thr Gly Ser Arg
705                 710                 715                 720

Met Phe Leu Arg Phe Tyr Ser Asp Asn Ser Val Gln Arg Lys Gly Phe
                725                 730                 735

Gln Ala Ser His Ala Thr Glu Cys Gly Gly Gln Val Arg Ala Asp Val
            740                 745                 750

Lys Thr Lys Asp Leu Tyr Ser His Ala Gln Phe Gly Asp Asn Asn Tyr
        755                 760                 765

Pro Gly Gly Val Asp Cys Glu Trp Val Ile Val Ala Glu Glu Gly Tyr
        770                 775                 780

Gly Val Glu Leu Val Phe Gln Thr Phe Glu Val Glu Glu Glu Thr Asp
785                 790                 795                 800

Cys Gly Tyr Asp Tyr Met Glu Leu Phe Asp Gly Tyr Asp Ser Thr Ala
                805                 810                 815

Pro Arg Leu Gly Arg Tyr Cys Gly Ser Gly Pro Pro Glu Glu Val Tyr
            820                 825                 830

Ser Ala Gly Asp Ser Val Leu Val Lys Phe His Ser Asp Asp Thr Ile
        835                 840                 845

Thr Lys Lys Gly Phe His Leu Arg Tyr Thr Ser Thr Lys Phe Gln Asp
        850                 855                 860

Thr Leu His Ser Arg Lys
865                 870

<210> SEQ ID NO 20
<211> LENGTH: 2912
<212> TYPE: DNA
<213> ORGANISM: Artificial sequence
<220> FEATURE:
```

<223> OTHER INFORMATION: Synthetic sequence containing the coding regions of the human Procollagen I N-proteinase and flanking regions

<400> SEQUENCE: 20

| | | | | | |
|---|---|---|---|---|---|
| gcgccatggc | tcaattgagg | agaagggcta | ggagacacgc | agctgatgat | gattacaaca | 60 |
| ttgaagtttt | gcttggtgtt | gatgatagtg | tggtgcaatt | ccacggaaaa | gagcatgttc | 120 |
| agaaatatct | tttgacactt | atgaatattg | tgaacgaaat | ctaccatgat | gagtctttgg | 180 |
| gagcacacat | taacgtggtt | cttgtgagga | ttattcttct | ttcatacggt | aaatctatgt | 240 |
| cacttattga | gattggaaac | ccttctcagt | ctcttgagaa | tgtgtgcaga | tgggcatacc | 300 |
| ttcaacagaa | gcctgatact | ggacacgatg | agtatcacga | tcacgctatt | tccttacaa | 360 |
| ggcaggattt | cggtccaagt | ggaatgcaag | gatatgctcc | tgttactggt | atgtgccacc | 420 |
| ctgttaggtc | ttgtacactt | aaccacgagg | atggttttc | atctgctttc | gtggtggctc | 480 |
| atgagacagg | tcatgttttg | ggaatggaac | atgatggaca | gggtaataga | tgtggagatg | 540 |
| aagtgagact | tggttcaatt | atggctcctc | ttgttcaagc | tgcttttcat | aggttccact | 600 |
| ggagtaggtt | ttcacagcaa | gagttgagta | gataccttca | ttcttacgat | tgcttgcttg | 660 |
| atgatccatt | tgctcatgat | tggccagctt | tgcctcaact | tcctggattg | cactactcta | 720 |
| tgaacgagca | gtgcagattt | gatttcggtc | ttggttacat | gatgtgcaca | gctttcagga | 780 |
| ctttcgatcc | atgcaaacag | ttgtggtgtt | cacacccaga | taacccatat | ttctgtaaaa | 840 |
| caaaaaagg | tccaccactt | gatggtacta | tgtgcgcacc | tggaaagcac | tgcttcaagg | 900 |
| gacactgcat | ttggcttact | cctgatattc | ttaaaaggga | tggatcatgg | ggagcttggt | 960 |
| ctccattcgg | aagttgctca | agaacttgcg | gaacaggtgt | taagtttaga | actaggcagt | 1020 |
| gcgataatcc | acaccctgct | aatggtggta | gaacttgctc | tggacttgct | tacgattttc | 1080 |
| agttgtgttc | taggcaagat | tgccctgata | gtcttgctga | ttttagagaa | gagcaatgta | 1140 |
| gacagtggga | tctttacttt | gagcacggcg | acgctcagca | ccactggctt | ccacacgagc | 1200 |
| atagagatgc | aaaagaaagg | tgtcaccttt | attgcgagag | tagagagact | ggagaggtgg | 1260 |
| tgtcaatgaa | gagaatggtg | cacgatggta | caaggtgttc | ttataaggat | gcattctctt | 1320 |
| tgtgtgtgag | gggagattgc | aggaaagtgg | gttgtgatgg | agtgattgga | tctagtaagc | 1380 |
| aagaagataa | gtgcggagtg | tgcggaggag | ataactctca | ttgcaaggtt | gtgaaaggaa | 1440 |
| cttttacaag | atcaccaaaa | aaacacggtt | acattaagat | gttcgaaatt | cctgctggag | 1500 |
| caaggcattt | gcttattcag | gaagtggatg | caacatctca | ccacttggca | gtgaaaaacc | 1560 |
| ttgagactgg | aaaattcatt | ttgaacgagg | agaacgatgt | tgatgcatct | agtaagactt | 1620 |
| tcattgcaat | gggtgttgaa | tgggagtata | gggatgagga | tggaagggaa | acacttcaaa | 1680 |
| caatgggtcc | tcttcatgga | acaattactg | tgttggtgat | tccagtggga | gatacaaggg | 1740 |
| tgtcattgac | atacaagtat | atgattcacg | aggatagtct | taacgttgat | gataacaacg | 1800 |
| ttttggaaga | agattctgtg | gtttacgagt | gggctcttaa | gaaatggtca | ccttgctcta | 1860 |
| agccatgtgg | tggaggaagt | cagttcacta | gtatggttg | taggaggagg | cttgatcata | 1920 |
| agatggttca | tagggatttt | gcgcagcac | ttagtaagcc | aaaggcaatt | aggagggctt | 1980 |
| gtaaccctca | agaatgctca | caaccagttt | gggtgacagg | agagtgggag | ccatgttcac | 2040 |
| aaacatgcgg | aagaactgga | atgcaagtta | gatcagttag | atgcattcaa | cctcttcatg | 2100 |
| ataacactac | aagaagtgtg | cacgcaaaac | actgtaacga | tgctaggcca | gagagtagaa | 2160 |
| gagcttgctc | tagggaactt | tgccctggta | gatggagggc | aggaccttgg | agtcagtgct | 2220 |

-continued

```
ctgtgacatg tggaaacggt actcaggaaa gacctgttcc atgtagaact gctgatgata    2280
gtttcggaat ttgtcaggag gaaaggccag aaacagctag gacttgtaga cttggacctt    2340
gtcctaggaa tatttctgat cctagtaaaa aatcatacgt ggtgcaatgg ttgagtaggc    2400
cagatccaga ttcaccaatt aggaagattt cttcaaaagg acactgccag ggtgataaga    2460
gtattttctg cagaatggaa gttcttagta ggtactgttc tattccaggt tataacaaac    2520
tttcttgtaa gagttgcaac ttgtataaca atcttactaa cgtggagggt agaattgaac    2580
ctccaccagg aaagcacaac gatattgatg tgtttatgcc tactcttcct gtgccaacag    2640
ttgcaatgga agttagacct tctccatcta ctccacttga ggtgccactt aatgcatcaa    2700
gtactaacgc tactgaggat cacccagaga ctaacgcagt tgatgagcct tataagattc    2760
acggacttga ggatgaggtt cagccaccaa accttattcc taggaggcca agtccttacg    2820
aaaaaactag aaatcagagg attcaggagc ttattgatga gatgaggaaa aaggagatgc    2880
ttggaaagtt ctaatgagct cgcggccgca tc                                 2912
```

<210> SEQ ID NO 21
<211> LENGTH: 962
<212> TYPE: PRT
<213> ORGANISM: Artificial sequence
<220> FEATURE:
<223> OTHER INFORMATION: Synthetic sequence containing the human
      Procollagen I N-proteinase and flanking regions

<400> SEQUENCE: 21

```
Met Ala Gln Leu Arg Arg Arg Ala Arg Arg His Ala Ala Asp Asp Asp
1               5                   10                  15

Tyr Asn Ile Glu Val Leu Leu Gly Val Asp Asp Ser Val Val Gln Phe
            20                  25                  30

His Gly Lys Glu His Val Gln Lys Tyr Leu Leu Thr Leu Met Asn Ile
        35                  40                  45

Val Asn Glu Ile Tyr His Asp Glu Ser Leu Gly Ala His Ile Asn Val
    50                  55                  60

Val Leu Val Arg Ile Ile Leu Leu Ser Tyr Gly Lys Ser Met Ser Leu
65                  70                  75                  80

Ile Glu Ile Gly Asn Pro Ser Gln Ser Leu Glu Asn Val Cys Arg Trp
                85                  90                  95

Ala Tyr Leu Gln Gln Lys Pro Asp Thr Gly His Asp Glu Tyr His Asp
            100                 105                 110

His Ala Ile Phe Leu Thr Arg Gln Asp Phe Gly Pro Ser Gly Met Gln
        115                 120                 125

Gly Tyr Ala Pro Val Thr Gly Met Cys His Pro Val Arg Ser Cys Thr
    130                 135                 140

Leu Asn His Glu Asp Gly Phe Ser Ser Ala Phe Val Val Ala His Glu
145                 150                 155                 160

Thr Gly His Val Leu Gly Met Glu His Asp Gly Gln Gly Asn Arg Cys
                165                 170                 175

Gly Asp Glu Val Arg Leu Gly Ser Ile Met Ala Pro Leu Val Gln Ala
            180                 185                 190

Ala Phe His Arg Phe His Trp Ser Arg Cys Ser Gln Gln Glu Leu Ser
        195                 200                 205

Arg Tyr Leu His Ser Tyr Asp Cys Leu Leu Asp Asp Pro Phe Ala His
    210                 215                 220

Asp Trp Pro Ala Leu Pro Gln Leu Pro Gly Leu His Tyr Ser Met Asn
225                 230                 235                 240
```

```
Glu Gln Cys Arg Phe Asp Phe Gly Leu Gly Tyr Met Met Cys Thr Ala
            245                 250                 255

Phe Arg Thr Phe Asp Pro Cys Lys Gln Leu Trp Cys Ser His Pro Asp
        260                 265                 270

Asn Pro Tyr Phe Cys Lys Thr Lys Gly Pro Pro Leu Asp Gly Thr
            275                 280                 285

Met Cys Ala Pro Gly Lys His Cys Phe Lys Gly His Cys Ile Trp Leu
    290                 295                 300

Thr Pro Asp Ile Leu Lys Arg Asp Gly Ser Trp Gly Ala Trp Ser Pro
305                 310                 315                 320

Phe Gly Ser Cys Ser Arg Thr Cys Gly Thr Gly Val Lys Phe Arg Thr
            325                 330                 335

Arg Gln Cys Asp Asn Pro His Pro Ala Asn Gly Gly Arg Thr Cys Ser
            340                 345                 350

Gly Leu Ala Tyr Asp Phe Gln Leu Cys Ser Arg Gln Asp Cys Pro Asp
            355                 360                 365

Ser Leu Ala Asp Phe Arg Glu Gln Cys Arg Gln Trp Asp Leu Tyr
    370                 375                 380

Phe Glu His Gly Asp Ala Gln His His Trp Leu Pro His Glu His Arg
385                 390                 395                 400

Asp Ala Lys Glu Arg Cys His Leu Tyr Cys Glu Ser Arg Glu Thr Gly
                405                 410                 415

Glu Val Val Ser Met Lys Arg Met Val His Asp Gly Thr Arg Cys Ser
            420                 425                 430

Tyr Lys Asp Ala Phe Ser Leu Cys Val Arg Gly Asp Cys Arg Lys Val
        435                 440                 445

Gly Cys Asp Gly Val Ile Gly Ser Ser Lys Gln Glu Asp Lys Cys Gly
    450                 455                 460

Val Cys Gly Gly Asp Asn Ser His Cys Lys Val Val Lys Gly Thr Phe
465                 470                 475                 480

Thr Arg Ser Pro Lys Lys His Gly Tyr Ile Lys Met Phe Glu Ile Pro
                485                 490                 495

Ala Gly Ala Arg His Leu Leu Ile Gln Glu Val Asp Ala Thr Ser His
            500                 505                 510

His Leu Ala Val Lys Asn Leu Glu Thr Gly Lys Phe Ile Leu Asn Glu
    515                 520                 525

Glu Asn Asp Val Asp Ala Ser Ser Lys Thr Phe Ile Ala Met Gly Val
    530                 535                 540

Glu Trp Glu Tyr Arg Asp Glu Asp Gly Arg Glu Thr Leu Gln Thr Met
545                 550                 555                 560

Gly Pro Leu His Gly Thr Ile Thr Val Leu Val Ile Pro Val Gly Asp
                565                 570                 575

Thr Arg Val Ser Leu Thr Tyr Lys Tyr Met Ile His Glu Asp Ser Leu
            580                 585                 590

Asn Val Asp Asp Asn Asn Val Leu Glu Glu Asp Ser Val Val Tyr Glu
        595                 600                 605

Trp Ala Leu Lys Lys Trp Ser Pro Cys Ser Lys Pro Cys Gly Gly Gly
    610                 615                 620

Ser Gln Phe Thr Lys Tyr Gly Cys Arg Arg Leu Asp His Lys Met
625                 630                 635                 640

Val His Arg Gly Phe Cys Ala Ala Leu Ser Lys Pro Lys Ala Ile Arg
                645                 650                 655

Arg Ala Cys Asn Pro Gln Glu Cys Ser Gln Pro Val Trp Val Thr Gly
            660                 665                 670
```

Glu Trp Glu Pro Cys Ser Gln Thr Cys Gly Arg Thr Gly Met Gln Val
             675                 680                 685

Arg Ser Val Arg Cys Ile Gln Pro Leu His Asp Asn Thr Thr Arg Ser
690                 695                 700

Val His Ala Lys His Cys Asn Asp Ala Arg Pro Glu Ser Arg Arg Ala
705                 710                 715                 720

Cys Ser Arg Glu Leu Cys Pro Gly Arg Trp Arg Ala Gly Pro Trp Ser
             725                 730                 735

Gln Cys Ser Val Thr Cys Gly Asn Gly Thr Gln Glu Arg Pro Val Pro
             740                 745                 750

Cys Arg Thr Ala Asp Asp Ser Phe Gly Ile Cys Gln Glu Glu Arg Pro
             755                 760                 765

Glu Thr Ala Arg Thr Cys Arg Leu Gly Pro Cys Pro Arg Asn Ile Ser
             770                 775                 780

Asp Pro Ser Lys Lys Ser Tyr Val Val Gln Trp Leu Ser Arg Pro Asp
785                 790                 795                 800

Pro Asp Ser Pro Ile Arg Lys Ile Ser Ser Lys Gly His Cys Gln Gly
             805                 810                 815

Asp Lys Ser Ile Phe Cys Arg Met Glu Val Leu Ser Arg Tyr Cys Ser
             820                 825                 830

Ile Pro Gly Tyr Asn Lys Leu Ser Cys Lys Ser Cys Asn Leu Tyr Asn
             835                 840                 845

Asn Leu Thr Asn Val Glu Gly Arg Ile Glu Pro Pro Gly Lys His
850                 855                 860

Asn Asp Ile Asp Val Phe Met Pro Thr Leu Pro Val Pro Thr Val Ala
865                 870                 875                 880

Met Glu Val Arg Pro Ser Pro Ser Thr Pro Leu Glu Val Pro Leu Asn
             885                 890                 895

Ala Ser Ser Thr Asn Ala Thr Glu Asp His Pro Glu Thr Asn Ala Val
             900                 905                 910

Asp Glu Pro Tyr Lys Ile His Gly Leu Glu Asp Glu Val Gln Pro Pro
             915                 920                 925

Asn Leu Ile Pro Arg Arg Pro Ser Pro Tyr Glu Lys Thr Arg Asn Gln
             930                 935                 940

Arg Ile Gln Glu Leu Ile Asp Glu Met Arg Lys Lys Glu Met Leu Gly
945                 950                 955                 960

Lys Phe

<210> SEQ ID NO 22
<211> LENGTH: 2888
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Lysyl hydroxylase 3
      and flanking regions

<400> SEQUENCE: 22
gcgaattcgc tagctatcac tgaaaagaca gcaagacaat ggtgtctcga tgcaccagaa     60
ccacatcttt gcagcagatg tgaagcagcc agagtggtcc acaagacgca ctcagaaaag    120
gcatcttcta ccgacacaga aaagacaaac cacagctcat catccaacat gtagactgtc    180
gttatgcgtc ggctgaagat aagactgacc ccaggccagc actaaagaag aaataatgca    240
agtggtccta gctccacttt agctttaata attatgtttc attattattc tctgcttttg    300

```
ctctctatat aaagagcttg tattttcatt tgaaggcaga ggcgaacaca cacacagaac    360
ctccctgctt acaaaccaga tcttaaacca tggctcacgc tagggttttg cttcttgctc    420
ttgctgttct tgctactgct gctgttgctg tggcttcttc aagttctttc gctgattcta    480
acccaattag gccagtgact gatagagctg cttctactct tgctcaattg agatctatgt    540
ctgatagacc aaggggaagg gatccagtta atccagagaa gttgcttgtg attactgtgg    600
ctactgctga gactgaagga taccttagat tccttaggag tgctgagttc ttcaactaca    660
ctgtgaggac tcttggactt ggagaagaat ggaggggagg agatgttgct agaactgttg    720
gaggaggaca gaaagtgaga tggcttaaga aagagatgga gaagtacgct ataggggagg    780
atatgattat tatgttcgtg gattcttacg atgtgattct tgctggatct ccaactgagc    840
ttttgaagaa attcgttcag tctggatcta ggcttctttt ctctgctgag tcttttttgtt   900
ggccagaatg gggacttgct gagcaatatc agaagtgggg aactggaaag agattcctta    960
actctggagg attcattgga ttcgctacta ctattcacca gattgtgagg cagtggaagt   1020
acaaggatga cgatgatgat cagcttttct acactaggct ttaccttgat ccaggactta   1080
gggagaagtt gtctcttaac cttgatcaca agtctaggat tttccagaac cttaacggtg   1140
ctcttgatga ggttgtgctt aagttcgata ggaacagagt gaggattagg aacgtggctt   1200
acgatactct tcctattgtg gtgcatggaa acggaccaac aaaactccag cttaactacc   1260
ttggaaacta cgttccaaac ggatggactc cagaaggagg atgtggattc tgcaatcagg   1320
ataggagaac tcttccagga ggacaaccac caccaagagt tttccttgct gtgttcgttg   1380
aacagccaac tccattcctt ccaagattcc ttcagaggct tcttctttt gattacccac    1440
cagatagggt gacacttttc cttcacaaca acgaggtttt ccacgagcca cacattgctg   1500
attcttggcc acagcttcag gatcatttct ctgctgtgaa gttggttggt ccagaagaag   1560
ctctttctcc aggagaagct agggatatgg ctatggattt gtgcaggcag atccagagt    1620
gcgagttcta cttctctctt gatgctgatg ctgtgcttac taaccttcag actcttagga   1680
ttccttattga ggagaacagg aaagtgattg ctccaatgct ttctaggcac ggaaagttgt   1740
ggtctaattt ctggggtgct cttttctcctg atgagtacta cgctagatca gaggactacg   1800
tggagcttgt tcagagaaag agagtgggag tttggaacgt tccttatatt tctcaggctt   1860
acgtgattag gggagatact cttaggatgg agcttccaca gagggatgtt ttctctggat   1920
ctgatactga tccagatatg gctttctgca gtctttcag ggataaggga attttccttc    1980
accttcctaa ccagcatgag ttcggaagat tgcttgctac ttcaagatac gatactgagc   2040
accttcatcc tgatctttgg cagattttcg ataaccccagt ggattggaag gagcagtaca   2100
ttcacgagaa ctactctagg gctcttgaag gagaaggaat tgtggagcaa ccatgcccag   2160
atgtttactg gttcccactt ctttctgagc aaatgtgcga tgagcttgtt gctgagatgg   2220
agcattacga caatggagt ggaggtagac atgaggattc taggcttgct ggaggatacg    2280
agaacgttcc aactgtggat attcacatga agcaagtggg atacgaggat caatggcttc   2340
agcttcttag gacttatgtg ggaccaatga ctgagtctct tttcccagga taccacacta   2400
aggctagggc tgttatgaac ttcgttgtga ggtatcgtcc agatgagcaa ccatctctta   2460
ggccacacca cgattcttct actttcactc ttaacgtggc tcttaaccac aagggacttg   2520
attatgaggg aggaggatgc cgtttcctta gatacgattg cgtgatttct tcaccaagaa   2580
agggatgggc tcttcttcat ccaggaaggc ttactcatta ccacgaggga cttccaacta   2640
cttggggaac tagatatatt atggtgtctt tcgtggatcc atgactgctt taatgagata   2700
```

```
tgcgagacgc ctatgatcgc atgatatttg ctttcaattc tgttgtgcac gttgtaaaaa    2760
acctgagcat gtgtagctca gatccttacc gccggtttcg gttcattcta atgaatatat    2820
cacccgttac tatcgtattt ttatgaataa tattctccgt tcaatttact gattgtccag    2880
aattcgcg                                                              2888
```

<210> SEQ ID NO 23
<211> LENGTH: 764
<212> TYPE: PRT
<213> ORGANISM: Artificial sequence
<220> FEATURE:
<223> OTHER INFORMATION: Synthetic sequence containing the vacuolar
    signal sequence of barley gene for Thiol protease aleurain
    precursor fused to the human Lysyl hydroxylase 3 and flanking
    regions

<400> SEQUENCE: 23

```
Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
                20                  25                  30

Ile Arg Pro Val Thr Asp Arg Ala Ala Ser Thr Leu Ala Gln Leu Arg
            35                  40                  45

Ser Met Ser Asp Arg Pro Arg Gly Arg Asp Pro Val Asn Pro Glu Lys
50                  55                  60

Leu Leu Val Ile Thr Val Ala Thr Ala Glu Thr Gly Tyr Leu Arg
65                  70                  75                  80

Phe Leu Arg Ser Ala Glu Phe Phe Asn Tyr Thr Val Arg Thr Leu Gly
                85                  90                  95

Leu Gly Glu Glu Trp Arg Gly Gly Asp Val Ala Arg Thr Val Gly Gly
            100                 105                 110

Gly Gln Lys Val Arg Trp Leu Lys Lys Glu Met Glu Lys Tyr Ala Asp
        115                 120                 125

Arg Glu Asp Met Ile Ile Met Phe Val Asp Ser Tyr Asp Val Ile Leu
    130                 135                 140

Ala Gly Ser Pro Thr Glu Leu Leu Lys Lys Phe Val Gln Ser Gly Ser
145                 150                 155                 160

Arg Leu Leu Phe Ser Ala Glu Ser Phe Cys Trp Pro Glu Trp Gly Leu
                165                 170                 175

Ala Glu Gln Tyr Pro Glu Val Gly Thr Gly Lys Arg Phe Leu Asn Ser
            180                 185                 190

Gly Gly Phe Ile Gly Phe Ala Thr Thr Ile His Gln Ile Val Arg Gln
        195                 200                 205

Trp Lys Tyr Lys Asp Asp Asp Asp Gln Leu Phe Tyr Thr Arg Leu
    210                 215                 220

Tyr Leu Asp Pro Gly Leu Arg Glu Lys Leu Ser Leu Asn Leu Asp His
225                 230                 235                 240

Lys Ser Arg Ile Phe Gln Asn Leu Asn Gly Ala Leu Asp Glu Val Val
                245                 250                 255

Leu Lys Phe Asp Arg Asn Arg Val Arg Ile Arg Asn Val Ala Tyr Asp
            260                 265                 270

Thr Leu Pro Ile Val Val His Gly Asn Gly Pro Thr Lys Leu Gln Leu
        275                 280                 285

Asn Tyr Leu Gly Asn Tyr Val Pro Asn Gly Trp Thr Pro Glu Gly Gly
    290                 295                 300

Cys Gly Phe Cys Asn Gln Asp Arg Arg Thr Leu Pro Gly Gly Gln Pro
305                 310                 315                 320
```

```
Pro Pro Arg Val Phe Leu Ala Val Phe Val Glu Gln Pro Thr Pro Phe
            325                 330                 335

Leu Pro Arg Phe Leu Gln Arg Leu Leu Leu Asp Tyr Pro Pro Asp
            340                 345                 350

Arg Val Thr Leu Phe Leu His Asn Asn Glu Val Phe His Glu Pro His
            355                 360                 365

Ile Ala Asp Ser Trp Pro Gln Leu Gln Asp His Phe Ser Ala Val Lys
370                 375                 380

Leu Val Gly Pro Glu Glu Ala Leu Ser Pro Gly Glu Ala Arg Asp Met
385                 390                 395                 400

Ala Met Asp Leu Cys Arg Gln Asp Pro Glu Cys Glu Phe Tyr Phe Ser
                405                 410                 415

Leu Asp Ala Asp Ala Val Leu Thr Asn Leu Gln Thr Leu Arg Ile Leu
            420                 425                 430

Ile Glu Glu Asn Arg Lys Val Ile Ala Pro Met Leu Ser Arg His Gly
            435                 440                 445

Lys Leu Trp Ser Asn Phe Trp Gly Ala Leu Ser Pro Asp Glu Tyr Tyr
    450                 455                 460

Ala Arg Ser Glu Asp Tyr Val Glu Leu Val Gln Arg Lys Arg Val Gly
465                 470                 475                 480

Val Trp Asn Val Pro Tyr Ile Ser Gln Ala Tyr Val Ile Arg Gly Asp
                485                 490                 495

Thr Leu Arg Met Glu Leu Pro Gln Arg Asp Val Phe Ser Gly Ser Asp
            500                 505                 510

Thr Asp Pro Asp Met Ala Phe Cys Lys Ser Phe Arg Asp Lys Gly Ile
            515                 520                 525

Phe Leu His Leu Ser Asn Gln His Glu Phe Gly Arg Leu Leu Ala Thr
            530                 535                 540

Ser Arg Tyr Asp Thr Glu His Leu His Pro Asp Leu Trp Gln Ile Phe
545                 550                 555                 560

Asp Asn Pro Val Asp Trp Lys Glu Gln Tyr Ile His Glu Asn Tyr Ser
                565                 570                 575

Arg Ala Leu Glu Gly Glu Gly Ile Val Glu Gln Pro Cys Pro Asp Val
            580                 585                 590

Tyr Trp Phe Pro Leu Leu Ser Glu Gln Met Cys Asp Glu Leu Val Ala
            595                 600                 605

Glu Met Glu His Tyr Gly Gln Trp Ser Gly Gly Arg His Glu Asp Ser
            610                 615                 620

Arg Leu Ala Gly Gly Tyr Glu Asn Val Pro Thr Val Asp Ile His Met
625                 630                 635                 640

Lys Gln Val Gly Tyr Glu Asp Gln Trp Leu Gln Leu Leu Arg Thr Tyr
                645                 650                 655

Val Gly Pro Met Thr Glu Ser Leu Phe Pro Gly Tyr His Thr Lys Ala
            660                 665                 670

Arg Ala Val Met Asn Phe Val Val Arg Tyr Arg Pro Asp Glu Gln Pro
            675                 680                 685

Ser Leu Arg Pro His His Asp Ser Ser Thr Phe Thr Leu Asn Val Ala
            690                 695                 700

Leu Asn His Lys Gly Leu Asp Tyr Glu Gly Gly Gly Cys Arg Phe Leu
705                 710                 715                 720

Arg Tyr Asp Cys Val Ile Ser Ser Pro Arg Lys Gly Trp Ala Leu Leu
                725                 730                 735

His Pro Gly Arg Leu Thr His Tyr His Glu Gly Leu Pro Thr Thr Trp
```

```
                    740                 745                 750
Gly Thr Arg Tyr Ile Met Val Ser Phe Val Asp Pro
        755                 760

<210> SEQ ID NO 24
<211> LENGTH: 45
<212> TYPE: PRT
<213> ORGANISM: Artificial sequence
<220> FEATURE:
<223> OTHER INFORMATION: Vacuole signal sequence of barley gene for
      Thiol protease aleurain precursor

<400> SEQUENCE: 24

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala
        35                  40                  45

<210> SEQ ID NO 25
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 25
atcaccagga gaacagggac catc                                              24

<210> SEQ ID NO 26
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 26
tccacttcca aatctctatc cctaacaac                                         29

<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27
aggcattaga ggcgataagg gag                                               23

<210> SEQ ID NO 28
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 28
tcaatccaat aatagccact tgaccac                                           27

<210> SEQ ID NO 29
<211> LENGTH: 102
<212> TYPE: DNA
<213> ORGANISM: Artificial sequence
<220> FEATURE:
<223> OTHER INFORMATION: pBINPLUS multiple cloning site
```

```
<400> SEQUENCE: 29
atgaccatga ttacgccaag ctggcgcgcc aagcttgcat gcctgcaggt cgactctaga      60
ggatccccgg gtaccgagct cgaattctta attaacaatt ca                       102
```